US009555101B2

(12) United States Patent
Audonnet et al.

(10) Patent No.: US 9,555,101 B2

(45) **Date of Patent: *Jan. 31, 2017**

(54) RECOMBINANT EQUINE HERPESVIRUS-1 VACCINE CONTAINING MUTATED GLYCOPROTEIN C AND USES THEREOF

(71) Applicant: Merial Limited, Duluth, GA (US)

(72) Inventors: Jean Christophe Audonnet, Lyons (FR); Jules Maarten Minke, Corbas (FR); Nikolaus Osterrieder, Potsdam (DE); Guanggang Ma, Shanghai (CN)

(73) Assignee: Merial, Inc., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/543,300

(22) Filed: Nov. 17, 2014

(65) Prior Publication Data

US 2015/0190502 A1 Jul. 9, 2015

Related U.S. Application Data

(63) Continuation of application No. 13/840,935, filed on Mar. 15, 2013, now Pat. No. 8,916,371.

(60) Provisional application No. 61/613,151, filed on Mar. 20, 2012.

(51) Int. Cl.

| | |
|---|---|
| ***A61K 39/245*** | (2006.01) |
| ***C12N 7/00*** | (2006.01) |
| ***A61K 39/12*** | (2006.01) |
| ***C07K 14/005*** | (2006.01) |
| ***A61K 39/00*** | (2006.01) |

(52) U.S. Cl.

CPC ............. *A61K 39/245* (2013.01); *A61K 39/12* (2013.01); *C07K 14/005* (2013.01); *C12N 7/00* (2013.01); *A61K 2039/5254* (2013.01); *A61K 2039/552* (2013.01); *C12N 2710/16021* (2013.01); *C12N 2710/16034* (2013.01); *C12N 2710/16722* (2013.01); *C12N 2710/16734* (2013.01); *C12N 2710/16762* (2013.01)

(58) Field of Classification Search

CPC . C12N 7/00; C12N 15/86; C12N 2710/16034; C12N 2710/16061; C12N 2710/16043; C12N 2710/16011; C07K 14/005; A61K 39/245; A61K 2039/5254; A61K 39/12; A61K 35/763

See application file for complete search history.

(56) References Cited

U.S. PATENT DOCUMENTS

| | | | | |
|---|---|---|---|---|
| 5,674,499 A * | 10/1997 | Willemse | C07K 14/005 424/199.1 |
| 2005/0003342 A1* | 1/2005 | Davis Poynter | C07K 14/005 435/5 |
| 2006/0110403 A1* | 5/2006 | Beer | C12N 15/86 424/204.1 |
| 2006/0160202 A1* | 7/2006 | Osterrieder | C12N 7/00 435/235.1 |

OTHER PUBLICATIONS

Kirisawa R, Hosoi Y, Yamaya R, Taniyama H, Okamoto M, Tsunoda N, Hagiwara K, Iwai H. Isolation of equine herpesvirus-1 lacking glycoprotein C from a dead neonatal foal in Japan. Arch Virol. Dec. 2005;150(12):2549-65. Epub Jul. 14, 2005.*

Matsumura T, Smith RH, O'Callaghan DJ. DNA sequence and transcriptional analyses of the region of the equine herpesvirus type 1 Kentucky A strain genome encoding glycoprotein C. Virology. Apr. 1993;193(2):910-23.*

Matsumura T, Kondo T, Sugita S, Damiani AM, O'Callaghan DJ, Imagawa H. An equine herpesvirus type 1 recombinant with a deletion in the gE and gI genes is avirulent in young horses. Virology. Mar. 1, 1998;242(1):68-79.*

Guo PX, Goebel S, Davis S, Perkus ME, Languet B, Desmettre P, Allen G, Paoletti E. Expression in recombinant vaccinia virus of the equine herpesvirus 1 gene encoding glycoprotein gp13 and protection of immunized animals. J Virol. Oct. 1989;63(10):4189-98.*

Stokes A, Alber DG, Cameron RS, Marshall RN, Allen GP, Killington RA. The production of a truncated form of baculovirus expressed EHV-1 glycoprotein C and its role in protection of C3H (H-2Kk) mice against virus challenge. Virus Res. Oct. 1996;44(2):97-109.*

American Association of Equine Practitioners (AAEP). "Equine herpesvirus". Published online Mar. 8, 2011. https://web.archive.org/web/20110308153738/http://www.aaep.org/ehv.htm.*

Minke JM, et. al. Vet Res. Jul.-Aug. 2004;35(4):425-43.*

Lubinski J, Wang L, Mastellos D, Sahu A, Lambris JD, Friedman HM. In vivo role of complement-interacting domains of herpes simplex virus type 1 glycoprotein gC. J Exp Med. Dec. 6, 1999;190(11):1637-46. Erratum in: J Exp Med Feb. 21, 2000;191(4):following 746.*

Allen et al.,"Molecular Epizootiology, Pathogenesis, and Prophylaxis of Equine Herpesvirus-1 Infections", Prog Vet Microbiol Immunol 2, 78-144, 1986.

(Continued)

*Primary Examiner* — Rachel B Gill

(74) *Attorney, Agent, or Firm* — Judy Jarecki-Black; Ruoying Chen; Merial Inc.

(57) ABSTRACT

The present invention provides compositions or vaccines that contain a recombinant EHV-1 that elicit an immune response in animals against equine herpesvirus, including compositions comprising the recombinant EHV-1, methods of vaccination against equine herpesvirus, and kits for use with such methods and compositions.

9 Claims, 49 Drawing Sheets

(56) References Cited

OTHER PUBLICATIONS

Carroll et al., "Isolation of equine herpesvirus 1 from the brain of a horse affected with paresis", Aust Vet J 62, 345-346, 1985.

Crabb et al., "Equine herpesviruses 4 (Equine Rhinopneumonitis virus) and 1 (equine abortion virus)", Adv Virus Res 45, 153-190, 1995.

Davison et al., "The order herpevsirales", Arch Virol 154, 171-177, 2009.

Liu et al., "Crystal Structure of the Herpes Simplex Virus 1 DNA Polymerase", J Biol Chem 281, 18193-18200, 2006.

Ma et al., "Residue 752 in DNA polymerase of equine herpesvirus type 1 is non-essential for virus growth in vitro", J. of General Virology 91, 1817-1822, 2010.

Mumford et al., "Serological and virological investigations of an equid herpesvirus 1 (EHV-1) abortion storm on a stud farm in 1985", J. Reprod Fertil Suppl 35, 509-518, 1987.

Nugent et al., "Analysis of Equid Herpesvirus 1 Strain Variation Reveals a Point Mutation of the DNA Polymerase Strongly Associated with Neuropathogenic versus Nonneuropathogenic Disease Outbreaks", J. Virol 80, 4047-4060, 2006.

Osterrieder, "Construction and characterization of an equine herpesvirus 1 glycoprotein C negative mutant", Virus Research 2, 165, 1999.

Ostlund, "The Equine Herpesviruses", Vet Clin North Am Equine Pract 9, 283-294, 1993.

Smith et al., "Science: Overview Relationship between equine herpesvirus-1 myeloencephalopathy and viral genotype", Vet. Microbiol., 141, 5-11, 2010.

Van de Walle et al., "A Single-Nucleotide Polymorphism in a Herpesvirus DNA Polymerase Is Sufficient to Cause Lethal neurological Disease", J. Infect Dis 200, 20-25, 2009.

Wilson, "Equine Herpesvirus 1 Myeloencephalopathy", Vet Clin North Am Equine Pract 13, 53-72, 1997.

Kirisawa R et al., "Isolation of equine herpesvirus-1 lacking glycoprotein C from a dead neonatal foal in Japan", Archives of Virology, vol. 150 No. 12, p. 2549-2565,2005.

* cited by examiner

Figure 1

| SEQ ID NO: | type | Gene Description |
|---|---|---|
| 1 | DNA | EHV-1 DNA polymerase (Pol) gene (AY464052) from EHV-1 V592 strain |
| 2 | Protein | EHV-1 DNA polymerase (pol) protein (AAS45914.1) encoded by AY464052 from EHV-1 V592 strain |
| 3 | DNA | EHV-1 DNA polymerase (Pol) (AY665713) from EHV-1 Ab4 strain |
| 4 | Protein | EHV-1 DNA polymerase (pol) protein (AAT67287.1) encoded by AY665713 from EHV-1 Ab4 strain |
| 5 | DNA | EHV-1 DNA polymerase (Pol) (NC_001491) from EHV-1 |
| 6 | Protein | EHV-1 DNA polymerase (pol) protein (YP_053075.1) encoded by NC_001491 |
| 7 | DNA | EHV-1 glycoprotein (gC) gene (AY464052) from EHV-1 V592 strain |
| 8 | Protein | EHV-1 glycoprotein (gC) protein (AAS45900.1) encoded by AY464052 from EHV-1 V592 strain |
| 9 | DNA | EHV-1 glycoprotein (gC) gene (AY665713) from EHV-1 Ab4 strain |
| 10 | Protein | EHV-1 glycoprotein (gC) protein (AAT67273.1) encoded by AY665713) from EHV-1 Ab4 strain |
| 11 | DNA | EHV-1 glycoprotein (gC) gene (NC_001491) from EHV-1 |
| 12 | Protein | EHV-1 glycoprotein (gC) protein (YP_053061.1) encoded by NC_001491 |
| 13 | Protein | EHV-1 RacL DNA polymerase partial sequence |
| 14 | Protein | EHV-1 RacL DNA polymerase partial sequence comprising N at 752 of full length EHV-1 DNA polymerase |
| 15 | Protein | EHV-1 RacL DNA polymerase partial sequence with amino acid deletion at 752 of full length EHV-1 DNA polymerase |
| 16 | Primer | Primer PN1 |
| 17 | Primer | Primer PN2 |
| 18 | Primer | Primer P1 |
| 19 | Primer | Primer P2 |
| 20 | Primer | Primer P3 |
| 21 | Primer | Primer P4 |
| 22 | Primer | Primer P5 |
| 23 | Primer | Primer P6 |
| 24 | Primer | Primer P7 |

Figure 1 (continued)

| | | |
|---|---|---|
| 25 | Primer | Primer P8 |
| 26 | Primer | Primer P9 |
| 27 | Primer | Primer P10 |
| 28 | Primer | Primer gC-1 |
| 29 | Primer | Primer gC-2 |
| 30 | Primer | Primer ΔgC-1 |
| 31 | Primer | Primer ΔgC-2 |
| 32 | Primer | Primer Poly1 |
| 33 | Primer | Primer Poly2 |
| 34 | DNA | EHV-1 glycoprotein (gC) gene from EHV-1 RacL11 strain |
| 35 | Protein | EHV-1 glycoprotein (gC) protein from EHV-1 RacL11 strain |
| 36 | DNA | EHV-1 DNA polymerase (Pol) from EHV-1 NY03 strain |
| 37 | Protein | EHV-1 DNA polymerase (pol) protein from EHV-1 NY03 strain |

Figure 2
Cloning scheme
Fig. 2A
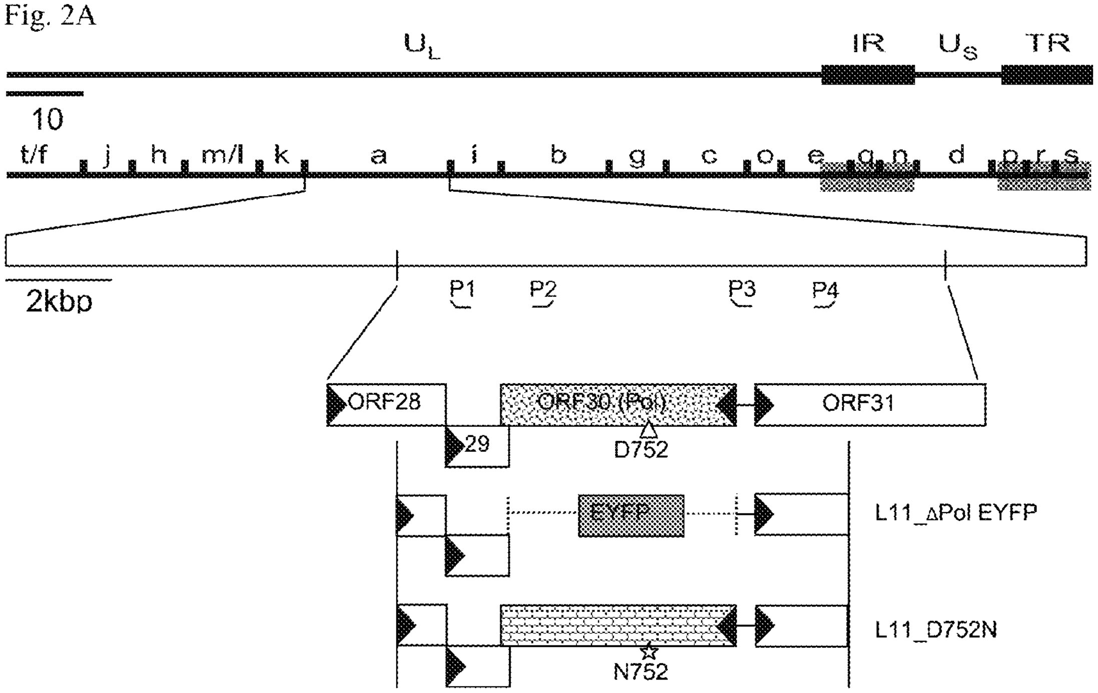
FIG. 2B
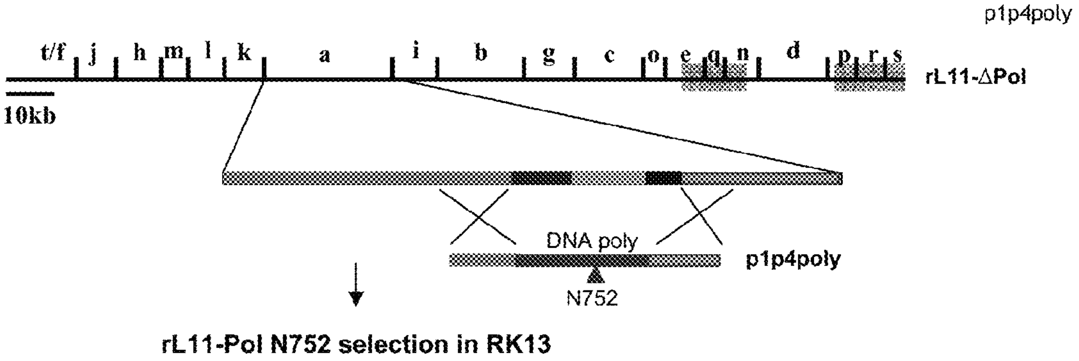

```
F D S Q A D A A S E T S E L A M D S Q S H A F D S T D E P D RacL11
F D S Q A D A A S E T S E L A M D S Q S H A F D S T D E P D rRacL11-poly N752
F D S Q A D A A S E T S E L A M D S Q S H A F D S T D E P D pRacL11-delta AA752

G V D G T P D A A G S G A T S E N G G G K P G V G R A V G Y RacL11
G V D G T P D A A G S G A T S E N G G G K P G V G R A V G Y rRacL11-poly N752
G V D G T P D A A G S G A T S E N G G G K P G V G R A V G Y pRacL11-delta AA752

Q G A K V L D P V S G F H V D P V V V F D F A S L Y P S I I RacL11
Q G A K V L D P V S G F H V D P V V V F D F A S L Y P S I I rRacL11-poly N752
Q G A K V L D P V S G F H V D P V V V F D F A S L Y P S I I pRacL11-delta AA752

Q A H N L C F T T L A L D E V D L A G L Q P S V D Y S T F E RacL11
Q A H N L C F T T L A L D E V D L A G L Q P S V N Y S T F E rRacL11-poly N752
Q A H N L C F T T L A L D E V D L A G L Q P S V - Y S T F E pRacL11-delta AA752

V G D Q K L F F V H A H I R E S L L G I L L R D W L A M R K RacL11
V G D Q K L F F V H A H I R E S L L G I L L R D W L A M R K rRacL11-poly N752
V G D Q K L F F V H A H I R E S L L G I L L R D W L A M R K pRacL11-delta AA752

A V R A R I P T S T P E E A V L L D K Q Q S A I K V I C N S RacL11
A V R A R I P T S T P E E A V L L D K Q Q S A I K V I C N S rRacL11-poly N752
A V R A R I P T S T P E E A V L L D K Q Q S A I K V I C N S pRacL11-delta AA752

V Y G F T G V A N G L L P C L                               RacL11
V Y G F T G V A N G L L P C L                               rRacL11-poly N752
V Y G F T G V A N G L L P C L                               pRacL11-delta AA752
```

RacL11: SEQ ID NO:13
rRacL11-poly N752: SEQ ID NO:14
pRacL11-delta AA752: SEQ ID NO:15

Figure 3
FIG.3A
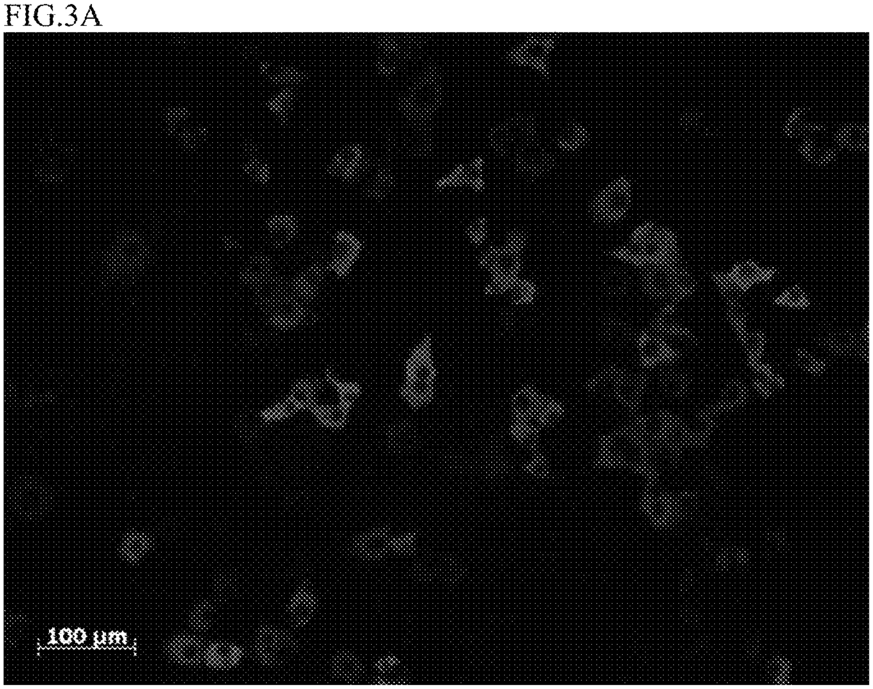
RK13-Pol
FIG.3B
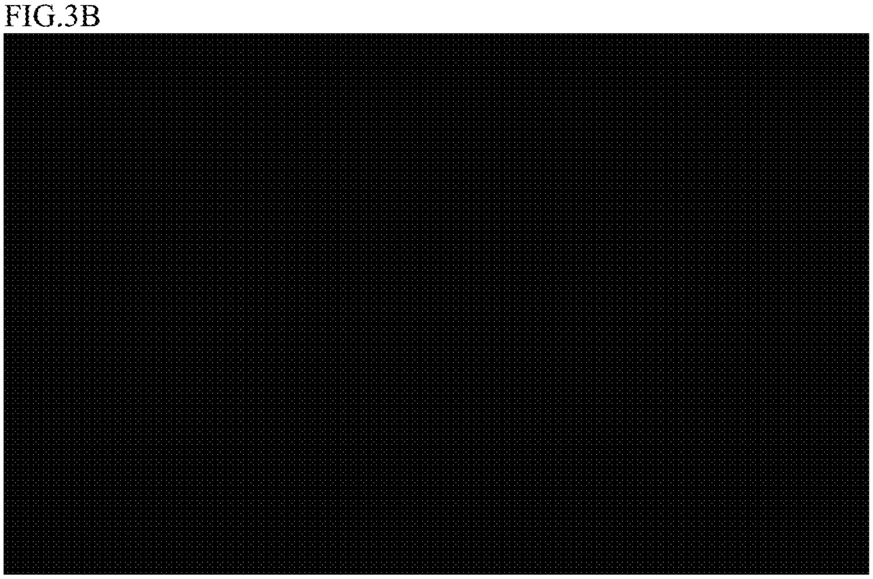
RK13

Figure 4
FIG.4A
L11-_ΔPol EYFP in RK13-Pol
FIG.4B
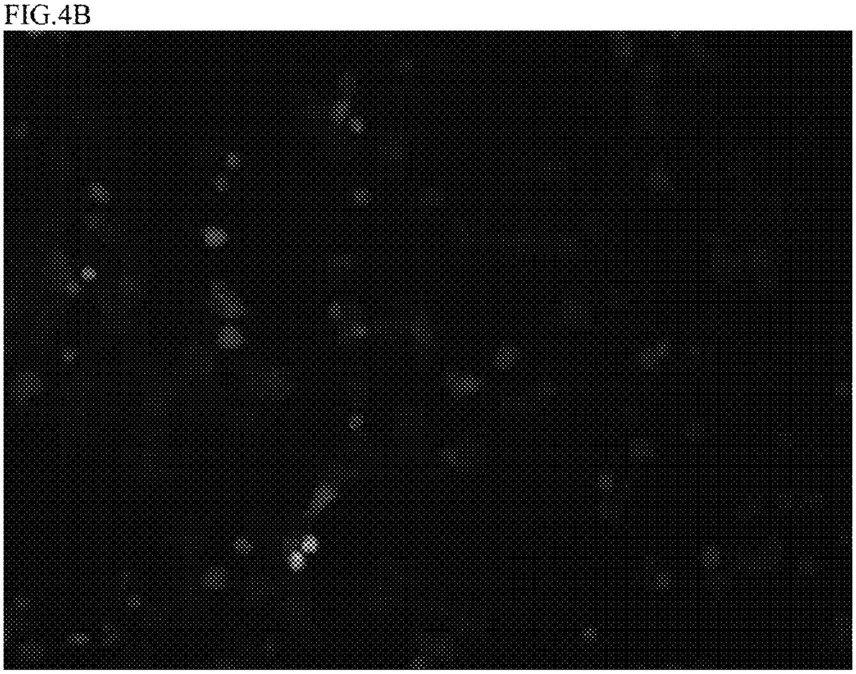
L11-_ΔPol EYFP in RK13

Anti-gM B8 anti-gC 1G4

CF test

| Group | Horse | Day -1 | Day 7 | Day 13 | Day 27 | Day 41 | Day 49 | Day 56 |
|---|---|---|---|---|---|---|---|---|
| A | 68378 | <5 | 20 | 20 | 10 | 40 | 20 | 40 |
| A | 68473 | <5 | 5 | 10 | 10 | 40 | 20 | 20 |
| A | 68504 | <5 | 10 | 20 | 10 | 20 | 10 | 40 |
| A | 68685 | <5 | 10 | 10 | 10 | 20 | 20 | 10 |
| A | 68703 | <5 | 20 | 40 | 20 | 80 | 40 | 160 |
| A | 68716 | <5 | 80 | 80 | 40 | 160 | 40 | 20 |
| A | 68837 | <5 | 20 | 40 | 40 | 40 | 40 | 20 |
| A | 68871 | <5 | 40 | 40 | 20 | 20 | 20 | 40 |
| **A** | **Mean** | **<5.0** | **25.6** | **32.5** | **20.0** | **52.5** | **26.3** | **43.8** |
| B | 68460 | <5 | <5 | 5 | 20 | 40 | 20 | 80 |
| B | 68551 | <5 | <5 | <5 | 20 | 80 | 40 | 20 |
| B | 68564 | <5 | <5 | 20 | 20 | 160 | 80 | 160 |
| B | 68581 | <5 | <5 | <5 | 40 | 160 | 40 | 80 |
| B | 68594 | <5 | 80 | 40 | 40 | 40 | 20 | 20 |
| B | 68638 | <5 | <5 | <5 | 20 | 80 | 40 | 40 |
| B | 68642 | <5 | <5 | 10 | 20 | 80 | 40 | 80 |
| B | 68655 | <5 | <5 | <5 | 5 | 80 | 40 | 40 |
| **B** | **Mean** | **<5.0** | **<14.4** | **<11.9** | **23.1** | **90.0** | **40.0** | **65.0** |
| C | 68430 | <5 | <5 | <5 | <5 | <5 | <5 | 160 |
| C | 68443 | <5 | <5 | <5 | <5 | <5 | <5 | 80 |
| C | 68577 | <5 | <5 | <5 | <5 | <5 | <5 | 40 |
| C | 68625 | <5 | <5 | <5 | <5 | <5 | <5 | 80 |
| C | 68672 | <5 | <5 | <5 | <5 | <5 | <5 | 80 |
| C | 68698 | <5 | <5 | <5 | <5 | <5 | <5 | 160 |
| C | 68841 | <5 | <5 | <5 | <5 | <5 | <5 | 160 |
| C | 68988 | <5 | <5 | <5 | <5 | <5 | <5 | 160 |
| **C** | **Mean** | **<5.0** | **<5.0** | **<5.0** | **<5.0** | **<5.0** | **<5.0** | **115.0** |

VN test

| Group | Horse | Day -1 | Day 7 | Day 13 | Day 27 | Day 41 | Day 49 | Day 56 |
|---|---|---|---|---|---|---|---|---|
| A | 68378 | <5 | <5 | 5 | 5 | 20 | 40 | 40 |
| A | 68473 | <5 | <5 | 5 | 5 | 20 | 40 | 20 |
| A | 68504 | <5 | <5 | 10 | 5 | 20 | 40 | 20 |
| A | 68685 | <5 | <5 | 5 | 5 | 20 | 40 | 20 |
| A | 68703 | <5 | <5 | 10 | 5 | 20 | 20 | 20 |
| A | 68716 | <5 | <5 | <5 | <5 | 10 | 20 | 20 |
| A | 68837 | <5 | <5 | <5 | <5 | 20 | 40 | 20 |
| A | 68871 | <5 | <5 | 10 | 10 | 20 | 40 | 80 |
| **A** | **Mean** | **<5.0** | **<5.0** | **<6.9** | **<5.6** | **18.8** | **35.0** | **30.0** |
| B | 68460 | <5 | <5 | <5 | <5 | 5 | 10 | 80 |
| B | 68551 | <5 | <5 | <5 | 5 | 10 | 20 | 20 |
| B | 68564 | <5 | <5 | <5 | <5 | 10 | 20 | 80 |
| B | 68581 | <5 | <5 | <5 | <5 | 10 | 20 | 40 |
| B | 68594 | <5 | <5 | 20 | 20 | 40 | 40 | 40 |
| B | 68638 | <5 | <5 | <5 | <5 | 10 | 10 | 10 |
| B | 68642 | <5 | <5 | <5 | 5 | 5 | 20 | 80 |
| B | 68655 | <5 | <5 | <5 | <5 | 10 | 10 | 20 |
| **B** | **Mean** | **<5.0** | **<5.0** | **<6.9** | **<6.9** | **12.5** | **18.8** | **46.3** |
| C | 68430 | <5 | <5 | <5 | <5 | <5 | <5 | <5 |
| C | 68443 | <5 | <5 | <5 | <5 | <5 | <5 | <5 |
| C | 68577 | <5 | <5 | <5 | <5 | <5 | <5 | <5 |
| C | 68625 | <5 | <5 | <5 | <5 | <5 | <5 | <5 |
| C | 68672 | <5 | <5 | <5 | <5 | <5 | <5 | <5 |
| C | 68698 | <5 | <5 | <5 | <5 | <5 | <5 | 5 |
| C | 68841 | <5 | <5 | <5 | <5 | <5 | <5 | <5 |
| C | 68988 | <5 | <5 | <5 | <5 | <5 | <5 | <5 |
| **C** | **Mean** | **<5.0** | **<5.0** | **<5.0** | **<5.0** | **<5.0** | **<5.0** | **~5.0** |

| Group | Nb of viremic horses |
|---|---|
| A | 3 |
| B | 3 |
| C | 8 |

Excretion in Nasal Swabs

| Group | Nb of horses shedding virus |
|---|---|
| A | 1 |
| B | 6 |
| C | 8 |

Figure 14

FIG. 14A EHV-1 DNA Polymerase polynucleotide sequence alignment

```
                           1                                                50
AY464052  (Pol)      (1)   TCAGCTTTGATGGGGAGCTGCTTCTAGAGTACAAAAAACTGTATGCAGTA
AY665713  (Pol)      (1)   TCAGCTTTGATGGGGAGCTGCTTCTAGAGTACAAAAAACTGTATGCAGTA
NC_001491 (Pol)      (1)   TCAGCTTTGATGGGGAGCTGCTTCTAGAGTACAAAAAACTGTATGCAGTA

                           51                                              100
AY464052  (Pol)     (51)   TTCGACGACTTTCTTCCTCCGGTGTAAAGGGCGTCAGCTTTTCAAAGCCG
AY665713  (Pol)     (51)   TTCGACGACTTTCTTCCTCCGGTGTAAAGGGCGTCAGCTTTTCAAAGCCG
NC_001491 (Pol)     (51)   TTCGACGACTTTCTTCCTCCGGTGTAAAGGGCGTCAGCTTTTCAAAGCCG

                           101                                             150
AY464052  (Pol)    (101)   GCGCGCTCAAGCAGTGCCTGGGTTTTCGTGGGGGTCTTGTGGGGGGTTTC
AY665713  (Pol)    (101)   GCGCGCTCAAGCAGTGCCTGGGTTTTCGTGGGGGTCTTGTGGGGGGTTTC
NC_001491 (Pol)    (101)   GCGCGCTCAAGCAGTGCCTGGGTTTTCGTGGGGGTCTTGTGGGGGGTTTC

                           151                                             200
AY464052  (Pol)    (151)   CGGAATAAACCGCTTTAAAAGATTTTCTGTTGTTCTCACATCATTTCCGA
AY665713  (Pol)    (151)   CGGAATAAACCGCTTTAAAAGATTTTCTGTTGTTCTCACATCATTTCCGA
NC_001491 (Pol)    (151)   CGGAATAAACCGCTTTAAAAGATTTTCTGTTGTTCTCACATCATTTCCGA

                           201                                             250
AY464052  (Pol)    (201)   ATAGAGCCTTAAAGGTCACGCTTATGGTACCCAACAGGTGGGAGAAATAG
AY665713  (Pol)    (201)   ATAGAGCCTTAAAGGTCACGCTTATGGTACCCAACAGGTGGGAGAAATAG
NC_001491 (Pol)    (201)   ATAGAGCCTTAAAGGTCACGCTTATGGTACCCAACAGGTGGGAGAAATAG

                           251                                             300
AY464052  (Pol)    (251)   TAGTCTGTGTTTAGCGGTACGTCATTCTCGGAAACATAGGTCGGGTCTTC
AY665713  (Pol)    (251)   TAGTCTGTGTTTAGCGGTACGTCATTCTCGGAAACATAGGTCGGGTCTTC
NC_001491 (Pol)    (251)   TAGTCTGTGTTTAGCGGTACGTCATTCTCGGAAACATAGGTCGGGTCTTC

                           301                                             350
AY464052  (Pol)    (301)   GGCGAGGTCGGAAACCAGCAGTTTGCGTTTAGGTTGGGGGCGTGCGGTCT
AY665713  (Pol)    (301)   GGCGAGGTCGGAAACCAGCAGTTTGCGTTTAGGTTGGGGGCGTGCGGTCT
NC_001491 (Pol)    (301)   GGCGAGGTCGGAAACCAGCAGTTTGCGTTTAGGTTGGGGGCGTGCGGTCT

                           351                                             400
AY464052  (Pol)    (351)   TGGTTACCACGGGGTTTTGGGCGGTACCGCGCATTGAGTTTACTACACCC
AY665713  (Pol)    (351)   TGGTTACCACGGGGTTTTGGGCGGTACCGCGCATTGAGTTTACTACACCC
NC_001491 (Pol)    (351)   TGGTTACCACGGGGTTTTGGGCGGTACCGCGCATTGAGTTTACTACACCC

                           401                                             450
AY464052  (Pol)    (401)   GCTTCGCGTTCCGCGGCCTCGGTCTGCGCAACTATCACATACGGAATTCT
AY665713  (Pol)    (401)   GCTTCGCGTTCCGCGGCCTCGGTCTGCGCAACTATCACATACGGAATTCT
NC_001491 (Pol)    (401)   GCTTCGCGTTCCGCGGCCTCGGTCTGCGCAACTATCACATACGGAATTCT

                           451                                             500
AY464052  (Pol)    (451)   CTCTTTTACGCTGGGCAGTTCTTCATTCCTCATGGCGAGCTTAAAGTAGA
AY665713  (Pol)    (451)   CTCTTTTACGCTGGGCAGTTCTTCATTCCTCATGGCGAGCTTAAAGTAGA
NC_001491 (Pol)    (451)   CTCTTTTACGCTGGGCAGTTCTTCATTCCTCATGGCGAGCTTAAAGTAGA

                           501                                             550
AY464052  (Pol)    (501)   CGGTGAGGTGCGGCAGGCGCTTGTTGGTATACGATTCGGGTGAGCGGCTC
AY665713  (Pol)    (501)   CGGTGAGGTGCGGCAGGCGCTTGTTGGTATACGATTCGGGTGAGCGGCTC
NC_001491 (Pol)    (501)   CGGTGAGGTGCGGCAGGCGCTTGTTGGTATACGATTCGGGTGAGCGGCTC
```

Figure 14 (continued)

```
                                 551                                              600
AY464052  (Pol)   (551)  AGCTCAGCAGTCATAACGAACTCGCGCACGTCCAAGTTGGGGGCAGTGAT
AY665713  (Pol)   (551)  AGCTCAGCAGTCATAACGAACTCGCGCACGTCCAAGTTGGGGGCAGTGAT
NC_001491 (Pol)   (551)  AGCTCAGCAGTCATAACGAACTCGCGCACGTCCAAGTTGGGGGCAGTGAT

                                 601                                              650
AY464052  (Pol)   (601)  ACGGTTGTACGCCTCTACCAGCACTCGCCCAAACTTGTCAAAGCCGCTCG
AY665713  (Pol)   (601)  ACGGTTGTACGCCTCTACCAGCACTCGCCCAAACTTGTCAAAGCCGCTCG
NC_001491 (Pol)   (601)  ACGGTTGTACGCCTCTACCAGCACTCGCCCAAACTTGTCAAAGCCGCTCG

                                 651                                              700
AY464052  (Pol)   (651)  GTAGCGGGCGCCCCACCCATTCTGCGGGAGGCACGTCTGTCACCTTTGCT
AY665713  (Pol)   (651)  GTAGCGGGCGCCCCACCCATTCTGCGGGAGGCACGTCTGTCACCTCTGCT
NC_001491 (Pol)   (651)  GTAGCGGGCGCCCCACCCATTCTGCGGGAGGCACGTCTGTCACCTCTGCT

                                 701                                              750
AY464052  (Pol)   (701)  GCCGCCGTGGCCACATCCTCGTCGTACAACAAAAGATCTACCAGATGTCG
AY665713  (Pol)   (701)  GCCGCCGTGGCCACATCCTCGTCGTACAACAAAAGATCTACCAGATGTCG
NC_001491 (Pol)   (701)  GCCGCCGTGGCCACATCCTCGTCGTACAACAAAAGATCTACCAGATGTCG

                                 751                                              800
AY464052  (Pol)   (751)  CGCGTACAAGTTTATGAAAGAGCAGTTATTTTTGCGGACCAGGTCGACCC
AY665713  (Pol)   (751)  CGCGTACAAGTTTATGAAAGAGCAGTTATTTTTGCGGACCAGGTCGACCC
NC_001491 (Pol)   (751)  CGCGTACAAGTTTATGAAAGAGCAGTTATTTTTGCGGACCAGGTCGACCC

                                 801                                              850
AY464052  (Pol)   (801)  CCTTCATGAGCATCTTCCCCCCGTTTATGACACCTATGTACTTCTTCTTG
AY665713  (Pol)   (801)  CCTTCATGAGCATCTTCCCCCCGTTTATGACACCTATGTACTTCTTCTTG
NC_001491 (Pol)   (801)  CCTTCATGAGCATCTTCCCCCCGTTTATGACACCTATGTACTTCTTCTTG

                                 851                                              900
AY464052  (Pol)   (851)  GTGATCAGCAGCAGTCGCTGAAAGGTCTTCTCACACTCCAGTTTGATGGG
AY665713  (Pol)   (851)  GTGATCAGCAGCAGTCGCTGAAAGGTCTTCTCACACTCCAGTTTGATGGG
NC_001491 (Pol)   (851)  GTGATCAGCAGCAGTCGCTGAAAGGTCTTCTCACACTCCAGTTTGATGGG

                                 901                                              950
AY464052  (Pol)   (901)  CGCTCTAAAGAGGTCCGCTGAAATCTGACGCGACATAGCATCCCCCAGCT
AY665713  (Pol)   (901)  CGCTCTAAAGAGGTCCGCTGAAATCTGACGCGACATAGCATCCCCCAGCT
NC_001491 (Pol)   (901)  CGCTCTAAAGAGGTCCGCTGAAATCTGACGCGACATAGCATCCCCCAGCT

                                 951                                             1000
AY464052  (Pol)   (951)  CCGATACCCCCTCGTACGTCAGGCCCACAAACTTGATAAACACGGAGTCG
AY665713  (Pol)   (951)  CCGATACCCCCTCGTACGTCAGGCCCACAAACTTGATAAACACGGAGTCG
NC_001491 (Pol)   (951)  CCGATACCCCCTCGTACGTCAGGCCCACAAACTTGATAAACACGGAGTCG

                                 1001                                            1050
AY464052  (Pol)  (1001)  GTGTCTCCGTAGATAACCCTGACGGAGTAAGGCTTGTGGTTTCGGAAACC
AY665713  (Pol)  (1001)  GTGTCTCCGTAGATAACCCTGACGGAGTAAGGCTTGTGGTTTCGGAAACC
NC_001491 (Pol)  (1001)  GTGTCTCCGTAGATAACCCTGACGGAGTAAGGCTTGTGGTTTCGGAAACC

                                 1051                                            1100
AY464052  (Pol)  (1051)  TATAGCCCCTGGAAAATTGTCCTCCAGCAGCTCGCGCGTCGCCCAACGAG
AY665713  (Pol)  (1051)  TATAGCCCCTGGAAAATTGTCCTCCAGCAGCTCGCGCGTCGCCCAACGAG
NC_001491 (Pol)  (1051)  TATAGCCCCTGGAAAATTGTCCTCCAGCAGCTCGCGCGTCGCCCAACGAG

                                 1101                                            1150
AY464052  (Pol)  (1101)  AGTGAACGTAATCTCGGGTCTTGAGGAGCATGTCGCGTCCTATCGTGGTA
AY665713  (Pol)  (1101)  AGTGAACGTAATCTCGGGTCTTGAGGAGCATGTCGCGTCCTATCGTGGTA
NC_001491 (Pol)  (1101)  AGTGAACGTAATCTCGGGTCTTGAGGAGCATGTCGCGTCCTATCGTGGTA
```

Figure 14 (continued)

```
                                  1151                                              1200
  AY464052  (Pol)   (1151)  ACGGTAGCCGCTATCCTCAGACACGGCAACAGGCCGTTTGCCACCCCCGT
  AY665713  (Pol)   (1151)  ACGGTAGCCGCTATCCTCAGACACGGCAACAGGCCGTTTGCCACCCCCGT
 NC_001491  (Pol)   (1151)  ACGGTAGCCGCTATCCTCAGACACGGCAACAGGCCGTTTGCCACCCCCGT

                                  1201                                              1250
  AY464052  (Pol)   (1201)  GAATCCGTAAACCGAGTTGCATATCACCTTAATCGCAGACTGCTGCTTAT
  AY665713  (Pol)   (1201)  GAATCCGTAAACCGAGTTGCATATCACCTTAATCGCAGACTGCTGCTTAT
 NC_001491  (Pol)   (1201)  GAATCCGTAAACCGAGTTGCATATCACCTTAATCGCAGACTGCTGCTTAT

                                  1251                                              1300
  AY464052  (Pol)   (1251)  CTAGTAAAACTGCCTCCTCGGGGGTGCTGGTGGGGATTCGCGCCCTCACC
  AY665713  (Pol)   (1251)  CTAGTAAAACTGCCTCCTCGGGGGTGCTGGTGGGGATTCGCGCCCTCACC
 NC_001491  (Pol)   (1251)  CTAGTAAAACTGCCTCCTCGGGGGTGCTGGTGGGGATTCGCGCCCTCACC

                                  1301                                              1350
  AY464052  (Pol)   (1301)  GCCTTTCGCATGGCCAGCCAGTCGCGCAGCAAGATGCCAAGCAGGCTTTC
  AY665713  (Pol)   (1301)  GCCTTTCGCATGGCCAGCCAGTCGCGCAGCAAGATGCCAAGCAGGCTTTC
 NC_001491  (Pol)   (1301)  GCCTTTCGCATGGCCAGCCAGTCGCGCAGCAAGATGCCAAGCAGGCTTTC

                                  1351                                              1400
  AY464052  (Pol)   (1351)  GCGAATATGGGCGTGGACAAAAAATAACTTTTGGTCACCCACCTCGAACG
  AY665713  (Pol)   (1351)  GCGAATATGGGCGTGGACAAAAAATAACTTTTGGTCACCCACCTCGAACG
 NC_001491  (Pol)   (1351)  GCGAATATGGGCGTGGACAAAAAATAACTTTTGGTCACCCACCTCGAACG

                                  1401                                              1450
  AY464052  (Pol)   (1401)  TCGAGTAGTTGACGGATGGTTGAAGCCCGGCCAGATCCACTTCATCGAGC
  AY665713  (Pol)   (1401)  TCGAGTAGTCGACGGATGGTTGAAGCCCGGCCAGATCCACTTCATCGAGC
 NC_001491  (Pol)   (1401)  TCGAGTAGTCGACGGATGGTTGAAGCCCGGCCAGATCCACTTCATCGAGC

                                  1451                                              1500
  AY464052  (Pol)   (1451)  GCCAGGGTGGTGAAACAGAGGTTATGGGCCTGGATAATGCTTGGGTATAA
  AY665713  (Pol)   (1451)  GCCAGGGTGGTGAAACAGAGGTTATGGGCCTGGATAATGCTTGGGTATAA
 NC_001491  (Pol)   (1451)  GCCAGGGTGGTGAAACAGAGGTTATGGGCCTGGATAATGCTTGGGTATAA

                                  1501                                              1550
  AY464052  (Pol)   (1501)  GCTAGCGAAGTCAAACACAACCACGGGGTCCACATGAAAGCCGGATACGG
  AY665713  (Pol)   (1501)  GCTAGCGAAGTCAAACACAACCACGGGGTCCACATGAAAGCCGGATACGG
 NC_001491  (Pol)   (1501)  GCTAGCGAAGTCAAACACAACCACGGGGTCCACATGAAAGCCGGATACGG

                                  1551                                              1600
  AY464052  (Pol)   (1551)  GGTCTAGAACCTTTGCTCCCTGGTAGCCCACGGCCCTCCCGACGCCGGGC
  AY665713  (Pol)   (1551)  GGTCTAGAACCTTTGCTCCCTGGTAGCCCACGGCCCTCCCGACGCCGGGC
 NC_001491  (Pol)   (1551)  GGTCTAGAACCTTTGCTCCCTGGTAGCCCACGGCCCTCCCGACGCCGGGC

                                  1601                                              1650
  AY464052  (Pol)   (1601)  TTCCCGCCTCCGTTTTCAGAAGTAGCGCCAGATCCTGCGGCGTCCGGGGT
  AY665713  (Pol)   (1601)  TTCCCGCCTCCGTTTTCAGAAGTAGCGCCAGATCCTGCGGCGTCCGGGGT
 NC_001491  (Pol)   (1601)  TTCCCGCCTCCGTTTTCAGAAGTAGCGCCAGATCCTGCGGCGTCCGGGGT

                                  1651                                              1700
  AY464052  (Pol)   (1651)  ACCGTCCACACCGTCGGGTTCGTCTGTACTGTCGAAGGCGTGGCTTTGGC
  AY665713  (Pol)   (1651)  ACCGTCCACACCGTCGGGTTCGTCTGTACTGTCGAAGGCGTGGCTTTGGC
 NC_001491  (Pol)   (1651)  ACCGTCCACACCGTCGGGTTCGTCTGTACTGTCGAAGGCGTGGCTTTGGC

                                  1701                                              1750
  AY464052  (Pol)   (1701)  TATCCATAGCCAACTCCGAAGTCTCTGACGCGGCGTCTGCCTGACTGTCA
  AY665713  (Pol)   (1701)  TATCCATAGCCAACTCCGAAGTCTCTGACGCGGCGTCTGCCTGACTGTCA
 NC_001491  (Pol)   (1701)  TATCCATAGCCAACTCCGAAGTCTCTGACGCGGCGTCTGCCTGACTGTCA
```

Figure 14 (continued)

```
                          1751                                              1800
 AY464052 (Pol)   (1751)  AACCGGCGTCTGTTGTCTGGCAAAATGAAATTTCTCTCGCGGGCGAGTTT
 AY665713 (Pol)   (1751)  AACCGGCGTCTGTTGTCTGGCAAAATGAAATTTCTCTCGCGGGCGAGTTT
NC_001491 (Pol)   (1751)  AACCGGCGTCTGTTGTCTGGCAAAATGAAATTTCTCTCGCGGGCGAGTTT

                          1801                                              1850
 AY464052 (Pol)   (1801)  CAGCAAGCACGTGTACACGCGAATTTGCTGACCGTCAAAAATTACCCGCG
 AY665713 (Pol)   (1801)  CAGCAAGCACGTGTACACGCGAATTTGCTGACCGTCAAAAATTACCCGCG
NC_001491 (Pol)   (1801)  CAGCAAGCACGTGTACACGCGAATTTGCTGACCGTCAAAAATTACCCGCG

                          1851                                              1900
 AY464052 (Pol)   (1851)  TTAGGGTGATACGGGCGAGTTTGGCCACCGCCGATAGTTCCAGATGGGGG
 AY665713 (Pol)   (1851)  TTAGGGTGATACGGGCGAGTTTGGCCACCGCCGATAGTTCCAGATGGGGG
NC_001491 (Pol)   (1851)  TTAGGGTGATACGGGCGAGTTTGGCCACCGCCGATAGTTCCAGATGGGGG

                          1901                                              1950
 AY464052 (Pol)   (1901)  AGGTACTTAAAAAACAGCTTGCCCACCAGCCTAGAGTCCTGGATACAATA
 AY665713 (Pol)   (1901)  AGGTACTTAAAAAACAGCTTGCCCACCAGCCTAGAGTCCTGGATACAATA
NC_001491 (Pol)   (1901)  AGGTACTTAAAAAACAGCTTGCCCACCAGCCTAGAGTCCTGGATACAATA

                          1951                                              2000
 AY464052 (Pol)   (1951)  CTCTCCTATTACGCCCCTCCGGTCAGGCCCTCCCGCGTAATAGGAGGGTA
 AY665713 (Pol)   (1951)  CTCTCCTATTACGCCCCTCCGGTCAGGCCCTCCCGCGTAATAGGAGGGTA
NC_001491 (Pol)   (1951)  CTCTCCTATTACGCCCCTCCGGTCAGGCCCTCCCGCGTAATAGGAGGGTA

                          2001                                              2050
 AY464052 (Pol)   (2001)  TTTCTTTATAGGGAAGGTCTATCTTATGCTCGCCGAGGACGTCTCCCACG
 AY665713 (Pol)   (2001)  TTTCTTTATAGGGAAGGTCTATCTTATGCTCGCCGAGGACGTCTCCCACG
NC_001491 (Pol)   (2001)  TTTCTTTATAGGGAAGGTCTATCTTATGCTCGCCGAGGACGTCTCCCACG

                          2051                                              2100
 AY464052 (Pol)   (2051)  ACCGCGTCGAGTTTGTAGCTGGGTAGCTTTAGCTTTTCCGTCGCCACAGA
 AY665713 (Pol)   (2051)  ACCGCGTCGAGTTTGTAGCTGGGTAGCTTTAGCTTTTCCGTCGCCACAGA
NC_001491 (Pol)   (2051)  ACCGCGTCGAGTTTGTAGCTGGGTAGCTTTAGCTTTTCCGTCGCCACAGA

                          2101                                              2150
 AY464052 (Pol)   (2101)  ATACATGTCTAGAGATATCAGGCCATTGATTTTCACCTTGCTCTTCTTCT
 AY665713 (Pol)   (2101)  ATACATGTCTAGAGATATCAGGCCATTGATTTTCACCTTGCTCTTCTTCT
NC_001491 (Pol)   (2101)  ATACATGTCTAGAGATATCAGGCCATTGATTTTCACCTTGCTCTTCTTCT

                          2151                                              2200
 AY464052 (Pol)   (2151)  GAAAATGGTTCGTGGCGATGTCCCACACCTTAAACAGCCCCCCTTTGTTG
 AY665713 (Pol)   (2151)  GAAAATGGTTCGTGGCGATGTCCCACACCTTAAACAGCCCCCCTTTGTTG
NC_001491 (Pol)   (2151)  GAAAATGGTTCGTGGCGATGTCCCACACCTTAAACAGCCCCCCTTTGTTG

                          2201                                              2250
 AY464052 (Pol)   (2201)  AACTTGCCGTACCCGTCCAGCTTGATGTTATACACCGACGTTACCTTGTT
 AY665713 (Pol)   (2201)  AACTTGCCGTACCCGTCCAGCTTGATGTTATACACCGACGTTACCTTGTT
NC_001491 (Pol)   (2201)  AACTTGCCGTACCCGTCCAGCTTGATGTTATACACCGACGTTACCTTGTT

                          2251                                              2300
 AY464052 (Pol)   (2251)  AACTATGTACGCCCAGTCAAAATTAACGATGTTGTAGCCGGTGGCGAACT
 AY665713 (Pol)   (2251)  AACTATGTACGCCCAGTCAAAATTAACGATGTTGTAGCCGGTGGCGAACT
NC_001491 (Pol)   (2251)  AACTATGTACGCCCAGTCAAAATTAACGATGTTGTAGCCGGTGGCGAACT

                          2301                                              2350
 AY464052 (Pol)   (2301)  CGGGAGAGTACTGCTTGAGAAAGGTCAGGAAGGCAACCAGCAGCTCGTAC
 AY665713 (Pol)   (2301)  CGGGAGAGTACTGCTTGAGAAAGGTCAGGAAGGCAACCAGCAGCTCGTAC
NC_001491 (Pol)   (2301)  CGGGAGAGTACTGCTTGAGAAAGGTCAGGAAGGCAACCAGCAGCTCGTAC
```

Figure 14 (continued)

```
                              2351                                              2400
 AY464052  (Pol)   (2351)  TCGCTGTCAAACTCCAAAACCGTCGGTCTGGGCTCGCCGCGCTGGACGCA
 AY665713  (Pol)   (2351)  TCGCTGTCAAACTCCAAAACCGTCGGTCTGGGCTCGCCGCGCTGGACGCA
NC_001491  (Pol)   (2351)  TCGCTGTCAAACTCCAAAACCGTCGGTCTGGGCTCGCCGCGCTGGACGCA

                              2401                                              2450
 AY464052  (Pol)   (2401)  TGCAAACGAGTATTCCTCAGAGATATCGCATGACCCGAGGGAAAACAGCA
 AY665713  (Pol)   (2401)  TGCAAACGAGTATTCCTCAGAGATATCGCATGACCCGAGGGAAAACAGCA
NC_001491  (Pol)   (2401)  TGCAAACGAGTATTCCTCAGAGATATCGCATGACCCGAGGGAAAACAGCA

                              2451                                              2500
 AY464052  (Pol)   (2451)  GGGTGTGTTCGTGGTTCTGAGTAGCAAGCGAGTACAGCAGACAGGAGATC
 AY665713  (Pol)   (2451)  GGGTGTGTTCGTGGTTCTGAGTAGCAAGCGAGTACAGCAGACAGGAGATC
NC_001491  (Pol)   (2451)  GGGTGTGTTCGTGGTTCTGAGTAGCAAGCGAGTACAGCAGACAGGAGATC

                              2501                                              2550
 AY464052  (Pol)   (2501)  TGGATGACCAGGTCCTCTTGGTTAGTTGCCACTGGGAACGCCATTTCGTT
 AY665713  (Pol)   (2501)  TGGATGACCAGGTCCTCTTGGTTAGTTGCCACTGGGAACGCCATTTCGTT
NC_001491  (Pol)   (2501)  TGGATGACCAGGTCCTCTTGGTTAGTTGCCACTGGGAACGCCATTTCGTT

                              2551                                              2600
 AY464052  (Pol)   (2551)  ACCCGTTCCAGCTTTACACTCTATATCAAAGCACATGAGCTTATAGTCGG
 AY665713  (Pol)   (2551)  ACCCGTTCCAGCTTTACACTCTATATCAAAGCACATGAGCTTATAGTCGG
NC_001491  (Pol)   (2551)  ACCCGTTCCAGCTTTACACTCTATATCAAAGCACATGAGCTTATAGTCGG

                              2601                                              2650
 AY464052  (Pol)   (2601)  GCCAGGCAGCCTCGTCTGGTATCGGCTCCAGGTTATCGGGAGTACAGTTA
 AY665713  (Pol)   (2601)  GCCAGGCAGCCTCGTCTGGTATCGGCTCCAGGTTATCGGGAGTACAGTTA
NC_001491  (Pol)   (2601)  GCCAGGCAGCCTCGTCTGGTATCGGCTCCAGGTTATCGGGAGTACAGTTA

                              2651                                              2700
 AY464052  (Pol)   (2651)  ATCTCCACGTCGCTTGAGGTGACGTGTCGCTCAACGGGGCGAAGTTGAAC
 AY665713  (Pol)   (2651)  ATCTCCACGTCGCTTGAGGTGACGTGTCGCTCAACGGGGCGAAGTTGAAC
NC_001491  (Pol)   (2651)  ATCTCCACGTCGCTTGAGGTGACGTGTCGCTCAACGGGGCGAAGTTGAAC

                              2701                                              2750
 AY464052  (Pol)   (2701)  ACGCTCTCCGTGGGTGCCGGGTCGCAGGCGGTACCACCCAAAACTGGTAA
 AY665713  (Pol)   (2701)  ACGCTCTCCGTGGGTGCCGGGTCGCAGGCGGTACCACCCGAAACTGGTAA
NC_001491  (Pol)   (2701)  ACGCTCTCCGTGGGTGCCGGGTCGCAGGCGGTACCACCCGAAACTGGTAA

                              2751                                              2800
 AY464052  (Pol)   (2751)  AATTTTCATTGTCCAACAACAGCCGCGTGGTCACGTCCACGCTCCCCTCG
 AY665713  (Pol)   (2751)  AATTTTCATTGTCCAACAACAGCCGCGTGGTCACGTCCACGCTCCCCTCG
NC_001491  (Pol)   (2751)  AATTTTCATTGTCCAACAACAGCCGCGTGGTCACGTCCACGCTCCCCTCG

                              2801                                              2850
 AY464052  (Pol)   (2801)  AATTTTGTAATCTCCGGGTGAAAGTTGTCGCAGATGAACCCTCCCAGGCG
 AY665713  (Pol)   (2801)  AATTTTGTAATCTCCGGGTGAAAGTTGTCGCAGATGAACCCTCCCAGGCG
NC_001491  (Pol)   (2801)  AATTTTGTAATCTCCGGGTGAAAGTTGTCGCAGATGAACCCTCCCAGGCG

                              2851                                              2900
 AY464052  (Pol)   (2851)  GCTGCTGGAGGCAGATACTCTATAGTAGAGAGCTGGCTTAGATCCAAAGT
 AY665713  (Pol)   (2851)  GCTGCTGGAGGCAGATACTCTATAGTAGAGAGCTGGCTTAGATCCAAAGT
NC_001491  (Pol)   (2851)  GCTGCTGGAGGCAGATACTCTATAGTAGAGAGCTGGCTTAGATCCAAAGT

                              2901                                              2950
 AY464052  (Pol)   (2901)  AGTACAGCGTCGTGTGGCACACGGTCTCCACTTTGAAGCAGTCCGCAGAC
 AY665713  (Pol)   (2901)  AGTACAGCGTCGTGTGGCACACGGTCTCCACTTTGAAGCAGTCCGCAGAC
NC_001491  (Pol)   (2901)  AGTACAGCGTCGTGTGGCACACGGTCTCCACTTTGAAGCAGTCCGCAGAC
```

Figure 14 (continued)

```
                             2951                                              3000
  AY464052 (Pol)   (2951) ACGTGCTTTCCGCCCCACCATCCCCCGCCGCTGCCGCCGCTCTGTTTGCC
  AY665713 (Pol)   (2951) ACGTGCTTTCCGCCCCACCATCCCCCGCCGCTGCCGCCGCTCTGTTTGCC
 NC_001491 (Pol)   (2951) ACGTGCTTTCCGCCCCACCATCCCCCGCCGCTGCCGCCGCTCTGTTTGCC

                             3001                                              3050
  AY464052 (Pol)   (3001) GCCGTTGCCATTTCCCAGGGCCGCGCTCAAAGCCGAGCTGTGCGCGCAGT
  AY665713 (Pol)   (3001) GCCGTTGCCATTTCCCAGGGCCGCGCTCAAAGCCGAGCTGTGCGCGCAGT
 NC_001491 (Pol)   (3001) GCCGTTGCCATTTCCCAGGGCCGCGCTCAAAGCCGAGCTGTGCGCGCAGT

                             3051                                              3100
  AY464052 (Pol)   (3051) CCACCATTGCGCGCACGAGTTCTGCCTCGGTGGTTATTCCACAAGCGCTA
  AY665713 (Pol)   (3051) CCACCATTGCGCGCACGAGTTCTGCCTCGGTGGTTATTCCACAAGCGCTA
 NC_001491 (Pol)   (3051) CCACCATTGCGCGCACGAGTTCTGCCTCGGTGGTTATTCCACAAGCGCTA

                             3101                                              3150
  AY464052 (Pol)   (3101) TCCACCTCCGCCTTTGCCATGTAAAAATAATGGCGCACACCATAGACGTG
  AY665713 (Pol)   (3101) TCCACCTCCGCCTTTGCCATGTAAAAATAATGGCGCACACCATAGACGTG
 NC_001491 (Pol)   (3101) TCCACCTCCGCCTTTGCCATGTAAAAATAATGGCGCACACCATAGACGTG

                             3151                                              3200
  AY464052 (Pol)   (3151) AACCGCGACTCGCTTTCCACACTCGCTCATTCCCAGCAGTGTTACCACAG
  AY665713 (Pol)   (3151) AACCGCGACTCGCTTTCCACACTCGCTCATTCCCAGCAGTGTTACCACAG
 NC_001491 (Pol)   (3151) AACCGCGACTCGCTTTCCACACTCGCTCATTCCCAGCAGTGTTACCACAG

                             3201                                              3250
  AY464052 (Pol)   (3201) ACCCGCTTGGGCGGGATAGCTCAGCAAACCTGGATGGGTCATCGTGTGAG
  AY665713 (Pol)   (3201) ACCCGCTTGGGCGGGATAGCTCAGCAAACCTGGATGGGTCATCGTGTGAG
 NC_001491 (Pol)   (3201) ACCCGCTTGGGCGGGATAGCTCAGCAAACCTGGATGGGTCATCGTGTGAG

                             3251                                              3300
  AY464052 (Pol)   (3251) GCGCTCTCCGAAGTCTCTACTATGTCGTACACGTGAAATCTCTCAAATCT
  AY665713 (Pol)   (3251) GCGCTCTCCGAAGTCTCTACTATGTCGTACACGTGAAATCTCTCAAATCT
 NC_001491 (Pol)   (3251) GCGCTCTCCGAAGTCTCTACTATGTCGTACACGTGAAATCTCTCAAATCT

                             3301                                              3350
  AY464052 (Pol)   (3301) GGGGTTGAATCCATCGCCCCGAAAATCCTGGCCGTTCCAAACCCGAATCC
  AY665713 (Pol)   (3301) GGGGTTGAATCCATCGCCCCGAAAATCCTGGCCGTTCCAAACCCGAATCC
 NC_001491 (Pol)   (3301) GGGGTTGAATCCATCGCCCCGAAAATCCTGGCCGTTCCAAACCCGAATCC

                             3351                                              3400
  AY464052 (Pol)   (3351) TGCGAGGCCAGCAACCTCCGGAGGCAAAGTTCAGCACGTCGTACTCTGAG
  AY665713 (Pol)   (3351) TGCGAGGCCAGCAACCTCCGGAGGCAAAGTTCAGCACGTCGTACTCTGAG
 NC_001491 (Pol)   (3351) TGCGAGGCCAGCAACCTCCGGAGGCAAAGTTCAGCACGTCGTACTCTGAG

                             3401                                              3450
  AY464052 (Pol)   (3401) CCATCGCAGTACACTTTGGGTGGGCGCTCCAAGGTGCCCACGTGTACACC
  AY665713 (Pol)   (3401) CCATCGCAGTACACTTTGGGTGGGCGCTCCAAGGTGCCCACGTGTACACC
 NC_001491 (Pol)   (3401) CCATCGCAGTACACTTTGGGTGGGCGCTCCAAGGTGCCCACGTGTACACC

                             3451                                              3500
  AY464052 (Pol)   (3451) GCGTCGCTGGTCGGCGGGGGCTTCTTCATCGAGGCATCTTGGAGCTATAA
  AY665713 (Pol)   (3451) GCGTCGCTGGTCGGCGGGGGCTTCTTCATCGAGGCATCTTGGAGCTATAA
 NC_001491 (Pol)   (3451) GCGTCGCTGGTCGGCGGGGGCTTCTTCATCGAGGCATCTTGGAGCTATAA

                             3501                                              3550
  AY464052 (Pol)   (3501) ACTTAAAGCTACCCACCTCTGTGCAGTACGAGTGTTGGGGGGGCCTTGGG
  AY665713 (Pol)   (3501) ACTTAAAGCTACCCACCTCTGTGCAGTACGAGTGTTGGGGGGGCCTTGGG
 NC_001491 (Pol)   (3501) ACTTAAAGCTACCCACCTCTGTGCAGTACGAGTGTTGGGGGGGCCTTGGG
```

Figure 14 (continued)

```
                           3551                                             3600
 AY464052  (Pol)   (3551) CGCTCTGTCTCCGCGGTCTGCCCGCTTCCCGGCCTGAAAAATGGCCTCTT
 AY665713  (Pol)   (3551) CGCTCTGTCTCCGCGGTCTGCCCGCTTCCCGGCCTGAAAAATGGCCTCTT
NC_001491  (Pol)   (3551) CGCTCTGTCTCCGCGGTCTGCCCGCTTCCCGGCCTGAAAAATGGCCTCTT

                           3601                                             3650
 AY464052  (Pol)   (3601) GCCAATAAACGGATTAAAAAACCCGCTCCTGCGAACGGAGTTGGCCTGTT
 AY665713  (Pol)   (3601) GCCAATAAACGGATTAAAAAACCCGCTCCTGCGAACGGAGTTGGCCTGTT
NC_001491  (Pol)   (3601) GCCAATAAACGGATTAAAAAACCCGCTCCTGCGAACGGAGTTGGCCTGTT

                           3651      3663
 AY464052  (Pol)   (3651) CGCGCGCCGCCAT
 AY665713  (Pol)   (3651) CGCGCGCCGCCAT
NC_001491  (Pol)   (3651) CGCGCGCCGCCAT
```

Sequence identity percentage:

AY464052 (SEQ ID NO:1) v. AY665713 (SEQ ID NO:3): 99.9%
AY464052 (SEQ ID NO:1) v. NC_001491 (SEQ ID NO:5): 99.9%
AY665713 (SEQ ID NO:3) v. NC_001491 (SEQ ID NO:5): 100%

Figure 14 (continued)

FIG. 14B EHV-1 DNA Polymerase full length protein sequence alignment

| | | |
|---|---|---|
| | | 1 50 |
| EHV-1 Pol (SEQ2) | (1) | MAAREQANSVRRSGFFNPFIGKRPFFRPGSGQTAETERPRPPQHSYCTEV |
| EHV-1 Pol (SEQ37) | (1) | MAAREQANSVRRSGFFNPFIGKRPFFRPGSGQTAETERPRPPQHSYCTEV |
| EHV-1 Pol (SEQ4) | (1) | MAAREQANSVRRSGFFNPFIGKRPFFRPGSGQTAETERPRPPQHSYCTEV |
| EHV-1 Pol (SEQ6) | (1) | MAAREQANSVRRSGFFNPFIGKRPFFRPGSGQTAETERPRPPQHSYCTEV |
| | | 51 100 |
| EHV-1 Pol (SEQ2) | (51) | GSFKFIAPRCLDEEAPADQRRGVHVGTLERPPKVYCDGSEYDVLNFASGG |
| EHV-1 Pol (SEQ37) | (51) | GSFKFIAPRCLDEEAPADQRRGVHVGTLERPPKVYCDGSEYDVLNFASGG |
| EHV-1 Pol (SEQ4) | (51) | GSFKFIAPRCLDEEAPADQRRGVHVGTLERPPKVYCDGSEYDVLNFASGG |
| EHV-1 Pol (SEQ6) | (51) | GSFKFIAPRCLDEEAPADQRRGVHVGTLERPPKVYCDGSEYDVLNFASGG |
| | | 101 150 |
| EHV-1 Pol (SEQ2) | (101) | CWPRRIRVWNGQDFRGDGFNPRFERFHVYDIVETSESASHDDPSRFAELS |
| EHV-1 Pol (SEQ37) | (101) | CWPRRIRVWNGQDFRGDGFNPRFERFHVYDIVETSESASHDDPSRFAELS |
| EHV-1 Pol (SEQ4) | (101) | CWPRRIRVWNGQDFRGDGFNPRFERFHVYDIVETSESASHDDPSRFAELS |
| EHV-1 Pol (SEQ6) | (101) | CWPRRIRVWNGQDFRGDGFNPRFERFHVYDIVETSESASHDDPSRFAELS |
| | | 151 200 |
| EHV-1 Pol (SEQ2) | (151) | RPSGSVVTLLGMSECGKRVAVHVYGVRHYFYMAKAEVDSACGITTEAELV |
| EHV-1 Pol (SEQ37) | (151) | RPSGSVVTLLGMSECGKRVAVHVYGVRHYFYMAKAEVDSACGITTEAELV |
| EHV-1 Pol (SEQ4) | (151) | RPSGSVVTLLGMSECGKRVAVHVYGVRHYFYMAKAEVDSACGITTEAELV |
| EHV-1 Pol (SEQ6) | (151) | RPSGSVVTLLGMSECGKRVAVHVYGVRHYFYMAKAEVDSACGITTEAELV |
| | | 201 250 |
| EHV-1 Pol (SEQ2) | (201) | RAMVDCAHSSALSAALGNGNGGKQSGGSGGGWWGGKHVSADCFKVETVCH |
| EHV-1 Pol (SEQ37) | (201) | RAMVDCAHSSALSAALGNGNGGKQSGGSGGGWWGGKHVSADCFKVETVCH |
| EHV-1 Pol (SEQ4) | (201) | RAMVDCAHSSALSAALGNGNGGKQSGGSGGGWWGGKHVSADCFKVETVCH |
| EHV-1 Pol (SEQ6) | (201) | RAMVDCAHSSALSAALGNGNGGKQSGGSGGGWWGGKHVSADCFKVETVCH |
| | | 251 300 |
| EHV-1 Pol (SEQ2) | (251) | TTLYYFGSKPALYYRVSASSSRLGGFICDNFHPEITKFEGSVDVTTRLLL |
| EHV-1 Pol (SEQ37) | (251) | TTLYYFGSKPALYYRVSASSSRLGGFICDNFHPEITKFEGSVDVTTRLLL |
| EHV-1 Pol (SEQ4) | (251) | TTLYYFGSKPALYYRVSASSSRLGGFICDNFHPEITKFEGSVDVTTRLLL |
| EHV-1 Pol (SEQ6) | (251) | TTLYYFGSKPALYYRVSASSSRLGGFICDNFHPEITKFEGSVDVTTRLLL |
| | | 301 350 |
| EHV-1 Pol (SEQ2) | (301) | DNENFTSFGWYRLRPGTHGERVQLRPVERHVTSSDVEINCTPDNLEPIPD |
| EHV-1 Pol (SEQ37) | (301) | DNENFTSFGWYRLRPGTHGERVQLRPVERHVTSSDVEINCTPDNLEPIPD |
| EHV-1 Pol (SEQ4) | (301) | DNENFTSFGWYRLRPGTHGERVQLRPVERHVTSSDVEINCTPDNLEPIPD |
| EHV-1 Pol (SEQ6) | (301) | DNENFTSFGWYRLRPGTHGERVQLRPVERHVTSSDVEINCTPDNLEPIPD |
| | | 351 400 |
| EHV-1 Pol (SEQ2) | (351) | EAAWPDYKLMCFDIECKAGTGNEMAFPVATNQEDLVIQISCLLYSLATQN |
| EHV-1 Pol (SEQ37) | (351) | EAAWPDYKLMCFDIECKAGTGNEMAFPVATNQEDLVIQISCLLYSLATQN |
| EHV-1 Pol (SEQ4) | (351) | EAAWPDYKLMCFDIECKAGTGNEMAFPVATNQEDLVIQISCLLYSLATQN |
| EHV-1 Pol (SEQ6) | (351) | EAAWPDYKLMCFDIECKAGTGNEMAFPVATNQEDLVIQISCLLYSLATQN |
| | | 401 450 |
| EHV-1 Pol (SEQ2) | (401) | HEHTLLFSLGSCDISEEYSFACVQRGEPRPTVLEFDSEYELLVAFLTFLK |
| EHV-1 Pol (SEQ37) | (401) | HEHTLLFSLGSCDISEEYSFACVQRGEPRPTVLEFDSEYELLVAFLTFLK |
| EHV-1 Pol (SEQ4) | (401) | HEHTLLFSLGSCDISEEYSFACVQRGEPRPTVLEFDSEYELLVAFLTFLK |
| EHV-1 Pol (SEQ6) | (401) | HEHTLLFSLGSCDISEEYSFACVQRGEPRPTVLEFDSEYELLVAFLTFLK |

Figure 14 (continued)

```
                                 451                                              500
 EHV-1 Pol (SEQ2)       (451)    QYSPEFATGYNIVNFDWAYIVNKVTSVYNIKLDGYGKFNKGGLFKVWDIA
EHV-1 Pol (SEQ37)       (451)    QYSPEFATGYNIVNFDWAYIVNKVTSVYNIKLDGYGKFNKGGLFKVWDIA
 EHV-1 Pol (SEQ4)       (451)    QYSPEFATGYNIVNFDWAYIVNKVTSVYNIKLDGYGKFNKGGLFKVWDIA
 EHV-1 Pol (SEQ6)       (451)    QYSPEFATGYNIVNFDWAYIVNKVTSVYNIKLDGYGKFNKGGLFKVWDIA

                                 501                                              550
 EHV-1 Pol (SEQ2)       (501)    TNHFQKKSKVKINGLISLDMYSVATEKLKLPSYKLDAVVGDVLGEHKIDL
EHV-1 Pol (SEQ37)       (501)    TNHFQKKSKVKINGLISLDMYSVATEKLKLPSYKLDAVVGDVLGEHKIDL
 EHV-1 Pol (SEQ4)       (501)    TNHFQKKSKVKINGLISLDMYSVATEKLKLPSYKLDAVVGDVLGEHKIDL
 EHV-1 Pol (SEQ6)       (501)    TNHFQKKSKVKINGLISLDMYSVATEKLKLPSYKLDAVVGDVLGEHKIDL

                                 551                                              600
 EHV-1 Pol (SEQ2)       (551)    PYKEIPSYYAGGPDRRGVIGEYCIQDSRLVGKLFFKYLPHLELSAVAKLA
EHV-1 Pol (SEQ37)       (551)    PYKEIPSYYAGGPDRRGVIGEYCIQDSRLVGKLFFKYLPHLELSAVAKLA
 EHV-1 Pol (SEQ4)       (551)    PYKEIPSYYAGGPDRRGVIGEYCIQDSRLVGKLFFKYLPHLELSAVAKLA
 EHV-1 Pol (SEQ6)       (551)    PYKEIPSYYAGGPDRRGVIGEYCIQDSRLVGKLFFKYLPHLELSAVAKLA

                                 601                                              650
 EHV-1 Pol (SEQ2)       (601)    RITLTRVIFDGQQIRVYTCLLKLARERNFILPDNRRRFDSQADAASETSE
EHV-1 Pol (SEQ37)       (601)    RITLTRVIFDGQQIRVYTCLLKLARERNFILPDNRRRFDSQADAASETSE
 EHV-1 Pol (SEQ4)       (601)    RITLTRVIFDGQQIRVYTCLLKLARERNFILPDNRRRFDSQADAASETSE
 EHV-1 Pol (SEQ6)       (601)    RITLTRVIFDGQQIRVYTCLLKLARERNFILPDNRRRFDSQADAASETSE

                                 651                                              700
 EHV-1 Pol (SEQ2)       (651)    LAMDSQSHAFDSTDEPDGVDGTPDAAGSGATSENGGGKPGVGRAVGYQGA
EHV-1 Pol (SEQ37)       (651)    LAMDSQSHAFDSTDEPDGVDGTPDAAGSGATSENGGGKPGVGRAVGYQGA
 EHV-1 Pol (SEQ4)       (651)    LAMDSQSHAFDSTDEPDGVDGTPDAAGSGATSENGGGKPGVGRAVGYQGA
 EHV-1 Pol (SEQ6)       (651)    LAMDSQSHAFDSTDEPDGVDGTPDAAGSGATSENGGGKPGVGRAVGYQGA

                                 701                                              750
 EHV-1 Pol (SEQ2)       (701)    KVLDPVSGFHVDPVVVFDFASLYPSIIQAHNLCFTTLALDEVDLAGLQPS
EHV-1 Pol (SEQ37)       (701)    KVLDPVSGFHVDPVVVFDFASLYPSIIQAHNLCFTTLALDEVDLAGLQPS
 EHV-1 Pol (SEQ4)       (701)    KVLDPVSGFHVDPVVVFDFASLYPSIIQAHNLCFTTLALDEVDLAGLQPS
 EHV-1 Pol (SEQ6)       (701)    KVLDPVSGFHVDPVVVFDFASLYPSIIQAHNLCFTTLALDEVDLAGLQPS

                                 751                                              800
 EHV-1 Pol (SEQ2)       (751)    VNYSTFEVGDQKLFFVHAHIRESLLGILLRDWLAMRKAVRARIPTSTPEE
EHV-1 Pol (SEQ37)       (751)    VNYSTFEVGDQKLFFVHAHIRESLLGILLRDWLAMRKAVRARIPTSTPEE
 EHV-1 Pol (SEQ4)       (751)    VDYSTFEVGDQKLFFVHAHIRESLLGILLRDWLAMRKAVRARIPTSTPEE
 EHV-1 Pol (SEQ6)       (751)    VDYSTFEVGDQKLFFVHAHIRESLLGILLRDWLAMRKAVRARIPTSTPEE

                                 801                                              850
 EHV-1 Pol (SEQ2)       (801)    AVLLDKQQSAIKVICNSVYGFTGVANGLLPCLRIAATVTTIGRDMLLKTR
EHV-1 Pol (SEQ37)       (801)    AVLLDKQQSAIKVICNSVYGFTGVANGLLPCLRIAATVTTIGRDMLLKTR
 EHV-1 Pol (SEQ4)       (801)    AVLLDKQQSAIKVICNSVYGFTGVANGLLPCLRIAATVTTIGRDMLLKTR
 EHV-1 Pol (SEQ6)       (801)    AVLLDKQQSAIKVICNSVYGFTGVANGLLPCLRIAATVTTIGRDMLLKTR

                                 851                                              900
 EHV-1 Pol (SEQ2)       (851)    DYVHSRWATRELLEDNFPGAIGFRNHKPYSVRVIYGDTDSVFIKFVGLTY
EHV-1 Pol (SEQ37)       (851)    DYVHSRWATRELLEDNFPGAIGFRNHKPYSVRVIYGDTDSVFIKFVGLTY
 EHV-1 Pol (SEQ4)       (851)    DYVHSRWATRELLEDNFPGAIGFRNHKPYSVRVIYGDTDSVFIKFVGLTY
 EHV-1 Pol (SEQ6)       (851)    DYVHSRWATRELLEDNFPGAIGFRNHKPYSVRVIYGDTDSVFIKFVGLTY

                                 901                                              950
 EHV-1 Pol (SEQ2)       (901)    EGVSELGDAMSRQISADLFRAPIKLECEKTFQRLLLITKKKYIGVINGGK
EHV-1 Pol (SEQ37)       (901)    EGVSELGDAMSRQISADLFRAPIKLECEKTFQRLLLITKKKYIGVINGGK
 EHV-1 Pol (SEQ4)       (901)    EGVSELGDAMSRQISADLFRAPIKLECEKTFQRLLLITKKKYIGVINGGK
 EHV-1 Pol (SEQ6)       (901)    EGVSELGDAMSRQISADLFRAPIKLECEKTFQRLLLITKKKYIGVINGGK
```

Figure 14 (continued)

```
                                951                                              1000
 EHV-1 Pol (SEQ2)     (951)    MLMKGVDLVRKNNCSFINLYARHLVDLLLYDEDVATAAAKVTDVPPAEWV
EHV-1 Pol (SEQ37)     (951)    MLMKGVDLVRKNNCSFINLYARHLVDLLLYDEDVATAAARVTDVPPAEWV
 EHV-1 Pol (SEQ4)     (951)    MLMKGVDLVRKNNCSFINLYARHLVDLLLYDEDVATAAARVTDVPPAEWV
 EHV-1 Pol (SEQ6)     (951)    MLMKGVDLVRKNNCSFINLYARHLVDLLLYDEDVATAAARVTDVPPAEWV

                                1001                                             1050
 EHV-1 Pol (SEQ2)    (1001)    GRPLPSGFDKFGRVLVEAYNRITAPNLDVREFVMTAELSRSPESYTNKRL
EHV-1 Pol (SEQ37)    (1001)    GRPLPSGFDKFGRVLVEAYNRITAPNLDVREFVMTAELSRSPELYTNKRL
 EHV-1 Pol (SEQ4)    (1001)    GRPLPSGFDKFGRVLVEAYNRITAPNLDVREFVMTAELSRSPESYTNKRL
 EHV-1 Pol (SEQ6)    (1001)    GRPLPSGFDKFGRVLVEAYNRITAPNLDVREFVMTAELSRSPESYTNKRL

                                1051                                             1100
 EHV-1 Pol (SEQ2)    (1051)    PHLTVYFKLAMRNEELPSVKERIPYVIVAQTEAAEREAGVVNSMRGTAQN
EHV-1 Pol (SEQ37)    (1051)    PHLTVYFKLAMRNEELPSVKERIPYVIVAQTEAAEREAGVVNSMRGTAQN
 EHV-1 Pol (SEQ4)    (1051)    PHLTVYFKLAMRNEELPSVKERIPYVIVAQTEAAEREAGVVNSMRGTAQN
 EHV-1 Pol (SEQ6)    (1051)    PHLTVYFKLAMRNEELPSVKERIPYVIVAQTEAAEREAGVVNSMRGTAQN

                                1101                                             1150
 EHV-1 Pol (SEQ2)    (1101)    PVVTKTARPQPKRKLLVSDLAEDPTYVSENDVPLNTDYYFSHLLGTISVT
EHV-1 Pol (SEQ37)    (1101)    PVVTKTARPQPKRKLLVSDLAEDPTYVSENDVPLNTDYYFSHLLGTISVT
 EHV-1 Pol (SEQ4)    (1101)    PVVTKTARPQPKRKLLVSDLAEDPTYVSENDVPLNTDYYFSHLLGTISVT
 EHV-1 Pol (SEQ6)    (1101)    PVVTKTARPQPKRKLLVSDLAEDPTYVSENDVPLNTDYYFSHLLGTISVT

                                1151                                             1200
 EHV-1 Pol (SEQ2)    (1151)    FKALFGNDVRTTENLLKRFIPETPHKTPTKTQALLERAGFEKLTPFTPEE
EHV-1 Pol (SEQ37)    (1151)    FKALFGNDVRTTENLLKRFIPETPHKTPTKTQALLERAGFEKLTPFTPEE
 EHV-1 Pol (SEQ4)    (1151)    FKALFGNDVRTTENLLKRFIPETPHKTPTKTQALLERAGFEKLTPFTPEE
 EHV-1 Pol (SEQ6)    (1151)    FKALFGNDVRTTENLLKRFIPETPHKTPTKTQALLERAGFEKLTPFTPEE

                                1201            1220
 EHV-1 Pol (SEQ2)    (1201)    ESRRILHTVFCTLEAAPHQS
EHV-1 Pol (SEQ37)    (1201)    ESRRILHTVFCTLEAAPHQS
 EHV-1 Pol (SEQ4)    (1201)    ESRRILHTVFCTLEAAPHQS
 EHV-1 Pol (SEQ6)    (1201)    ESRRILHTVFCTLEAAPHQS
```

Sequence identity percentage:

AAS45914.1 (SEQ ID NO :2) v. AAT67287.1 (SEQ ID NO :4): 99.8%
AAS45914.1 (SEQ ID NO :2) v. YP_053075.1 (SEQ ID NO:6): 99.8%
AAT67287.1 (SEQ ID NO :4) v. YP_053075.1 (SEQ ID NO:6): 100%
AAS45914.1 (SEQ ID NO :2) v. SEQ ID NO:37: 99.8%
AAT67287.1 (SEQ ID NO :4) v. SEQ ID NO:37: 99.8%
YP_053075.1 (SEQ ID NO:6) v. SEQ ID NO:37: 99.8%

Figure 14 (continued)

FIG. 14C EHV-1 DNA Polymerase protein sequence alignment (full-length and partial)

```
                            1                                                50
EHV-1 Pol (SEQ13)      (1)  --------------------------------------------------
 EHV-1 Pol (SEQ4)      (1)  MAAREQANSVRRSGFFNPFIGKRPFFRPGSGQTAETERPRPFQHSYCTEV
EHV-1 Pol (SEQ14)      (1)  --------------------------------------------------
 EHV-1 Pol (SEQ2)      (1)  MAAREQANSVRRSGFFNPFIGKRPFFRPGSGQTAETERPRPFQHSYCTEV
EHV-1 Pol (SEQ37)      (1)  MAAREQANSVRRSGFFNPFIGKRPFFRPGSGQTAETERPRPFQHSYCTEV
EHV-1 Pol (SEQ15)      (1)  --------------------------------------------------
 EHV-1 Pol (SEQ6)      (1)  MAAREQANSVRRSGFFNPFIGKRPFFRPGSGQTAETERPRPFQHSYCTEV

                            51                                              100
EHV-1 Pol (SEQ13)      (1)  --------------------------------------------------
 EHV-1 Pol (SEQ4)     (51)  GSFKFIAPRCLDEEAPADQRRGVHVGTLERPPKVYCDGSEYDVLNFASGG
EHV-1 Pol (SEQ14)      (1)  --------------------------------------------------
 EHV-1 Pol (SEQ2)     (51)  GSFKFIAPRCLDEEAPADQRRGVHVGTLERPPKVYCDGSEYDVLNFASGG
EHV-1 Pol (SEQ37)     (51)  GSFKFIAPRCLDEEAPADQRRGVHVGTLERPPKVYCDGSEYDVLNFASGG
EHV-1 Pol (SEQ15)      (1)  --------------------------------------------------
 EHV-1 Pol (SEQ6)     (51)  GSFKFIAPRCLDEEAPADQRRGVHVGTLERPPKVYCDGSEYDVLNFASGG

                            101                                             150
EHV-1 Pol (SEQ13)      (1)  --------------------------------------------------
 EHV-1 Pol (SEQ4)    (101)  CWPRRIRVWNGQDFRGDGFNPRFERFHVYDIVETSESASHDDPSRFAELS
EHV-1 Pol (SEQ14)      (1)  --------------------------------------------------
 EHV-1 Pol (SEQ2)    (101)  CWPRRIRVWNGQDFRGDGFNPRFERFHVYDIVETSESASHDDPSRFAELS
EHV-1 Pol (SEQ37)    (101)  CWPRRIRVWNGQDFRGDGFNPRFERFHVYDIVETSESASHDDPSRFAELS
EHV-1 Pol (SEQ15)      (1)  --------------------------------------------------
 EHV-1 Pol (SEQ6)    (101)  CWPRRIRVWNGQDFRGDGFNPRFERFHVYDIVETSESASHDDPSRFAELS

                            151                                             200
EHV-1 Pol (SEQ13)      (1)  --------------------------------------------------
 EHV-1 Pol (SEQ4)    (151)  RPSGSVVTLLGMSECGKRVAVHVYGVRHYFYMAKAEVDSACGITTEAELV
EHV-1 Pol (SEQ14)      (1)  --------------------------------------------------
 EHV-1 Pol (SEQ2)    (151)  RPSGSVVTLLGMSECGKRVAVHVYGVRHYFYMAKAEVDSACGITTEAELV
EHV-1 Pol (SEQ37)    (151)  RPSGSVVTLLGMSECGKRVAVHVYGVRHYFYMAKAEVDSACGITTEAELV
EHV-1 Pol (SEQ15)      (1)  --------------------------------------------------
 EHV-1 Pol (SEQ6)    (151)  RPSGSVVTLLGMSECGKRVAVHVYGVRHYFYMAKAEVDSACGITTEAELV

                            201                                             250
EHV-1 Pol (SEQ13)      (1)  --------------------------------------------------
 EHV-1 Pol (SEQ4)    (201)  RAMVDCAHSSALSAALGNGNGGKQSGGSGGGWWGGKHVSADCFKVETVCH
EHV-1 Pol (SEQ14)      (1)  --------------------------------------------------
 EHV-1 Pol (SEQ2)    (201)  RAMVDCAHSSALSAALGNGNGGKQSGGSGGGWWGGKHVSADCFKVETVCH
EHV-1 Pol (SEQ37)    (201)  RAMVDCAHSSALSAALGNGNGGKQSGGSGGGWWGGKHVSADCFKVETVCH
EHV-1 Pol (SEQ15)      (1)  --------------------------------------------------
 EHV-1 Pol (SEQ6)    (201)  RAMVDCAHSSALSAALGNGNGGKQSGGSGGGWWGGKHVSADCFKVETVCH

                            251                                             300
EHV-1 Pol (SEQ13)      (1)  --------------------------------------------------
 EHV-1 Pol (SEQ4)    (251)  TTLYYFGSKPALYYRVSASSSRLGGFICDNFHPEITKFEGSVDVTTRLLL
EHV-1 Pol (SEQ14)      (1)  --------------------------------------------------
 EHV-1 Pol (SEQ2)    (251)  TTLYYFGSKPALYYRVSASSSRLGGFICDNFHPEITKFEGSVDVTTRLLL
EHV-1 Pol (SEQ37)    (251)  TTLYYFGSKPALYYRVSASSSRLGGFICDNFHPEITKFEGSVDVTTRLLL
EHV-1 Pol (SEQ15)      (1)  --------------------------------------------------
 EHV-1 Pol (SEQ6)    (251)  TTLYYFGSKPALYYRVSASSSRLGGFICDNFHPEITKFEGSVDVTTRLLL
```

Figure 14 (continued)

```
                                301                                               350
EHV-1 Pol (SEQ13)         (1)   --------------------------------------------------
 EHV-1 Pol (SEQ4)       (301)   DNENFTSFGWYRLRPGTHGERVQLRPVERHVTSSDVEINCTPDNLEPIPD
EHV-1 Pol (SEQ14)         (1)   --------------------------------------------------
 EHV-1 Pol (SEQ2)       (301)   DNENFTSFGWYRLRPGTHGERVQLRPVERHVTSSDVEINCTPDNLEPIPD
EHV-1 Pol (SEQ37)       (301)   DNENFTSFGWYRLRPGTHGERVQLRPVERHVTSSDVEINCTPDNLEPIPD
EHV-1 Pol (SEQ15)         (1)   --------------------------------------------------
 EHV-1 Pol (SEQ6)       (301)   DNENFTSFGWYRLRPGTHGERVQLRPVERHVTSSDVEINCTPDNLEPIPD

                                351                                               400
EHV-1 Pol (SEQ13)         (1)   --------------------------------------------------
 EHV-1 Pol (SEQ4)       (351)   EAAWPDYKLMCFDIECKAGTGNEMAFPVATNQEDLVIQISCLLYSLATQN
EHV-1 Pol (SEQ14)         (1)   --------------------------------------------------
 EHV-1 Pol (SEQ2)       (351)   EAAWPDYKLMCFDIECKAGTGNEMAFPVATNQEDLVIQISCLLYSLATQN
EHV-1 Pol (SEQ37)       (351)   EAAWPDYKLMCFDIECKAGTGNEMAFPVATNQEDLVIQISCLLYSLATQN
EHV-1 Pol (SEQ15)         (1)   --------------------------------------------------
 EHV-1 Pol (SEQ6)       (351)   EAAWPDYKLMCFDIECKAGTGNEMAFPVATNQEDLVIQISCLLYSLATQN

                                401                                               450
EHV-1 Pol (SEQ13)         (1)   --------------------------------------------------
 EHV-1 Pol (SEQ4)       (401)   HEHTLLFSLGSCDISEEYSFACVQRGEPRPTVLEFDSEYELLVAFLTFLK
EHV-1 Pol (SEQ14)         (1)   --------------------------------------------------
 EHV-1 Pol (SEQ2)       (401)   HEHTLLFSLGSCDISEEYSFACVQRGEPRPTVLEFDSEYELLVAFLTFLK
EHV-1 Pol (SEQ37)       (401)   HEHTLLFSLGSCDISEEYSFACVQRGEPRPTVLEFDSEYELLVAFLTFLK
EHV-1 Pol (SEQ15)         (1)   --------------------------------------------------
 EHV-1 Pol (SEQ6)       (401)   HEHTLLFSLGSCDISEEYSFACVQRGEPRPTVLEFDSEYELLVAFLTFLK

                                451                                               500
EHV-1 Pol (SEQ13)         (1)   --------------------------------------------------
 EHV-1 Pol (SEQ4)       (451)   QYSPEFATGYNIVNFDWAYIVNKVTSVYNIKLDGYGKFNKGGLFKVWDIA
EHV-1 Pol (SEQ14)         (1)   --------------------------------------------------
 EHV-1 Pol (SEQ2)       (451)   QYSPEFATGYNIVNFDWAYIVNKVTSVYNIKLDGYGKFNKGGLFKVWDIA
EHV-1 Pol (SEQ37)       (451)   QYSPEFATGYNIVNFDWAYIVNKVTSVYNIKLDGYGKFNKGGLFKVWDIA
EHV-1 Pol (SEQ15)         (1)   --------------------------------------------------
 EHV-1 Pol (SEQ6)       (451)   QYSPEFATGYNIVNFDWAYIVNKVTSVYNIKLDGYGKFNKGGLFKVWDIA

                                501                                               550
EHV-1 Pol (SEQ13)         (1)   --------------------------------------------------
 EHV-1 Pol (SEQ4)       (501)   TNHFQKKSKVKINGLISLDMYSVATEKLKLPSYKLDAVVGDVLGEHKIDL
EHV-1 Pol (SEQ14)         (1)   --------------------------------------------------
 EHV-1 Pol (SEQ2)       (501)   TNHFQKKSKVKINGLISLDMYSVATEKLKLPSYKLDAVVGDVLGEHKIDL
EHV-1 Pol (SEQ37)       (501)   TNHFQKKSKVKINGLISLDMYSVATEKLKLPSYKLDAVVGDVLGEHKIDL
EHV-1 Pol (SEQ15)         (1)   --------------------------------------------------
 EHV-1 Pol (SEQ6)       (501)   TNHFQKKSKVKINGLISLDMYSVATEKLKLPSYKLDAVVGDVLGEHKIDL

                                551                                               600
EHV-1 Pol (SEQ13)         (1)   --------------------------------------------------
 EHV-1 Pol (SEQ4)       (551)   PYKEIPSYYAGGPDRRGVIGEYCIQDSRLVGKLFFKYLPHLELSAVAKLA
EHV-1 Pol (SEQ14)         (1)   --------------------------------------------------
 EHV-1 Pol (SEQ2)       (551)   PYKEIPSYYAGGPDRRGVIGEYCIQDSRLVGKLFFKYLPHLELSAVAKLA
EHV-1 Pol (SEQ37)       (551)   PYKEIPSYYAGGPDRRGVIGEYCIQDSRLVGKLFFKYLPHLELSAVAKLA
EHV-1 Pol (SEQ15)         (1)   --------------------------------------------------
 EHV-1 Pol (SEQ6)       (551)   PYKEIPSYYAGGPDRRGVIGEYCIQDSRLVGKLFFKYLPHLELSAVAKLA
```

Figure 14 (continued)

```
                             601                                              650
EHV-1 Pol (SEQ13)     (1)   -------------------------------------FDSQADAASETSE
EHV-1 Pol (SEQ4)    (601)   RITLTRVIFDGQQIRVYTCLLKLARERNFILPDNRRRFDSQADAASETSE
EHV-1 Pol (SEQ14)     (1)   -------------------------------------FDSQADAASETSE
EHV-1 Pol (SEQ2)    (601)   RITLTRVIFDGQQIRVYTCLLKLARERNFILPDNRRRFDSQADAASETSE
EHV-1 Pol (SEQ37)   (601)   RITLTRVIFDGQQIRVYTCLLKLARERNFILPDNRRRFDSQADAASETSE
EHV-1 Pol (SEQ15)     (1)   -------------------------------------FDSQADAASETSE
EHV-1 Pol (SEQ6)    (601)   RITLTRVIFDGQQIRVYTCLLKLARERNFILPDNRRRFDSQADAASETSE

                             651                                              700
EHV-1 Pol (SEQ13)    (14)   LAMDSQSHAFDSTDEPDGVDGTPDAAGSGATSENGGGKPGVGRAVGYQGA
EHV-1 Pol (SEQ4)    (651)   LAMDSQSHAFDSTDEPDGVDGTPDAAGSGATSENGGGKPGVGRAVGYQGA
EHV-1 Pol (SEQ14)    (14)   LAMDSQSHAFDSTDEPDGVDGTPDAAGSGATSENGGGKPGVGRAVGYQGA
EHV-1 Pol (SEQ2)    (651)   LAMDSQSHAFDSTDEPDGVDGTPDAAGSGATSENGGGKPGVGRAVGYQGA
EHV-1 Pol (SEQ37)   (651)   LAMDSQSHAFDSTDEPDGVDGTPDAAGSGATSENGGGKPGVGRAVGYQGA
EHV-1 Pol (SEQ15)    (14)   LAMDSQSHAFDSTDEPDGVDGTPDAAGSGATSENGGGKPGVGRAVGYQGA
EHV-1 Pol (SEQ6)    (651)   LAMDSQSHAFDSTDEPDGVDGTPDAAGSGATSENGGGKPGVGRAVGYQGA

                             701                                              750
EHV-1 Pol (SEQ13)    (64)   KVLDPVSGFHVDPVVVFDFASLYPSIIQAHNLCFTTLALDEVDLAGLQPS
EHV-1 Pol (SEQ4)    (701)   KVLDPVSGFHVDPVVVFDFASLYPSIIQAHNLCFTTLALDEVDLAGLQPS
EHV-1 Pol (SEQ14)    (64)   KVLDPVSGFHVDPVVVFDFASLYPSIIQAHNLCFTTLALDEVDLAGLQPS
EHV-1 Pol (SEQ2)    (701)   KVLDPVSGFHVDPVVVFDFASLYPSIIQAHNLCFTTLALDEVDLAGLQPS
EHV-1 Pol (SEQ37)   (701)   KVLDPVSGFHVDPVVVFDFASLYPSIIQAHNLCFTTLALDEVDLAGLQPS
EHV-1 Pol (SEQ15)    (64)   KVLDPVSGFHVDPVVVFDFASLYPSIIQAHNLCFTTLALDEVDLAGLQPS
EHV-1 Pol (SEQ6)    (701)   KVLDPVSGFHVDPVVVFDFASLYPSIIQAHNLCFTTLALDEVDLAGLQPS

                             751                                              800
EHV-1 Pol (SEQ13)   (114)   VDYSTFEVGDQKLFFVHAHIRESLLGILLRDWLAMRKAVRARIPTSTPEE
EHV-1 Pol (SEQ4)    (751)   VDYSTFEVGDQKLFFVHAHIRESLLGILLRDWLAMRKAVRARIPTSTPEE
EHV-1 Pol (SEQ14)   (114)   VNYSTFEVGDQKLFFVHAHIRESLLGILLRDWLAMRKAVRARIPTSTPEE
EHV-1 Pol (SEQ2)    (751)   VNYSTFEVGDQKLFFVHAHIRESLLGILLRDWLAMRKAVRARIPTSTPEE
EHV-1 Pol (SEQ37)   (751)   VNYSTFEVGDQKLFFVHAHIRESLLGILLRDWLAMRKAVRARIPTSTPEE
EHV-1 Pol (SEQ15)   (114)   V-YSTFEVGDQKLFFVHAHIRESLLGILLRDWLAMRKAVRARIPTSTPEE
EHV-1 Pol (SEQ6)    (751)   VDYSTFEVGDQKLFFVHAHIRESLLGILLRDWLAMRKAVRARIPTSTPEE

                             801                                              850
EHV-1 Pol (SEQ13)   (164)   AVLLDKQQSAIKVICNSVYGFTGVANGLLPCL------------------
EHV-1 Pol (SEQ4)    (801)   AVLLDKQQSAIKVICNSVYGFTGVANGLLPCLRIAATVTTIGRDMLLKTR
EHV-1 Pol (SEQ14)   (164)   AVLLDKQQSAIKVICNSVYGFTGVANGLLPCL------------------
EHV-1 Pol (SEQ2)    (801)   AVLLDKQQSAIKVICNSVYGFTGVANGLLPCLRIAATVTTIGRDMLLKTR
EHV-1 Pol (SEQ37)   (801)   AVLLDKQQSAIKVICNSVYGFTGVANGLLPCLRIAATVTTIGRDMLLKTR
EHV-1 Pol (SEQ15)   (163)   AVLLDKQQSAIKVICNSVYGFTGVANGLLPCL------------------
EHV-1 Pol (SEQ6)    (801)   AVLLDKQQSAIKVICNSVYGFTGVANGLLPCLRIAATVTTIGRDMLLKTR

                             851                                              900
EHV-1 Pol (SEQ13)   (196)   --------------------------------------------------
EHV-1 Pol (SEQ4)    (851)   DYVHSRWATRELLEDNFPGAIGFRNHKPYSVRVIYGDTDSVFIKFVGLTY
EHV-1 Pol (SEQ14)   (196)   --------------------------------------------------
EHV-1 Pol (SEQ2)    (851)   DYVHSRWATRELLEDNFPGAIGFRNHKPYSVRVIYGDTDSVFIKFVGLTY
EHV-1 Pol (SEQ37)   (851)   DYVHSRWATRELLEDNFPGAIGFRNHKPYSVRVIYGDTDSVFIKFVGLTY
EHV-1 Pol (SEQ15)   (195)   --------------------------------------------------
EHV-1 Pol (SEQ6)    (851)   DYVHSRWATRELLEDNFPGAIGFRNHKPYSVRVIYGDTDSVFIKFVGLTY
```

Figure 14 (continued)

```
                                901                                               950
EHV-1 Pol (SEQ13)    (196)    --------------------------------------------------
 EHV-1 Pol (SEQ4)    (901)    EGVSELGDAMSRQISADLFRAPIKLECEKTFQRLLLITKKKYIGVINGGK
EHV-1 Pol (SEQ14)    (196)    --------------------------------------------------
 EHV-1 Pol (SEQ2)    (901)    EGVSELGDAMSRQISADLFRAPIKLECEKTFQRLLLITKKKYIGVINGGK
EHV-1 Pol (SEQ37)    (901)    EGVSELGDAMSRQISADLFRAPIKLECEKTFQRLLLITKKKYIGVINGGK
EHV-1 Pol (SEQ15)    (195)    --------------------------------------------------
 EHV-1 Pol (SEQ6)    (901)    EGVSELGDAMSRQISADLFRAPIKLECEKTFQRLLLITKKKYIGVINGGK

                                951                                              1000
EHV-1 Pol (SEQ13)    (196)    --------------------------------------------------
 EHV-1 Pol (SEQ4)    (951)    MLMKGVDLVRKNNCSFINLYARHLVDLLLYDEDVATAAAEVTDVPPAEWV
EHV-1 Pol (SEQ14)    (196)    --------------------------------------------------
 EHV-1 Pol (SEQ2)    (951)    MLMKGVDLVRKNNCSFINLYARHLVDLLLYDEDVATAAAKVTDVPPAEWV
EHV-1 Pol (SEQ37)    (951)    MLMKGVDLVRKNNCSFINLYARHLVDLLLYDEDVATAAAEVTDVPPAEWV
EHV-1 Pol (SEQ15)    (195)    --------------------------------------------------
 EHV-1 Pol (SEQ6)    (951)    MLMKGVDLVRKNNCSFINLYARHLVDLLLYDEDVATAAAEVTDVPPAEWV

                                1001                                             1050
EHV-1 Pol (SEQ13)    (196)    --------------------------------------------------
 EHV-1 Pol (SEQ4)   (1001)    GRPLPSGFDKFGRVLVEAYNRITAPNLDVREFVMTAELSRSPESYTNKRL
EHV-1 Pol (SEQ14)    (196)    --------------------------------------------------
 EHV-1 Pol (SEQ2)   (1001)    GRPLPSGFDKFGRVLVEAYNRITAPNLDVREFVMTAELSRSPESYTNKRL
EHV-1 Pol (SEQ37)   (1001)    GRPLPSGFDKFGRVLVEAYNRITAPNLDVREFVMTAELSRSPELYTNKRL
EHV-1 Pol (SEQ15)    (195)    --------------------------------------------------
 EHV-1 Pol (SEQ6)   (1001)    GRPLPSGFDKFGRVLVEAYNRITAPNLDVREFVMTAELSRSPESYTNKRL

                                1051                                             1100
EHV-1 Pol (SEQ13)    (196)    --------------------------------------------------
 EHV-1 Pol (SEQ4)   (1051)    PHLTVYFKLAMRNEELPSVKERIPYVIVAQTEAAEREAGVVNSMRGTAQN
EHV-1 Pol (SEQ14)    (196)    --------------------------------------------------
 EHV-1 Pol (SEQ2)   (1051)    PHLTVYFKLAMRNEELPSVKERIPYVIVAQTEAAEREAGVVNSMRGTAQN
EHV-1 Pol (SEQ37)   (1051)    PHLTVYFKLAMRNEELPSVKERIPYVIVAQTEAAEREAGVVNSMRGTAQN
EHV-1 Pol (SEQ15)    (195)    --------------------------------------------------
 EHV-1 Pol (SEQ6)   (1051)    PHLTVYFKLAMRNEELPSVKERIPYVIVAQTEAAEREAGVVNSMRGTAQN

                                1101                                             1150
EHV-1 Pol (SEQ13)    (196)    --------------------------------------------------
 EHV-1 Pol (SEQ4)   (1101)    PVVTKTARPQPKRKLLVSDLAEDPTYVSENDVPLNTDYYFSHLLGTISVT
EHV-1 Pol (SEQ14)    (196)    --------------------------------------------------
 EHV-1 Pol (SEQ2)   (1101)    PVVTKTARPQPKRKLLVSDLAEDPTYVSENDVPLNTDYYFSHLLGTISVT
EHV-1 Pol (SEQ37)   (1101)    PVVTKTARPQPKRKLLVSDLAEDPTYVSENDVPLNTDYYFSHLLGTISVT
EHV-1 Pol (SEQ15)    (195)    --------------------------------------------------
 EHV-1 Pol (SEQ6)   (1101)    PVVTKTARPQPKRKLLVSDLAEDPTYVSENDVPLNTDYYFSHLLGTISVT

                                1151                                             1200
EHV-1 Pol (SEQ13)    (196)    --------------------------------------------------
 EHV-1 Pol (SEQ4)   (1151)    FKALFGNDVRTTENLLKRFIPETPHKTPTKTQALLERAGFEKLTPFTPEE
EHV-1 Pol (SEQ14)    (196)    --------------------------------------------------
 EHV-1 Pol (SEQ2)   (1151)    FKALFGNDVRTTENLLKRFIPETPHKTPTKTQALLERAGFEKLTPFTPEE
EHV-1 Pol (SEQ37)   (1151)    FKALFGNDVRTTENLLKRFIPETPHKTPTKTQALLERAGFEKLTPFTPEE
EHV-1 Pol (SEQ15)    (195)    --------------------------------------------------
 EHV-1 Pol (SEQ6)   (1151)    FKALFGNDVRTTENLLKRFIPETPHKTPTKTQALLERAGFEKLTPFTPEE
```

Figure 14 (continued)

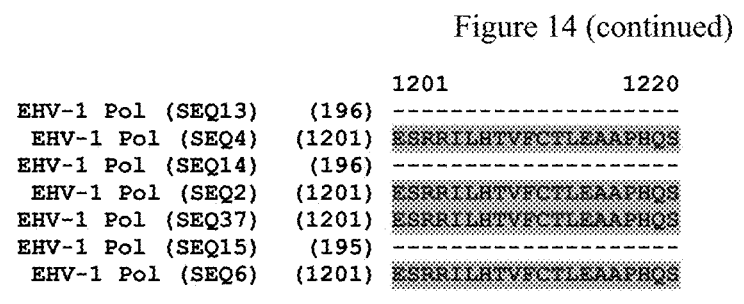

| | | 1201 1220 |
|---|---|---|
| EHV-1 Pol (SEQ13) | (196) | -------------------- |
| EHV-1 Pol (SEQ4) | (1201) | ESRRILHTVFCTLEAAFHQS |
| EHV-1 Pol (SEQ14) | (196) | -------------------- |
| EHV-1 Pol (SEQ2) | (1201) | ESRRILHTVFCTLEAAFHQS |
| EHV-1 Pol (SEQ37) | (1201) | ESRRILHTVFCTLEAAFHQS |
| EHV-1 Pol (SEQ15) | (195) | -------------------- |
| EHV-1 Pol (SEQ6) | (1201) | ESRRILHTVFCTLEAAFHQS |

Figure 15

FIG. 15A  EHV-1 glycoprotein C polynucleotide sequence alignment

```
                      1                                                  50
AY464052 (gC)    (1)  ATGTGGTTGCCTAATCTCGTGAGATTTGTGGCGGTCGCGTATCTAATCTG
AY665713 (gC)    (1)  ATGTGGTTGCCTAATCTCGTGAGATTTGTGGCGGTCGCGTATCTAATCTG
gC of RacL11     (1)  ATGTGGTTGCCTAATCTCGTGAGATTTGTGGCGGTCGCGTATCTAATCTG
NC_001491 (gC)   (1)  ATGTGGTTGCCTAATCTCGTGAGATTTGTGGCGGTCGCGTATCTAATCTG

                      51                                                 100
AY464052 (gC)   (51)  TGCCGGGGCGATATTAACTTATGCCTCTGGAGCTAGTGCTAGCTCCAGCC
AY665713 (gC)   (51)  TGCCGGGGCGATATTAACTTATGCCTCTGGAGCTAGTGCTAGCTCCAGCC
gC of RacL11    (51)  TGCCGGGGCGATATTAACTTATGCCTCTGGAGCTAGTGCTAGCTCCAGCC
NC_001491 (gC)  (51)  TGCCGGGGCGATATTAACTTATGCCTCTGGAGCTAGTGCTAGCTCCAGCC

                      101                                                150
AY464052 (gC)  (101)  AGAGTACGCCCGCTACACCAACTCACACAACTCCGAATCTAACTACCGCA
AY665713 (gC)  (101)  AGAGTACGCCCGCTACACCAACTCACACAACTCCGAATCTAACTACCGCA
gC of RacL11   (101)  AGAGTACGCCCGCTACACCAACTCACACAACTCCGAATCTAACTACCGCA
NC_001491 (gC) (101)  AGAGTACGCCCGCTACACCAACTCACACAACTCCGAATCTAACTACCGCA

                      151                                                200
AY464052 (gC)  (151)  CACGGCGCGGGCTCTGACAACACAACTAACGCAAACGGTACAGAATCTAC
AY665713 (gC)  (151)  CACGGCGCGGGCTCTGACAACACAACTAACGCAAACGGTACAGAATCTAC
gC of RacL11   (151)  CACGGCGCGGGCTCTGACAACACAACTAACGCAAACGGTACAGAATCTAC
NC_001491 (gC) (151)  CACGGCGCGGGCTCTGACAACACAACTAACGCAAACGGTACAGAATCTAC

                      201                                                250
AY464052 (gC)  (201)  ACACTCCCATGAAACCACAATCACCTGCACCAAGAGTCTCATATCTGTGC
AY665713 (gC)  (201)  ACACTCCCATGAAACCACAATCACCTGCACCAAGAGTCTCATATCTGTGC
gC of RacL11   (201)  ACACTCCCATGAAACCACAATCACCTGCACCAAGAGTCTCATATCTGTGC
NC_001491 (gC) (201)  ACACTCCCATGAAACCACAATCACCTGCACCAAGAGTCTCATATCTGTGC

                      251                                                300
AY464052 (gC)  (251)  CCTACTACAAATCTGTCGATATGAACTGTACAACGTCGGTAGGCGTAAAT
AY665713 (gC)  (251)  CCTACTACAAATCTGTCGATATGAACTGTACAACGTCGGTAGGCGTAAAT
gC of RacL11   (251)  CCTACTACAAATCTGTCGATATGAACTGTACAACGTCGGTAGGCGTAAAT
NC_001491 (gC) (251)  CCTACTACAAATCTGTCGATATGAACTGTACAACGTCGGTAGGCGTAAAT

                      301                                                350
AY464052 (gC)  (301)  TATAGCGAGTACCGCCTCGAGATTTACTTGAACCAGCGCACCCCATTTTC
AY665713 (gC)  (301)  TATAGCGAGTACCGCCTCGAGATTTACTTGAACCAGCGCACCCCATTTTC
gC of RacL11   (301)  TATAGCGAGTACCGCCTCGAGATTTACTTGAACCAGCGCACCCCATTTTC
NC_001491 (gC) (301)  TATAGCGAGTACCGCCTCGAGATTTACTTGAACCAGCGCACCCCATTTTC

                      351                                                400
AY464052 (gC)  (351)  GGGTACGCCCCCCGGCGACGAAGAAAACTACATCAACCATAACGCCACCA
AY665713 (gC)  (351)  GGGTACGCCCCCCGGCGACGAAGAAAACTACATCAACCATAACGCCACCA
gC of RacL11   (351)  GGGTACGCCCCCCGGCGACGAAGAAAACTACATCAACCATAACGCCACCA
NC_001491 (gC) (351)  GGGTACGCCCCCCGGCGACGAAGAAAACTACATCAACCATAACGCCACCA
```

Figure 15 (Continued)

```
                          401                                                450
AY464052 (gC)     (401)   AGGATCAGACTCTGCTGTTATTCTCAACGGCAGAGAGGAAAAAATCTCGA
AY665713 (gC)     (401)   AGGATCAGACTCTGCTGTTATTCTCAACGGCAGAGAGGAAAAAATCTCGA
gC of RacL11      (401)   AGGATCAGACTCTGCTGTTATTCTCAACGGCAAAGAGGAAAAAATCTCGA
NC_001491 (gC)    (401)   AGGATCAGACTCTGCTGTTATTCTCAACGGCAGAGAGGAAAAAATCTCGA

                          451                                                500
AY464052 (gC)     (451)   AGGGGTGGCCAGCTGGGAGTTATCCCAGACAGGCTACCAAAGCGCCAGCT
AY665713 (gC)     (451)   AGGGGTGGCCAGCTGGGAGTTATCCCAGACAGGCTACCAAAGCGCCAGCT
gC of RacL11      (451)   AGGGGTGGCCAGCTGGGAGTTATCCCAGACAGGCTACCAAAGCGCAAGCT
NC_001491 (gC)    (451)   AGGGGTGGCCAGCTGGGAGTTATCCCAGACAGGCTACCAAAGCGCCAGCT

                          501                                                550
AY464052 (gC)     (501)   GTTTAACCTTCCCCTCCACACGGAAGGTGGTACAAAGTTTCCACTGACCA
AY665713 (gC)     (501)   GTTTAACCTTCCCCTCCACACGGAAGGTGGTACAAAGTTTCCACTGACCA
gC of RacL11      (501)   GTTTAACCTTCCCCTCCACACGGAAGGTGGTACAAAGTTTCCACTGACCA
NC_001491 (gC)    (501)   GTTTAACCTTCCCCTCCACACGGAAGGTGGTACAAAGTTTCCACTGACCA

                          551                                                600
AY464052 (gC)     (551)   TCAAATCTGTAGATTGGCGGACGGCCGGCATTTACGTGTGGTCCTTGTAT
AY665713 (gC)     (551)   TCAAATCTGTAGATTGGCGGACGGCCGGCATTTACGTGTGGTCCTTGTAT
gC of RacL11      (551)   TCAAATCTGTAGATTGGCGGACGGCCGGCATTTACGTGTGGTCCTTGTAT
NC_001491 (gC)    (551)   TCAAATCTGTAGATTGGCGGACGGCCGGCATTTACGTGTGGTCCTTGTAT

                          601                                                650
AY464052 (gC)     (601)   GCCAAAAATGGCACGCTCGTTAACAGTACCAGCGTTACCGTCTCAACCTA
AY665713 (gC)     (601)   GCCAAAAATGGCACGCTCGTTAACAGTACCAGCGTTACCGTCTCAACCTA
gC of RacL11      (601)   GCCAAAAATGGCACGCTCGTTAACAGTACCAGCGTTACCGTCTCAACCTA
NC_001491 (gC)    (601)   GCCAAAAATGGCACGCTCGTTAACAGTACCAGCGTTACCGTCTCAACCTA

                          651                                                700
AY464052 (gC)     (651)   CAACGCACCGTTGCTGGACCTTTCCGTTCACCCGAGCCTGAAGGGGGAAA
AY665713 (gC)     (651)   CAACGCACCGTTGCTGGACCTTTCCGTTCACCCGAGCCTGAAGGGGGAAA
gC of RacL11      (651)   CAACGCACCGTTGCTGGACCTTTCCGTTCACCCGAGCCTGAAGGGGGAAA
NC_001491 (gC)    (651)   CAACGCACCGTTGCTGGACCTTTCCGTTCACCCGAGCCTGAAGGGGGAAA

                          701                                                750
AY464052 (gC)     (701)   ACTACAGGGCCACGTGCGTCGTCGCAAGCTACTTTCCACACAGCTCCGTC
AY665713 (gC)     (701)   ACTACAGGGCCACGTGCGTCGTCGCAAGCTACTTTCCACACAGCTCCGTC
gC of RacL11      (701)   ACTACAGGGCCACGTGCGTCGTCGCAAGCTACTTTCCACACAGCTCCGTC
NC_001491 (gC)    (701)   ACTACAGGGCCACGTGCGTCGTCGCAAGCTACTTTCCACACAGCTCCGTC

                          751                                                800
AY464052 (gC)     (751)   AAGCTGCGGTGGTACAAAAATGCCCGCGAGGTGGACTTTACAAAGTACGT
AY665713 (gC)     (751)   AAGCTGCGGTGGTACAAAAATGCCCGCGAGGTGGACTTTACAAAGTACGT
gC of RacL11      (751)   AAGCTGCGGTGGTACAAAAATGCCCGCGAGGTGGACTTTACAAAGTACGT
NC_001491 (gC)    (751)   AAGCTGCGGTGGTACAAAAATGCCCGCGAGGTGGACTTTACAAAGTACGT

                          801                                                850
AY464052 (gC)     (801)   TACGAACGCCTCAAGCGTGTGGGTAGACGGGCTAATCACGCGAATCTCTA
AY665713 (gC)     (801)   TACGAACGCCTCAAGCGTGTGGGTAGACGGGCTAATCACGCGAATCTCTA
gC of RacL11      (801)   TACGAACGCCTCAAGCGTGTGGGCAGACGGGCTAATCACGCGAATCTCTA
NC_001491 (gC)    (801)   TACGAACGCCTCAAGCGTGTGGGTAGACGGGCTAATCACGCGAATCTCTA
```

Figure 15 (Continued)

```
                          851                                              900
AY464052 (gC)     (851)   CGGTGTCTATCCCGGTTGATCCGGAGGAGGAATACACACCCAGTCTTCGC
AY665713 (gC)     (851)   CGGTGTCTATCCCGGTTGATCCGGAGGAGGAATACACACCCAGTCTTCGC
gC of RacL11      (851)   CGGTGTCTATCCCGGTTGGTCCGGAGGAGGAATACACACCCAGTCTTCGC
NC_001491 (gC)    (851)   CGGTGTCTATCCCGGTTGATCCGGAGGAGGAATACACACCCAGTCTTCGC

                          901                                              950
AY464052 (gC)     (901)   TGTAGCATAGACTGGTACAGGGACGAAGTATCATTTGCTCGCATAGCCAA
AY665713 (gC)     (901)   TGTAGCATAGACTGGTACAGGGACGAAGTATCATTTGCTCGCATAGCCAA
gC of RacL11      (901)   TGTAGCATAGACTGGTACAGGGACGAAGTATCATTTGCTCGCATAGCCAA
NC_001491 (gC)    (901)   TGTAGCATAGACTGGTACAGGGACGAAGTATCATTTGCTCGCATAGCCAA

                          951                                             1000
AY464052 (gC)     (951)   AGCTGGAACACCCTCTGTGTTTGTTGCCCCAACCGTGTCCGTTTCGGTAG
AY665713 (gC)     (951)   AGCTGGAACACCCTCTGTGTTTGTTGCCCCAACCGTGTCCGTTTCGGTAG
gC of RacL11      (951)   AGCTGGAACACCCTCTGTGTTTGTTGCCCCAACCGTGTCCGTTTCGGTAG
NC_001491 (gC)    (951)   AGCTGGAACACCCTCTGTGTTTGTTGCCCCAACCGTGTCCGTTTCGGTAG

                          1001                                            1050
AY464052 (gC)     (1001)  AAGACGGAGACGCCGTCTGTACGGCTAAATGCGTACCGAGCACCGGGGTG
AY665713 (gC)     (1001)  AAGACGGAGACGCCGTCTGTACGGCTAAATGCGTACCGAGCACCGGGGTG
gC of RacL11      (1001)  AAGACGGAGACGCCGTCTGTACGGCTAAATGCGTACCGAGCACCGGGGTG
NC_001491 (gC)    (1001)  AAGACGGAGACGCCGTCTGTACGGCTAAATGCGTACCGAGCACCGGGGTG

                          1051                                            1100
AY464052 (gC)     (1051)  TTCGTATCGTGGTCAGTGAACGACCACCTACCAGGGGTTCCGTCGCAAGA
AY665713 (gC)     (1051)  TTCGTATCGTGGTCAGTGAACGACCACCTACCAGGGGTTCCGTCGCAAGA
gC of RacL11      (1051)  TTCGTATCGTGGTCAGTGAACGACCACCTACCAGGGGTTCCGTCGCAAGA
NC_001491 (gC)    (1051)  TTCGTATCGTGGTCAGTGAACGACCACCTACCAGGGGTTCCGTCGCAAGA

                          1101                                            1150
AY464052 (gC)     (1101)  CATGACAACCGGAGTCTGCCCTAGCCACTCGGGATTGGTTAACATGCAAA
AY665713 (gC)     (1101)  CATGACAACCGGAGTCTGCCCTAGCCACTCGGGATTGGTTAACATGCAAA
gC of RacL11      (1101)  CATGACAACCGGAGTCTGCCCTAGCCACTCGGGATTGGTTAACATGCAAA
NC_001491 (gC)    (1101)  CATGACAACCGGAGTCTGCCCTAGCCACTCGGGATTGGTTAACATGCAAA

                          1151                                            1200
AY464052 (gC)     (1151)  GCCGCCGGCCCCTCTCAGAAGAGAATGGGGAGAGGGAGTATAGCTGCATA
AY665713 (gC)     (1151)  GCCGCCGGCCCCTCTCAGAAGAGAATGGGGAGAGGGAGTATAGCTGCATA
gC of RacL11      (1151)  GCCGCCGGCCCCTCTCAGAAGAGAATGGGGAGAGGGAGTATAGCTGCATA
NC_001491 (gC)    (1151)  GCCGCCGGCCCCTCTCAGAAGAGAATGGGGAGAGGGAGTATAGCTGCATA

                          1201                                            1250
AY464052 (gC)     (1201)  ATAGAGGGGTACCCCGACGGCCTGCCTATGTTTTCGGACACAGTGGTATA
AY665713 (gC)     (1201)  ATAGAGGGGTACCCCGACGGCCTGCCTATGTTTTCGGACACAGTGGTATA
gC of RacL11      (1201)  ATAGAGGGGTACCCCGACGGCCTGCCTATGTTTTCGGACACAGTGGTATA
NC_001491 (gC)    (1201)  ATAGAGGGGTACCCCGACGGCCTGCCTATGTTTTCGGACACAGTGGTATA

                          1251                                            1300
AY464052 (gC)     (1251)  TGACGCCTCCCCGATTGTTGAGGACAGGCCGGTTTTGACGAGCATCATCG
AY665713 (gC)     (1251)  TGACGCCTCCCCGATTGTTGAGGACAGGCCGGTTTTGACGAGCATCATCG
gC of RacL11      (1251)  TGACGCCTCCCCGATTGTTGAGGACAGGCCGGTTTTGACGAGCATCATCG
NC_001491 (gC)    (1251)  TGACGCCTCCCCGATTGTTGAGGACAGGCCGGTTTTGACGAGCATCATCG
```

Figure 15 (Continued)

```
                        1301                                              1350
AY464052 (gC)  (1301)   CAGTTACTTGCGGGGCCGCGGCACTGGCGCTGGTCGTTCTCATCACAGCC
AY665713 (gC)  (1301)   CAGTTACTTGCGGGGCCGCGGCACTGGCGCTGGTCGTTCTCATCACAGCC
gC of RacL11   (1301)   CAGTTACTTGCGGGGCCGCGGCACTGGCGCTGGTCGTTCTCATCACAGCC
NC_001491 (gC) (1301)   CAGTTACTTGCGGGGCCGCGGCACTGGCGCTGGTCGTTCTCATCACAGCC

                        1351                                              1400
AY464052 (gC)  (1351)   GTTTGTTTTTACTGCTCCAAGCCCTCACAGGCGCCGTACAAGAAGTCTGA
AY665713 (gC)  (1351)   GTCTGTTTTTACTGCTCCAAGCCCTCACAGGCGCCGTACAAGAAGTCTGA
gC of RacL11   (1351)   GTCTGTTTTTACTGCTCCAAGCCCTCACAGGCGCCGTACAAGAAGTCTGA
NC_001491 (gC) (1351)   GTCTGTTTTTACTGCTCCAAGCCCTCACAGGCGCCGTACAAGAAGTCTGA

                        1401
AY464052 (gC)  (1401)   CTTTTAG
AY665713 (gC)  (1401)   CTTTTAG
gC of RacL11   (1401)   CTTTTAG
NC_001491 (gC) (1401)   CTTTTAG
```

Sequence identity percentage:

AY464052 (gC) (SEQ ID NO :7) : AY665713 (gC) (SEQ ID NO:9): 99.9%
AY464052 (gC) (SEQ ID NO :7) : NC_001491 (gC) (SEQ ID NO:11): 99.9%
AY665713 (gC) (SEQ ID NO:9) : NC_001491 (gC) (SEQ ID NO:11): 100%
gC of RacL11 (SEQ ID NO:34) : AY464052 (gC) (SEQ ID NO :7): 99.6%
gC of RacL11 (SEQ ID NO:34) : AY665713 (gC) (SEQ ID NO:9): 99.7%
gC of RacL11 (SEQ ID NO:34) : NC_001491 (gC) (SEQ ID NO:11): 99.7%

Figure 15 (continued)

FIG. 15B EHV-1 glycoprotein C protein sequence alignment

```
                                   1                                                50
      AAS45900.1 (gC)      (1)    MWLPNLVRFVAVAYLICAGAILTYASGASASSSQSTPATPTHTTPNLTTA
      AAT67273.1 (gC)      (1)    MWLPNLVRFVAVAYLICAGAILTYASGASASSSQSTPATPTHTTPNLTTA
  gC protein of RacL11     (1)    MWLPNLVRFVAVAYLICAGAILTYASGASASSSQSTPATPTHTTPNLTTA
     YP_053061.1 (gC)      (1)    MWLPNLVRFVAVAYLICAGAILTYASGASASSSQSTPATPTHTTPNLTTA

                                   51                                              100
      AAS45900.1 (gC)     (51)    HGAGSDNTTNANGTESTHSHETTITCTKSLISVPYYKSVDMNCTTSVGVN
      AAT67273.1 (gC)     (51)    HGAGSDNTTNANGTESTHSHETTITCTKSLISVPYYKSVDMNCTTSVGVN
  gC protein of RacL11    (51)    HGAGSDNTTNANGTESTHSHETTITCTKSLISVPYYKSVDMNCTTSVGVN
     YP_053061.1 (gC)     (51)    HGAGSDNTTNANGTESTHSHETTITCTKSLISVPYYKSVDMNCTTSVGVN

                                   101                                             150
      AAS45900.1 (gC)    (101)    YSEYRLEIYLNQRTPFSGTPPGDEENYINHNATKDQTLLLFSTAERKKSR
      AAT67273.1 (gC)    (101)    YSEYRLEIYLNQRTPFSGTPPGDEENYINHNATKDQTLLLFSTAERKKSR
  gC protein of RacL11   (101)    YSEYRLEIYLNQRTPFSGTPPGDEENYINHNATKDQTLLLFSTAKRKKSR
     YP_053061.1 (gC)    (101)    YSEYRLEIYLNQRTPFSGTPPGDEENYINHNATKDQTLLLFSTAERKKSR

                                   151                                             200
      AAS45900.1 (gC)    (151)    RGGQLGVIPDRLPKRQLFNLPLHTEGGTKFPLTIKSVDWRTAGIYVWSLY
      AAT67273.1 (gC)    (151)    RGGQLGVIPDRLPKRQLFNLPLHTEGGTKFPLTIKSVDWRTAGIYVWSLY
  gC protein of RacL11   (151)    RGGQLGVIPDRLPKRKLFNLPLHTEGGTKFPLTIKSVDWRTAGIYVWSLY
     YP_053061.1 (gC)    (151)    RGGQLGVIPDRLPKRQLFNLPLHTEGGTKFPLTIKSVDWRTAGIYVWSLY

                                   201                                             250
      AAS45900.1 (gC)    (201)    AKNGTLVNSTSVTVSTYNAPLLDLSVHPSLKGENYRATCVVASYFPHSSV
      AAT67273.1 (gC)    (201)    AKNGTLVNSTSVTVSTYNAPLLDLSVHPSLKGENYRATCVVASYFPHSSV
  gC protein of RacL11   (201)    AKNGTLVNSTSVTVSTYNAPLLDLSVHPSLKGENYRATCVVASYFPHSSV
     YP_053061.1 (gC)    (201)    AKNGTLVNSTSVTVSTYNAPLLDLSVHPSLKGENYRATCVVASYFPHSSV

                                   251                                             300
      AAS45900.1 (gC)    (251)    KLRWYKNAREVDFTKYVTNASSVWVDGLITRISTVSIPVDPEEEYTPSLR
      AAT67273.1 (gC)    (251)    KLRWYKNAREVDFTKYVTNASSVWVDGLITRISTVSIPVDPEEEYTPSLR
  gC protein of RacL11   (251)    KLRWYKNAREVDFTKYVTNASSVWADGLITRISTVSIPVGPEEEYTPSLR
     YP_053061.1 (gC)    (251)    KLRWYKNAREVDFTKYVTNASSVWVDGLITRISTVSIPVDPEEEYTPSLR

                                   301                                             350
      AAS45900.1 (gC)    (301)    CSIDWYRDEVSFARIAKAGTPSVFVAPTVSVSVEDGDAVCTAKCVPSTGV
      AAT67273.1 (gC)    (301)    CSIDWYRDEVSFARIAKAGTPSVFVAPTVSVSVEDGDAVCTAKCVPSTGV
  gC protein of RacL11   (301)    CSIDWYRDEVSFARIAKAGTPSVFVAPTVSVSVEDGDAVCTAKCVPSTGV
     YP_053061.1 (gC)    (301)    CSIDWYRDEVSFARIAKAGTPSVFVAPTVSVSVEDGDAVCTAKCVPSTGV

                                   351                                             400
      AAS45900.1 (gC)    (351)    FVSWSVNDHLPGVPSQDMTTGVCPSHSGLVNMQSRRPLSEENGEREYSCI
      AAT67273.1 (gC)    (351)    FVSWSVNDHLPGVPSQDMTTGVCPSHSGLVNMQSRRPLSEENGEREYSCI
  gC protein of RacL11   (351)    FVSWSVNDHLPGVPSQDMTTGVCPSHSGLVNMQSRRPLSEENGEREYSCI
     YP_053061.1 (gC)    (351)    FVSWSVNDHLPGVPSQDMTTGVCPSHSGLVNMQSRRPLSEENGEREYSCI

                                   401                                             450
      AAS45900.1 (gC)    (401)    IEGYPDGLPMFSDTVVYDASPIVEDRPVLTSIIAVTCGAAALALVVLITA
      AAT67273.1 (gC)    (401)    IEGYPDGLPMFSDTVVYDASPIVEDRPVLTSIIAVTCGAAALALVVLITA
  gC protein of RacL11   (401)    IEGYPDGLPMFSDTVVYDASPIVEDRPVLTSIIAVTCGAAALALVVLITA
     YP_053061.1 (gC)    (401)    IEGYPDGLPMFSDTVVYDASPIVEDRPVLTSIIAVTCGAAALALVVLITA

                                   451             469
      AAS45900.1 (gC)    (451)    VCFYCSKPSQAPYKKSDF-
      AAT67273.1 (gC)    (451)    VCFYCSKPSQAPYKKSDF-
  gC protein of RacL11   (451)    VCFYCSKPSQAPYKKSDF-
     YP_053061.1 (gC)    (451)    VCFYCSKPSQAPYKKSDF-
```

Figure 15 (continued)

Sequence identity percentage:

AAS45900.1 (SEQ ID NO:8) : AAT67273.1 (SEQ ID NO:10): 100%
AAS45900.1 (SEQ ID NO:8) : YP_053061.1 (SEQ ID NO:12): 100%
AAT67273.1 (SEQ ID NO:10): YP_053061.1 (SEQ ID NO:12): 100%
gC protein of RacL11 (SEQ ID NO:35) : AAS45900.1 (SEQ ID NO:8): 98.9%
gC protein of RacL11 (SEQ ID NO:35) : AAT67273.1 (SEQ ID NO:10): 98.9%
gC protein of RacL11 (SEQ ID NO:35) : YP_053061.1 (SEQ ID NO:12): 98.9%

Figure 16

EHV-1 DNA polymerase (Pol) gene (AY464052) from EHV-1 V592 strain (SEQ ID NO:1)

```
   1 tcagctttga tggggagctg cttctagagt acaaaaaact gtatgcagta ttcgacgact
  61 ttcttcctcc ggtgtaaagg gcgtcagctt ttcaaagccg gcgcgctcaa gcagtgcctg
 121 ggttttcgtg gggtcttgt gggggtttc cggaataaac cgctttaaaa gattttctgt
 181 tgttctcaca tcatttccga atagagcctt aaaggtcacg cttatggtac ccaacaggtg
 241 ggagaaatag tagtctgtgt ttagcggtac gtcattctcg gaaacatagg tcgggtcttc
 301 ggcgaggtcg gaaaccagca gtttgcgttt aggttggggg cgtgcggtct tggttaccac
 361 ggggttttgg gcggtaccgc gcattgagtt tactacaccc gcttcgcgtt ccgcggcctc
 421 ggtctgcgca actatcacat acggaattct ctcttttacg ctgggcagtt cttcattcct
 481 catggcgagc ttaaagtaga cggtgaggtg cggcaggcgc ttgttggtat acgattcggg
 541 tgagcggctc agctcagcag tcataacgaa ctcgcgcacg tccaagttgg gggcagtgat
 601 acggttgtac gcctctacca gcactcgccc aaacttgtca aagccgctcg gtagcgggcg
 661 ccccacccat tctgcgggag gcacgtctgt cacctttgct gccgccgtgg ccacatcctc
 721 gtcgtacaac aaaagatcta ccagatgtcg cgcgtacaag ttatgaaag agcagttatt
 781 tttgcggacc aggtcgaccc ccttcatgag catcttcccc ccgtttatga cacctatgta
 841 cttcttcttg gtgatcagca gcagtcgctg aaaggtcttc tcacactcca gtttgatggg
 901 cgctctaaag aggtccgctg aaatctgacg cgacatagca tcccccagct ccgatacccc
 961 ctcgtacgtc aggcccacaa acttgataaa cacggagtcg gtgtctccgt agataaccct
1021 gacggagtaa ggcttgtggt ttcggaaacc tatagcccct ggaaaattgt cctccagcag
1081 ctcgcgcgtc gcccaacgag agtgaacgta atctcgggtc ttgaggagca tgtcgcgtcc
1141 tatcgtggta acggtagccg ctatcctcag acacggcaac aggccgtttg ccaccccgt
1201 gaatccgtaa accgagttgc atatcacctt aatcgcagac tgctgcttat ctagtaaaac
1261 tgcctcctcg ggggtgctgg tggggattcg cgccctcacc gcctttcgca tggccagcca
1321 gtcgcgcagc aagatgccaa gcaggctttc gcgaatatgg gcgtggacaa aaaataactt
1381 ttggtcaccc acctcgaacg tcgagtagtt gacggatggt tgaagcccgg ccagatccac
1441 ttcatcgagc gccagggtgg tgaaacagag gttatgggcc tggataatgc ttgggtataa
1501 gctagcgaag tcaaacacaa ccacggggtc cacatgaaag ccggatacgg ggtctagaac
1561 ctttgctccc tggtagccca cggccctccc gacgccgggc ttcccgcctc cgttttcaga
1621 agtagcgcca gatcctgcgg cgtccggggt accgtccaca ccgtcgggtt cgtctgtact
1681 gtcgaaggcg tggctttggc tatccatagc caactccgaa gtctctgacg cggcgtctgc
1741 ctgactgtca aaccggcgtc tgttgtctgg caaaatgaaa tttctctcgc gggcgagttt
1801 cagcaagcac gtgtacacgc gaatttgctg accgtcaaaa attacccgcg ttagggtgat
1861 acgggcgagt ttggccaccg ccgatagttc cagatggggg aggtacttaa aaaacagctt
1921 gcccaccagc ctagagtcct ggatacaata ctctcctatt acgcccctcc ggtcaggccc
1981 tcccgcgtaa taggagggta tttctttata gggaaggtct atcttatgct cgccgaggac
2041 gtctcccacg accgcgtcga gtttgtagct gggtagcttt agcttttccg tcgccacaga
2101 atacatgtct agagatatca ggccattgat tttcaccttg ctcttcttct gaaaatggtt
2161 cgtggcgatg tcccacacct taaacagccc ccctttgttg aacttgccgt acccgtccag
2221 cttgatgtta tacaccgacg ttaccttgtt aactatgtac gcccagtcaa aattaacgat
2281 gttgtagccg gtggcgaact cgggagagta ctgcttgaga aaggtcagga aggcaaccag
2341 cagctcgtac tcgctgtcaa actccaaaac cgtcggtctg ggctcgccgc gctggacgca
2401 tgcaaacgag tattcctcag agatatcgca tgacccgagg gaaaacagca gggtgtgttc
2461 gtggttctga gtagcaagcg agtacagcag acaggagatc tggatgacca ggtcctcttg
2521 gttagttgcc actgggaacg ccatttcgtt acccgttcca gctttacact ctatatcaaa
2581 gcacatgagc ttatagtcgg gccaggcagc ctcgtctggt atcggctcca ggttatcggg
2641 agtacagtta atctccacgt cgcttgaggt gacgtgtcgc tcaacggggc gaagttgaac
2701 acgctctccg tgggtgccgg gtcgcaggcg gtaccaccca aaactggtaa aattttcatt
2761 gtccaacaac agccgcgtgg tcacgtccac gctcccctcg aattttgtaa tctccgggtg
2821 aaagttgtcg cagatgaacc ctcccaggcg gctgctggag gcagatactc tatagtagag
2881 agctggctta gatccaaagt agtacagcgt cgtgtggcac acggtctcca ctttgaagca
2941 gtccgcagac acgtgctttc cgccccacca tcccccgccg ctgccgccgc tctgtttgcc
3001 gccgttgcca tttcccaggg ccgcgctcaa agccgagctg tgcgcgcagt ccaccattgc
3061 gcgcacgagt tctgcctcgg tggttattcc acaagcgcta tccacctccg cctttgccat
3121 gtaaaaataa tggcgcacac catagacgtg aaccgcgact cgctttccac actcgctcat
3181 tcccagcagt gttaccacag acccgcttgg gcgggatagc tcagcaaacc tggatgggtc
3241 atcgtgtgag gcgctctccg aagtctctac tatgtcgtac acgtgaaatc tctcaaatct
3301 ggggttgaat ccatcgcccc gaaaatcctg gccgttccaa acccgaatcc tgcgaggcca
3361 gcaacctccg gaggcaaagt tcagcacgtc gtactctgag ccatcgcagt acactttggg
3421 tgggcgctcc aaggtgccca cgtgtacacc gcgtcgctgg tcggcggggg cttcttcatc
3481 gaggcatctt ggagctataa acttaaagct acccacctct gtgcagtacg agtgttgggg
3541 gggccttggg cgctctgtct ccgcggtctg cccgcttccc ggcctgaaaa atggcctctt
3601 gccaataaac ggattaaaaa acccgctcct gcgaacggag ttggcctgtt cgcgcgccgc
3661 cat
```

Figure 16 (Continued)

EHV-1 DNA polymerase (pol) protein (AAS45914.1) encoded by AY464052 from EHV-1 V592 strain (1220aa) (SEQ ID NO:2)

```
MAAREQANSVRRSGFFNPFIGKRPFFRPGSGQTAETERPRPPQH
SYCTEVGSFKFIAPRCLDEEAPADQRRGVHVGTLERPPKVYCDGSEYDVLNFASGGCW
PRRIRVWNGQDFRGDGFNPRFERFHVYDIVETSESASHDDPSRFAELSRPSGSVVTLL
GMSECGKRVAVHVYGVRHYFYMAKAEVDSACGITTEAELVRAMVDCAHSSALSAALGN
GNGGKQSGGSGGGWWGGKHVSADCFKVETVCHTTLYYFGSKPALYYRVSASSSRLGGF
ICDNFHPEITKFEGSVDVTTRLLLDNENFTSFGWYRLRPGTHGERVQLRPVERHVTSS
DVEINCTPDNLEPIPDEAAWPDYKLMCFDIECKAGTGNEMAFPVATNQEDLVIQISCL
LYSLATQNHEHTLLFSLGSCDISEEYSFACVQRGEPRPTVLEFDSEYELLVAFLTFLK
QYSPEFATGYNIVNFDWAYIVNKVTSVYNIKLDGYGKFNKGGLFKVWDIATNHFQKKS
KVKINGLISLDMYSVATEKLKLPSYKLDAVVGDVLGEHKIDLPYKEIPSYYAGGPDRR
GVIGEYCIQDSRLVGKLFFKYLPHLELSAVAKLARITLTRVIFDGQQIRVYTCLLKLA
RERNFILPDNRRRFDSQADAASETSELAMDSQSHAFDSTDEPDGVDGTPDAAGSGATS
ENGGGKPGVGRAVGYQGAKVLDPVSGFHVDPVVVFDFASLYPSIIQAHNLCFTTLALD
EVDLAGLQPSVNYSTFEVGDQKLFFVHAHIRESLLGILLRDWLAMRKAVRARIPTSTP
EEAVLLDKQQSAIKVICNSVYGFTGVANGLLPCLRIAATVTTIGRDMLLKTRDYVHSR
WATRELLEDNFPGAIGFRNHKPYSVRVIYGDTDSVFIKFVGLTYEGVSELGDAMSRQI
SADLFRAPIKLECEKTFQRLLLITKKKYIGVINGGKMLMKGVDLVRKNNCSFINLYAR
HLVDLLLYDEDVATAAAKVTDVPPAEWVGRPLPSGFDKFGRVLVEAYNRITAPNLDVR
EFVMTAELSRSPESYTNKRLPHLTVYFKLAMRNEELPSVKERIPYVIVAQTEAAEREA
GVVNSMRGTAQNPVVTKTARPQPKRKLLVSDLAEDPTYVSENDVPLNTDYYFSHLLGT
ISVTFKALFGNDVRTTENLLKRFIPETPHKTPTKTQALLERAGFEKLTPFTPEEESRR
ILHTVFCTLEAAPHQS
```

EHV-1 DNA polymerase (Pol) (AY665713) from EHV-1 Ab4 strain (SEQ ID NO:3)

```
   1 tcagctttga tggggagctg cttctagagt acaaaaaact gtatgcagta ttcgacgact
  61 ttcttcctcc ggtgtaaagg gcgtcagctt ttcaaagccg gcgcgctcaa gcagtgcctg
 121 ggttttcgtg ggggtcttgt gggggtttc cggaataaac cgctttaaaa gattttctgt
 181 tgttctcaca tcatttccga atagagcctt aaaggtcacg cttatggtac ccaacaggtg
 241 ggagaaatag tagtctgtgt ttagcggtac gtcattctcg gaaacatagg tcgggtcttc
 301 ggcgaggtcg gaaaccagca gtttgcgttt aggttggggg cgtgcggtct tggttaccac
 361 ggggttttgg gcggtaccgc gcattgagtt tactacaccc gcttcgcgtt ccgcggcctc
 421 ggtctgcgca actatcacat acggaattct ctcttttacg ctgggcagtt cttcattcct
 481 catggcgagc ttaaagtaga cggtgaggtg cggcaggcgc ttgttggtat acgattcggg
 541 tgagcggctc agctcagcag tcataacgaa ctcgcgcacg tccaagttgg gggcagtgat
 601 acggttgtac gcctctacca gcactcgccc aaacttgtca aagccgctcg gtagcgggcg
 661 ccccacccat tctgcgggag gcacgtctgt cacctctgct gccgccgtgg ccacatcctc
 721 gtcgtacaac aaaagatcta ccagatgtcg cgcgtacaag tttatgaaag agcagttatt
 781 tttgcggacc aggtcgaccc ccttcatgag catcttcccc ccgtttatga cacctatgta
 841 cttcttcttg gtgatcagca gcagtcgctg aaaggtcttc tcacactcca gtttgatggg
 901 cgctctaaag aggtccgctg aaatctgacg cgacatagca tcccccagct ccgatacccc
 961 ctcgtacgtc aggcccacaa acttgataaa cacggagtcg gtgtctccgt agataaccct
1021 gacggagtaa ggcttgtggt ttcggaaacc tatagcccct ggaaaattgt cctccagcag
1081 ctcgcgcgtc gcccaacgag agtgaacgta atctcgggtc ttgaggagca tgtcgcgtcc
1141 tatcgtggta acggtagccg ctatcctcag acacggcaac aggccgtttg ccaccccccgt
1201 gaatccgtaa accgagttgc atatcacctt aatcgcagac tgctgcttat ctagtaaaac
1261 tgcctcctcg gggtgctggg tggggattcg cgccctcacc gcctttcgca tggccagcca
1321 gtcgcgcagc aagatgccaa gcaggctttc gcgaatatgg gcgtggacaa aaaataactt
1381 ttggtcaccc acctcgaacg tcgagtagtc gacggatggt tgaagcccgg ccagatccac
1441 ttcatcgagc gccagggtgg tgaaacagag gttatgggcc tggataatgc ttgggtataa
1501 gctagcgaag tcaaacacaa ccacggggtc cacatgaaag ccggatacgg ggtctagaac
1561 ctttgctccc tggtagccca cggccctccc gacgccgggc ttcccgcctc cgttttcaga
```

Figure 16 (Continued)

```
1621 agtagcgcca gatcctgcgg cgtccggggt accgtccaca ccgtcgggtt cgtctgtact
1681 gtcgaaggcg tggctttggc tatccatagc caactccgaa gtctctgacg cggcgtctgc
1741 ctgactgtca aaccggcgtc tgttgtctgg caaaatgaaa tttctctcgc gggcgagttt
1801 cagcaagcac gtgtacacgc gaatttgctg accgtcaaaa attacccgcg ttagggtgat
1861 acgggcgagt ttggccaccg ccgatagttc cagatggggg aggtacttaa aaaacagctt
1921 gcccaccagc ctagagtcct ggatacaata ctctcctatt acgcccctcc ggtcaggccc
1981 tcccgcgtaa taggagggta tttctttata gggaaggtct atcttatgct cgccgaggac
2041 gtctcccacg accgcgtcga gtttgtagct gggtagcttt agcttttccg tcgccacaga
2101 atacatgtct agagatatca ggccattgat tttcaccttg ctcttcttct gaaaatggtt
2161 cgtggcgatg tcccacacct taaacagccc ccctttgttg aacttgccgt acccgtccag
2221 cttgatgtta tacaccgacg ttaccttgtt aactatgtac gcccagtcaa aattaacgat
2281 gttgtagccg gtggcgaact cgggagagta ctgcttgaga aaggtcagga aggcaaccag
2341 cagctcgtac tcgctgtcaa actccaaaac cgtcggtctg ggctcgccgc gctggacgca
2401 tgcaaacgag tattcctcag agatatcgca tgacccgagg gaaaacagca gggtgtgttc
2461 gtggttctga gtagcaagcg agtacagcag acaggagatc tggatgacca ggtcctcttg
2521 gttagttgcc actgggaacg ccatttcgtt acccgttcca gctttacact ctatatcaaa
2581 gcacatgagc ttatagtcgg gccaggcagc ctcgtctggt atcggctcca ggttatcggg
2641 agtacagtta atctccacgt cgcttgaggt gacgtgtcgc tcaacggggc gaagttgaac
2701 acgctctccg tgggtgccgg gtcgcaggcg gtaccacccg aaactggtaa aattttcatt
2761 gtccaacaac agccgcgtgg tcacgtccac gctcccctcg aattttgtaa tctccgggtg
2821 aaagttgtcg cagatgaacc ctcccaggcg gctgctggag gcagatactc tatagtagag
2881 agctggctta gatccaaagt agtacagcgt cgtgtggcac acggtctcca ctttgaagca
2941 gtccgcagac acgtgctttc cgccccacca tcccccgccg ctgccgccgc tctgtttgcc
3001 gccgttgcca tttcccaggg ccgcgctcaa agccgagctg tgcgcgcagt ccaccattgc
3061 gcgcacgagt tctgcctcgg tggttattcc acaagcgcta tccacctccg cctttgccat
3121 gtaaaaataa tggcgcacac catagacgtg aaccgcgact cgctttccac actcgctcat
3181 tcccagcagt gttaccacag acccgcttgg gcgggatagc tcagcaaacc tggatgggtc
3241 atcgtgtgag gcgctctccg aagtctctac tatgtcgtac acgtgaaatc tctcaaatct
3301 ggggttgaat ccatcgcccc gaaaatcctg gccgttccaa acccgaatcc tgcgaggcca
3361 gcaacctccg gaggcaaagt tcagcacgtc gtactctgag ccatcgcagt acactttggg
3421 tgggcgctcc aaggtgccca cgtgtacacc gcgtcgctgg tcggcggggg cttcttcatc
3481 gaggcatctt ggagctataa acttaaagct acccacctct gtgcagtacg agtgttgggg
3541 gggccttggg cgctctgtct ccgcggtctg cccgcttccc ggcctgaaaa atggcctctt
3601 gccaataaac ggattaaaaa acccgctcct gcgaacggag ttggcctgtt cgcgcgccgc
3661 cat
```

EHV-1 DNA polymerase (pol) protein (AAT67287.1) encoded by AY665713 from EHV-1 Ab4 strain (1220aa) (SEQ ID NO:4)

```
MAAREQANSVRRSGFFNPFIGKRPFFRPGSGQTAETERPRPPQH
SYCTEVGSFKFIAPRCLDEEAPADQRRGVHVGTLERPPKVYCDGSEYDVLNFASGGCW
PRRIRVWNGQDFRGDGFNPRFERFHVYDIVETSESASHDDPSRFAELSRPSGSVVTLL
GMSECGKRVAVHVYGVRHYFYMAKAEVDSACGITTEAELVRAMVDCAHSSALSAALGN
GNGGKQSGGSGGGWWGGKHVSADCFKVETVCHTTLYYFGSKPALYYRVSASSSRLGGF
ICDNFHPEITKFEGSVDVTTRLLLDNENFTSFGWYRLRPGTHGERVQLRPVERHVTSS
DVEINCTPDNLEPIPDEAAWPDYKLMCFDIECKAGTGNEMAFPVATNQEDLVIQISCL
LYSLATQNHEHTLLFSLGSCDISEEYSFACVQRGEPRPTVLEFDSEYELLVAFLTFLK
QYSPEFATGYNIVNFDWAYIVNKVTSVYNIKLDGYGKFNKGGLFKVWDIATNHFQKKS
KVKINGLISLDMYSVATEKLKLPSYKLDAVVGDVLGEHKIDLPYKEIPSYYAGGPDRR
GVIGEYCIQDSRLVGKLFFKYLPHLELSAVAKLARITLTRVIFDGQQIRVYTCLLKLA
RERNFILPDNRRRFDSQADAASETSELAMDSQSHAFDSTDEPDGVDGTPDAAGSGATS
ENGGGKPGVGRAVGYQGAKVLDPVSGFHVDPVVVFDFASLYPSIIQAHNLCFTTLALD
EVDLAGLQPSVDYSTFEVGDQKLFFVHAHIRESLLGILLRDWLAMRKAVRARIPTSTP
```

Figure 16 (Continued)

EEAVLLDKQQSAIKVICNSVYGFTGVANGLLPCLRIAATVTTIGRDMLLKTRDYVHSR
WATRELLEDNFPGAIGFRNHKPYSVRVIYGDTDSVFIKFVGLTYEGVSELGDAMSRQI
SADLFRAPIKLECEKTFQRLLLITKKKYIGVINGGKMLMKGVDLVRKNNCSFINLYAR
HLVDLLLYDEDVATAAAEVTDVPPAEWVGRPLPSGFDKFGRVLVEAYNRITAPNLDVR
EFVMTAELSRSPESYTNKRLPHLTVYFKLAMRNEELPSVKERIPYVIVAQTEAAEREA
GVVNSMRGTAQNPVVTKTARPQPKRKLLVSDLAEDPTYVSENDVPLNTDYYFSHLLGT
ISVTFKALFGNDVRTTENLLKRFIPETPHKTPTKTQALLERAGFEKLTPFTPEEESRR
ILHTVFCTLEAAPHQS

EHV-1 DNA polymerase (Pol) (NC_001491) from EHV-1 (SEQ ID NO:5)

```
   1 tcagctttga tggggagctg cttctagagt acaaaaaact gtatgcagta ttcgacgact
  61 ttcttcctcc ggtgtaaagg gcgtcagctt ttcaaagccg gcgcgctcaa gcagtgcctg
 121 ggttttcgtg gggggtcttgt gggggtttc cggaataaac cgctttaaaa gattttctgt
 181 tgttctcaca tcatttccga atagagcctt aaaggtcacg cttatggtac ccaacaggtg
 241 ggagaaatag tagtctgtgt ttagcggtac gtcattctcg gaaacatagg tcgggtcttc
 301 ggcgaggtcg gaaaccagca gtttgcgttt aggttggggg cgtgcggtct tggttaccac
 361 ggggttttgg gcggtaccgc gcattgagtt tactacaccc gcttcgcgtt ccgcggcctc
 421 ggtctgcgca actatcacat acggaattct ctcttttacg ctgggcagtt cttcattcct
 481 catggcgagc ttaaagtaga cggtgaggtg cggcaggcgc ttgttggtat acgattcggg
 541 tgagcggctc agctcagcag tcataacgaa ctcgcgcacg tccaagttgg gggcagtgat
 601 acggttgtac gcctctacca gcactcgccc aaacttgtca aagccgctcg gtagcgggcg
 661 ccccacccat tctgcgggag gcacgtctgt cacctctgct gccgccgtgg ccacatcctc
 721 gtcgtacaac aaaagatcta ccagatgtcg cgcgtacaag tttatgaaag agcagttatt
 781 tttgcggacc aggtcgaccc ccttcatgag catcttcccc ccgtttatga cacctatgta
 841 cttcttcttg gtgatcagca gcagtcgctg aaaggtcttc tcacactcca gtttgatggg
 901 cgctctaaag aggtccgctg aaatctgacg cgacatagca tcccccagct ccgatacccc
 961 ctcgtacgtc aggcccacaa acttgataaa cacggagtcg gtgtctccgt agataaccct
1021 gacggagtaa ggcttgtggt ttcggaaacc tatagcccct ggaaaattgt cctccagcag
1081 ctcgcgcgtc gcccaacgag agtgaacgta atctcgggtc ttgaggagca tgtcgcgtcc
1141 tatcgtggta acggtagccg ctatcctcag acacggcaac aggccgtttg ccacccccgt
1201 gaatccgtaa accgagttgc atatcacctt aatcgcagac tgctgcttat ctagtaaaac
1261 tgcctcctcg gggtgctgg tggggattcg cgccctcacc gcctttcgca tggccagcca
1321 gtcgcgcagc aagatgccaa gcaggctttc gcgaatatgg gcgtggacaa aaaataactt
1381 ttggtcaccc acctcgaacg tcgagtagtc gacggatggt tgaagcccgg ccagatccac
1441 ttcatcgagc gccagggtgg tgaaacagag gttatgggcc tggataatgc ttgggtataa
1501 gctagcgaag tcaaacacaa ccacggggtc cacatgaaag ccggatacgg ggtctagaac
1561 ctttgctccc tggtagccca cggccctccc gacgccgggc ttcccgcctc cgttttcaga
1621 agtagcgcca gatcctgcgg cgtccggggt accgtccaca ccgtcgggtt cgtctgtact
1681 gtcgaaggcg tggctttggc tatccatagc caactccgaa gtctctgacg cggcgtctgc
1741 ctgactgtca aaccggcgtc tgttgtctgg caaaatgaaa tttctctcgc gggcgagttt
1801 cagcaagcac gtgtacacgc gaatttgctg accgtcaaaa attacccgcg ttagggtgat
1861 acgggcgagt ttggccaccg ccgatagttc cagatggggg aggtacttaa aaaacagctt
1921 gcccaccagc ctagagtcct ggatacaata ctctcctatt acgcccctcc ggtcaggccc
1981 tcccgcgtaa taggagggta tttctttata gggaaggtct atcttatgct cgccgaggac
2041 gtctcccacg accgcgtcga gtttgtagct gggtagcttt agcttttccg tcgccacaga
2101 atacatgtct agagatatca ggccattgat tttcaccttg ctcttcttct gaaaatggtt
2161 cgtggcgatg tcccacacct taaacagccc ccctttgttg aacttgccgt acccgtccag
2221 cttgatgtta tacaccgacg ttaccttgtt aactatgtac gcccagtcaa aattaacgat
2281 gttgtagccg gtggcgaact cgggagagta ctgcttgaga aaggtcagga aggcaaccag
2341 cagctcgtac tcgctgtcaa actccaaaac cgtcggtctg ggctcgccgc gctggacgca
2401 tgcaaacgag tattcctcag agatatcgca tgacccgagg gaaaacagca gggtgtgttc
2461 gtggttctga gtagcaagcg agtacagcag acaggagatc tggatgacca ggtcctcttg
2521 gttagttgcc actgggaacg ccatttcgtt acccgttcca gctttacact ctatatcaaa
```

Figure 16 (Continued)

2581 gcacatgagc ttatagtcgg gccaggcagc ctcgtctggt atcggctcca ggttatcggg
2641 agtacagtta atctccacgt cgcttgaggt gacgtgtcgc tcaacggggc gaagttgaac
2701 acgctctccg tgggtgccgg gtcgcaggcg gtaccacccg aaactggtaa aattttcatt
2761 gtccaacaac agccgcgtgg tcacgtccac gctcccctcg aattttgtaa tctccgggtg
2821 aaagttgtcg cagatgaacc ctcccaggcg gctgctggag gcagatactc tatagtagag
2881 agctggctta gatccaaagt agtacagcgt cgtgtggcac acggtctcca ctttgaagca
2941 gtccgcagac acgtgctttc cgccccacca tcccccgccg ctgccgccgc tctgtttgcc
3001 gccgttgcca tttcccaggg ccgcgctcaa agccgagctg tgcgcgcagt ccaccattgc
3061 gcgcacgagt tctgcctcgg tggttattcc acaagcgcta tccacctccg cctttgccat
3121 gtaaaaataa tggcgcacac catagacgtg aaccgcgact cgctttccac actcgctcat
3181 tcccagcagt gttaccacag acccgcttgg gcgggatagc tcagcaaacc tggatgggtc
3241 atcgtgtgag gcgctctccg aagtctctac tatgtcgtac acgtgaaatc tctcaaatct
3301 ggggttgaat ccatcgcccc gaaaatcctg gccgttccaa acccgaatcc tgcgaggcca
3361 gcaacctccg gaggcaaagt tcagcacgtc gtactctgag ccatcgcagt acactttggg
3421 tgggcgctcc aaggtgccca cgtgtacacc gcgtcgctgg tcggcggggg cttcttcatc
3481 gaggcatctt ggagctataa acttaaagct acccacctct gtgcagtacg agtgttgggg
3541 gggccttggg cgctctgtct ccgcggtctg cccgcttccc ggcctgaaaa atggcctctt
3601 gccaataaac ggattaaaaa acccgctcct gcgaacggag ttggcctgtt cgcgcgccgc
3661 cat

EHV-1 DNA polymerase (YP_053075.1) encoded by NC_001491 (1220aa) (SEQ ID NO:6)

MAAREQANSVRRSGFFNPFIGKRPFFRPGSGQTAETERPRPPQH
SYCTEVGSFKFIAPRCLDEEAPADQRRGVHVGTLERPPKVYCDGSEYDVLNFASGGCW
PRRIRVWNGQDFRGDGFNPRFERFHVYDIVETSESASHDDPSRFAELSRPSGSVVTLL
GMSECGKRVAVHVYGVRHYFYMAKAEVDSACGITTEAELVRAMVDCAHSSALSAALGN
GNGGKQSGGSGGGWWGGKHVSADCFKVETVCHTTLYYFGSKPALYYRVSASSSRLGGF
ICDNFHPEITKFEGSVDVTTRLLLDNENFTSFGWYRLRPGTHGERVQLRPVERHVTSS
DVEINCTPDNLEPIPDEAAWPDYKLMCFDIECKAGTGNEMAFPVATNQEDLVIQISCL
LYSLATQNHEHTLLFSLGSCDISEEYSFACVQRGEPRPTVLEFDSEYELLVAFLTFLK
QYSPEFATGYNIVNFDWAYIVNKVTSVYNIKLDGYGKFNKGGLFKVWDIATNHFQKKS
KVKINGLISLDMYSVATEKLKLPSYKLDAVVGDVLGEHKIDLPYKEIPSYYAGGPDRR
GVIGEYCIQDSRLVGKLFFKYLPHLELSAVAKLARITLTRVIFDGQQIRVYTCLLKLA
RERNFILPDNRRRFDSQADAASETSELAMDSQSHAFDSTDEPDGVDGTPDAAGSGATS
ENGGGKPGVGRAVGYQGAKVLDPVSGFHVDPVVVFDFASLYPSIIQAHNLCFTTLALD
EVDLAGLQPSVDYSTFEVGDQKLFFVHAHIRESLLGILLRDWLAMRKAVRARIPTSTP
EEAVLLDKQQSAIKVICNSVYGFTGVANGLLPCLRIAATVTTIGRDMLLKTRDYVHSR
WATRELLEDNFPGAIGFRNHKPYSVRVIYGDTDSVFIKFVGLTYEGVSELGDAMSRQI
SADLFRAPIKLECEKTFQRLLLITKKKYIGVINGGKMLMKGVDLVRKNNCSFINLYAR
HLVDLLLYDEDVATAAAEVTDVPPAEWVGRPLPSGFDKFGRVLVEAYNRITAPNLDVR
EFVMTAELSRSPESYTNKRLPHLTVYFKLAMRNEELPSVKERIPYVIVAQTEAAEREA
GVVNSMRGTAQNPVVTKTARPQPKRKLLVSDLAEDPTYVSENDVPLNTDYYFSHLLGT
ISVTFKALFGNDVRTTENLLKRFIPETPHKTPTKTQALLERAGFEKLTPFTPEEESRR
ILHTVFCTLEAAPHQS

EHV-1 glycoprotein (gC) gene (AY464052) from EHV-1 V592 strain (SEQ ID NO:7)

Atgtggttgcctaatctcgtgagatttgtggcggtcgcgtatctaatctgtgccggggcgatattaactta
tgcctctggagctagtgctagctccagccagagtacgcccgctacaccaactcacacaactccgaatctaa
ctaccgcacacggcgcgggctctgacaacacaactaacgcaaacggtacagaatctacacactcccatgaa
accacaatcacctgcaccaagagtctcatatctgtgccctactacaaatctgtcgatatgaactgtacaac
gtcggtaggcgtaaattatagcgagtaccgcctcgagatttacttgaaccagcgcaccccattttcgggta Figure 16 (Continued)

cgcccccggcgacgaagaaaactacatcaaccataacgccaccaaggatcagactctgctgttattctca
acggcagagaggaaaaaatctcgaaggggtggccagctgggagttatcccagacaggctaccaaagcgcca
gctgtttaaccttcccctccacacggaaggtggtacaaagtttccactgaccatcaaatctgtagattggc
ggacggccggcatttacgtgtggtccttgtatgccaaaaatggcacgctcgttaacagtaccagcgttacc
gtctcaacctacaacgcaccgttgctggacctttccgttcacccgagcctgaaggggaaaactacagggc
cacgtgcgtcgtcgcaagctactttccacacagctccgtcaagctgcggtggtacaaaaatgcccgcgagg
tggactttacaaagtacgttacgaacgcctcaagcgtgtgggtagacgggctaatcacgcgaatctctacg
gtgtctatcccggttgatccggaggaggaatacacacccagtcttcgctgtagcatagactggtacaggga
cgaagtatcatttgctcgcatagccaaagctggaacaccctctgtgtttgttgccccaaccgtgtccgttt
cggtagaagacggagacgccgtctgtacggctaaatgcgtaccgagcaccggggtgttcgtatcgtggtca
gtgaacgaccacctaccaggggttccgtcgcaagacatgacaaccggagtctgccctagccactcgggatt
ggttaacatgcaaagccgccggcccctctcagaagagaatggggagagggagtatagctgcataatagagg
ggtaccccgacggcctgcctatgttttcggacacagtggtatatgacgcctccccgattgttgaggacagg
ccggttttgacgagcatcatcgcagttacttgcggggccgcggcactggcgctggtcgttctcatcacagc
cgtttgtttttactgctccaagccctcacaggcgccgtacaagaagtctgactttag

EHV-1 glycoprotein (gC) protein (AAS45900.1) encoded by AY464052 from EHV-1 V592 strain (468aa) (SEQ ID NO:8)

MWLPNLVRFVAVAYLICAGAILTYASGASASSSQSTPATPTHTT
PNLTTAHGAGSDNTTNANGTESTHSHETTITCTKSLISVPYYKSVDMNCTTSVGVNYS
EYRLEIYLNQRTPFSGTPPGDEENYINHNATKDQTLLLFSTAERKKSRRGGQLGVIPD
RLPKRQLFNLPLHTEGGTKFPLTIKSVDWRTAGIYVWSLYAKNGTLVNSTSVTVSTYN
APLLDLSVHPSLKGENYRATCVVASYFPHSSVKLRWYKNAREVDFTKYVTNASSVWVD
GLITRISTVSIPVDPEEEYTPSLRCSIDWYRDEVSFARIAKAGTPSVFVAPTVSVSVE
DGDAVCTAKCVPSTGVFVSWSVNDHLPGVPSQDMTTGVCPSHSGLVNMQSRRPLSEEN
GEREYSCIIEGYPDGLPMFSDTVVYDASPIVEDRPVLTSIIAVTCGAAALALVVLITA
VCFYCSKPSQAPYKKSDF

EHV-1 glycoprotein (gC) gene (AY665713) from EHV-1 Ab4 strain (SEQ ID NO:9)

Atgtggttgcctaatctcgtgagatttgtggcggtcgcgtatctaatctgtgccggggc
gatattaacttatgcctctggagctagtgctagctccagccagagtacgcccgctacac
caactcacacaactccgaatctaactaccgcacacggcgcgggctctgacaacacaact
aacgcaaacggtacagaatctacacactcccatgaaaccacaatcacctgcaccaagag
tctcatatctgtgccctactacaaatctgtcgatatgaactgtacaacgtcggtaggcg
taaattatagcgagtaccgcctcgagatttacttgaaccagcgcaccccatttcgggt
acgcccccggcgacgaagaaaactacatcaaccataacgccaccaaggatcagactct
gctgttattctcaacggcagagaggaaaaaatctcgaaggggtggccagctgggagtta
tcccagacaggctaccaaagcgccagctgtttaaccttcccctccacacggaaggtggt
acaaagtttccactgaccatcaaatctgtagattggcggacggccggcatttacgtgtg
gtccttgtatgccaaaaatggcacgctcgttaacagtaccagcgttaccgtctcaacct
acaacgcaccgttgctggacctttccgttcacccgagcctgaaggggaaaactacagg
gccacgtgcgtcgtcgcaagctactttccacacagctccgtcaagctgcggtggtacaa
aaatgcccgcgaggtggactttacaaagtacgttacgaacgcctcaagcgtgtgggtag
acgggctaatcacgcgaatctctacggtgtctatcccggttgatccggaggaggaatac
acacccagtcttcgctgtagcatagactggtacagggacgaagtatcatttgctcgcat Figure 16 (Continued)

agccaaagctggaacaccctctgtgtttgttgccccaaccgtgtccgtttcggtagaag
acggagacgccgtctgtacggctaaatgcgtaccgagcaccggggtgttcgtatcgtgg
tcagtgaacgaccacctaccaggggttccgtcgcaagacatgacaaccggagtctgccc
tagccactcgggattggttaacatgcaaagccgccggcccctctcagaagagaatgggg
agagggagtatagctgcataatagaggggtaccccgacggcctgcctatgttttcggac
acagtggtatatgacgcctccccgattgttgaggacaggccggttttgacgagcatcat
cgcagttacttgcggggccgcggcactggcgctggtcgttctcatcacagccgtctgtt
tttactgctccaagccctcacaggcgccgtacaagaagtctgacttttag

EHV-1 glycoprotein (gC) protein (AAT67273.1) encoded by AY665713) from EHV-1 Ab4 strain (468aa) (SEQ ID NO:10)

MWLPNLVRFVAVAYLICAGAILTYASGASASSSQSTPATPTHTT
PNLTTAHGAGSDNTTNANGTESTHSHETTITCTKSLISVPYYKSVDMNCTTSVGVNYS
EYRLEIYLNQRTPFSGTPPGDEENYINHNATKDQTLLLFSTAERKKSRRGGQLGVIPD
RLPKRQLFNLPLHTEGGTKFPLTIKSVDWRTAGIYVWSLYAKNGTLVNSTSVTVSTYN
APLLDLSVHPSLKGENYRATCVVASYFPHSSVKLRWYKNAREVDFTKYVTNASSVWVD
GLITRISTVSIPVDPEEEYTPSLRCSIDWYRDEVSFARIAKAGTPSVFVAPTVSVSVE
DGDAVCTAKCVPSTGVFVSWSVNDHLPGVPSQDMTTGVCPSHSGLVNMQSRRPLSEEN
GEREYSCIIEGYPDGLPMFSDTVVYDASPIVEDRPVLTSIIAVTCGAAALALVVLITA
VCFYCSKPSQAPYKKSDF

EHV-1 glycoprotein (gC) gene (NC_001491) from EHV-1 (SEQ ID NO:11)

atgtggttgcctaatctcgtgagatttgtggcggtcgcgtatctaatctgtgccggggcgatattaactta
tgcctctggagctagtgctagctccagccagagtacgcccgctacaccaactcacacaactccgaatctaa
ctaccgcacacggcgcgggctctgacaacacaactaacgcaaacggtacagaatctacacactcccatgaa
accacaatcacctgcaccaagagtctcatatctgtgccctactacaaatctgtcgatatgaactgtacaac
gtcggtaggcgtaaattatagcgagtaccgcctcgagatttacttgaaccagcgcaccccattttcgggta
cgcccccggcgacgaagaaaactacatcaaccataacgccaccaaggatcagactctgctgttattctca
acggcagagaggaaaaaatctcgaaggggtggccagctgggagttatcccagacaggctaccaaagcgcca
gctgtttaaccttcccctccacacggaaggtggtacaaagtttccactgaccatcaaatctgtagattggc
ggacggccggcatttacgtgtggtccttgtatgccaaaaatggcacgctcgttaacagtaccagcgttacc
gtctcaacctacaacgcaccgttgctggacctttccgttcacccgagcctgaagggggaaaactacagggc
cacgtgcgtcgtcgcaagctactttccacacagctccgtcaagctgcggtggtacaaaaatgcccgcgagg
tggactttacaaagtacgttacgaacgcctcaagcgtgtgggtagacgggctaatcacgcgaatctctacg
gtgtctatcccggttgatccggaggaggaatacacacccagtcttcgctgtagcatagactggtacaggga
cgaagtatcatttgctcgcatagccaaagctggaacaccctctgtgtttgttgccccaaccgtgtccgttt
cggtagaagacggagacgccgtctgtacggctaaatgcgtaccgagcaccggggtgttcgtatcgtggtca
gtgaacgaccacctaccaggggttccgtcgcaagacatgacaaccggagtctgccctagccactcgggatt
ggttaacatgcaaagccgccggcccctctcagaagagaatggggagagggagtatagctgcataatagagg
ggtaccccgacggcctgcctatgttttcggacacagtggtatatgacgcctccccgattgttgaggacagg
ccggttttgacgagcatcatcgcagttacttgcggggccgcggcactggcgctggtcgttctcatcacagc
cgtctgtttttactgctccaagccctcacaggcgccgtacaagaagtctgacttttag Figure 16 (Continued)

EHV-1 glycoprotein (gC) protein (YP_053061.1) encoded by NC_001491 (468aa) (SEQ ID NO:12)

MWLPNLVRFVAVAYLICAGAILTYASGASASSSQSTPATPTHTT
PNLTTAHGAGSDNTTNANGTESTHSHETTITCTKSLISVPYYKSVDMNCTTSVGVNYS
EYRLEIYLNQRTPFSGTPPGDEENYINHNATKDQTLLLFSTAERKKSRRGGQLGVIPD
RLPKRQLFNLPLHTEGGTKFPLTIKSVDWRTAGIYVWSLYAKNGTLVNSTSVTVSTYN
APLLDLSVHPSLKGENYRATCVVASYFPHSSVKLRWYKNAREVDFTKYVTNASSVWVD
GLITRISTVSIPVDPEEEYTPSLRCSIDWYRDEVSFARIAKAGTPSVFVAPTVSVSVE
DGDAVCTAKCVPSTGVFVSWSVNDHLPGVPSQDMTTGVCPSHSGLVNMQSRRPLSEEN
GEREYSCIIEGYPDGLPMFSDTVVYDASPIVEDRPVLTSIIAVTCGAAALALVVLITA
VCFYCSKPSQAPYKKSDF

EHV-1 RacL DNA polymerase partial sequence (SEQ ID NO:13)

FDSQADAASETSELAMDSQSHAFDSTDEPDGVDGTPDAAGSGATSENGGGKPGVGRAVGYQGAKVLDPVSG
FHVDPVVVFDFASLYPSIIQAHNLCFTTLALDEVDLAGLQPSVDYSTFEVGDQKLFFVHAHIRESLLGILL
RDWLAMRKAVRARIPTSTPEEAVLLDKQQSAIKVICNSVYGFTGVANGLLPCL

EHV-1 RacL DNA polymerase partial sequence comprising N at 752 of full length EHV-1 DNA polymerase (SEQ ID NO:14)

FDSQADAASETSELAMDSQSHAFDSTDEPDGVDGTPDAAGSGATSENGGGKPGVGRAVGYQGAKVLDPVSG
FHVDPVVVFDFASLYPSIIQAHNLCFTTLALDEVDLAGLQPSVNYSTFEVGDQKLFFVHAHIRESLLGILL
RDWLAMRKAVRARIPTSTPEEAVLLDKQQSAIKVICNSVYGFTGVANGLLPCL

EHV-1 RacL DNA polymerase partial sequence with amino acid deletion at 752 of full length EHV-1 DNA polymerase (SEQ ID NO:15)

FDSQADAASETSELAMDSQSHAFDSTDEPDGVDGTPDAAGSGATSENGGGKPGVGRAVGYQGAKVLDPVSG
FHVDPVVVFDFASLYPSIIQAHNLCFTTLALDEVDLAGLQPSVYSTFEVGDQKLFFVHAHIRESLLGILLR
DWLAMRKAVRARIPTSTPEEAVLLDKQQSAIKVICNSVYGFTGVANGLLPCL

EHV-1 glycoprotein (gC) gene from EHV-1 RacL11 strain (SEQ ID NO:34)

Atgtggttgcctaatctcgtgagatttgtggcggtcgcgtatctaatctgtgccggggcgatattaactta
tgcctctggagctagtgctagctccagccagagtacgcccgctacaccaactcacacaactccgaatctaa
ctaccgcacacggcgcgggctctgacaacacaactaacgcaaacggtacagaatctacacactcccatgaa
accacaatcacctgcaccaagagtctcatatctgtgccctactacaaatctgtcgatatgaactgtacaac
gtcggtaggcgtaaattatagcgagtaccgcctcgagatttacttgaaccagcgcaccccatttcgggta
cgcccccggcgacgaagaaaactacatcaaccataacgccaccaaggatcagactctgctgttattctca
acggcaaagaggaaaaatctcgaaggggtggccagctgggagttatcccagacaggctaccaaagcgcaa
gctgtttaaccttcccctccacacggaaggtggtacaaagtttccactgaccatcaaatctgtagattggc
ggacggccggcatttacgtgtggtccttgtatgccaaaaatggcacgctcgttaacagtaccagcgttacc
gtctcaacctacaacgcaccgttgctggacctttccgttcacccgagcctgaaggggaaaactacagggc
cacgtgcgtcgtcgcaagctactttccacacagctccgtcaagctgcggtggtacaaaaatgcccgcgagg
tggactttacaaagtacgttacgaacgcctcaagcgtgtgggcagacgggctaatcacgcgaatctctacg
gtgtctatcccggttggtccggaggaggaatacacacccagtcttcgctgtagcatagactggtacaggga
cgaagtatcatttgctcgcatagccaaagctggaacaccctctgtgtttgttgccccaaccgtgtccgttt
cggtagaagacggagacgccgtctgtacggctaaatgcgtaccgagcaccggggtgttcgtatcgtggtca
gtgaacgaccacctaccaggggttccgtcgcaagacatgacaaccggagtctgccctagccactcgggatt Figure 16 (Continued)

ggttaacatgcaaagccgccggcccctctcagaagagaatggggagagggagtatagctgcataatagagg
ggtaccccgacggcctgcctatgttttcggacacagtggtatatgacgcctccccgattgttgaggacagg
ccggttttgacgagcatcatcgcagttacttgcggggccgcggcactggcgctggtcgttctcatcacagc
cgtctgtttttactgctccaagccctcacaggcgccgtacaagaagtctgacttttag

EHV-1 glycoprotein (gC) protein from EHV-1 RacL11 strain (SEQ ID NO:35)
MWLPNLVRFVAVAYLICAGAILTYASGASASSSQSTPATPTHTTPNLTTAHGAGSDNTTNANGTESTHSHE
TTITCTKSLISVPYYKSVDMNCTTSVGVNYSEYRLEIYLNQRTPFSGTPPGDEENYINHNATKDQTLLLFS
TAKRKKSRRGGQLGVIPDRLPKRKLFNLPLHTEGGTKFPLTIKSVDWRTAGIYVWSLYAKNGTLVNSTSVT
VSTYNAPLLDLSVHPSLKGENYRATCVVASYFPHSSVKLRWYKNAREVDFTKYVTNASSVWADGLITRIST
VSIPVGPEEEYTPSLRCSIDWYRDEVSFARIAKAGTPSVFVAPTVSVSVEDGDAVCTAKCVPSTGVFVSWS
VNDHLPGVPSQDMTTGVCPSHSGLVNMQSRRPLSEENGEREYSCIIEGYPDGLPMFSDTVVYDASPIVEDR
PVLTSIIAVTCGAAALALVVLITAVCFYCSKPSQAPYKKSDF*

EHV-1 DNA polymerase (Pol) from EHV-1 NY03 strain (SEQ ID NO:36)
atggcggcgcgcgaacaggccaactccgttcgcaggagcgggtttttaatccgtttattggcaagaggccatttttcaggccgg
gaagcgggcagaccgcggagacagagcgcccaaggccccccaacactcgtactgcacagaggtgggtagctttaagtttat
agctccaagatgcctcgatgaagaagcccccgccgaccagcgacgcggtgtacacgtgggcaccttggagcgcccacccaa
agtgtactgcgatggctcagagtacgacgtgctgaactttgcctccggaggttgctggcctcgcaggattcgggtttggaacggc
caggattttcggggcgatggattcaaccccagatttgagagatttcacgtgtacgacatagtagagacttcggagagcgcctcac
acgatgacccatccaggtttgctgagctatcccgcccaagcgggtctgtggtaacactgctgggaatgagcgagtgtggaaagc
gagtcgcggttcacgtctatggtgtgcgccattatttttacatggcaaaggcggaggtggatagcgcttgtggaataaccaccga
ggcagaactcgtgcgcgcaatggtggactgcgcgcacagctcggctttgagcgcggccctgggaaatggcaacggcggcaa
acagagcggcggcagcggcgggggatggtggggcggaaagcacgtgtctgcggactgcttcaaagtggagaccgtgtgcc
acacgacgctgtactactttggatctaagccagctctctactatagagtatctgcctccagcagccgcctgggagggttcatctgc
gacaactttcacccggagattacaaaattcgaggggagcgtggacgtgaccacgcggctgttgttggacaatgaaaattttacca
gtttcgggtggtaccgcctgcgacccggcacccacggagagcgtgttcaacttcgccccgttgagcgacacgtcacctcaagc
gacgtggagattaactgtactcccgataacctggagccgataccagacgaggctgcctggcccgactataagctcatgtgctttg
atatagagtgtaaagctggaacgggtaacgaaatggcgttcccagtggcaactaaccaagaggacctggtcatccagatctcct
gtctgctgtactcgcttgctactcagaaccacgaacacaccctgctgttttccctcgggtcatgcgatatctctgaggaatactcgtt
tgcatgcgtccagcgcggcgagcccagaccgacggttttggagtttgacagcgagtacgagctgctggttgccttcctgacctt
ctcaagcagtactctcccgagttcgccaccggctacaacatcgttaattttgactgggcgtacatagttaacaaggtaacgtcggt
gtataacatcaagctggacgggtacggcaagttcaacaaaggggggctgtttaaggtgtgggacatcgccacgaaccattttca
gaagaagagcaaggtgaaaatcaatggcctgatatctctagacatgtattctgtggcgacggaaaagctaaagctacccagcta
caaactcgacgcggtcgtgggagacgtcctcggcgagcataagatagaccttccctataaagaaataccctcctattacgcggg
agggcctgaccggagggggcgtaataggagagtattgtatccaggactctaggctggtgggcaagctgtttttaagtacctcccc
catctggaactatcggcggtggccaaactcgcccgtatcaccctaacgcgggtaattttgacggtcagcaaattcgcgtgtaca
cgtgcttgctgaaactcgcccgcgagagaaatttcattttgccagacaacagacgccggtttgacagtcaggcagacgccgcgt
cagagacttcggagttggctatggatagccaaagccacgccttcgacagtacagacgaacccgacggtgtggacggtacccc
ggacgccgcaggatctggcgctacttctgaaaacggaggcgggaagcccggcgtcgggagggccgtgggctaccagggag
caaaggttctagaccccgtatccggctttcatgtggaccccgtggttgtgtttgacttcgctagcttatacccaagcattatccaggc
ccataacctctgtttcaccaccctggcgctcgatgaagtggatctggccgggcttcaaccatccgtcaactactcgacgttcgagg Figure 16 (Continued)

tgggtgaccaaaagttatttttgtccacgcccatattcgcgaaagcctgcttggcatcttgctgcgcgactggctggccatgcgaa
aggcggtgagggcgcgaatccccaccagcacccccgaggaggcagttttactagataagcagcagtctgcgattaaggtgata
tgcaactcggtttacggattcacgggggtggcaaacggcctgttgccgtgtctgaggatagcggctaccgttaccacgatagga
cgcgacatgctcctcaagacccgagattacgttcactctcgttgggcgacgcgcgagctgctggaggacaattttccaggggct
ataggtttccgaaaccacaagccttactccgtcagggttatctacggagacaccgactccgtgtttatcaagtttgtgggcctgacg
tacgagggggtatcggagctgggggatgctatgtcgcgtcagatttcagcggacctctttagagcgcccatcaaactggagtgt
gagaagacctttcagcgactgctgctgatcaccaagaagaagtacataggtgtcataaacgggggaagatgctcatgaaggg
ggtcgacctggtccgcaaaaataactgctctttcataaacttgtacgcgcgacatctggtagatcttttgttgtacgacgaggatgtg
gccacggcggcagcagaggtgacagacgtgcctcccgcagaatgggtggggcgcccgctaccgagcggctttgacaagttt
gggcgagtgctggtagaggcgtacaaccgtatcactgcccccaacttggacgtgcgcgagttcgttatgactgctgagctgagc
cgctcacccgaattgtataccaacaagcgcctgccgcacctcaccgtctactttaagctcgccatgaggaatgaagaactgccca
gcgtaaaagagagaattccgtatgtgatagttgcgcagaccgaggccgcggaacgcgaagcgggtgtagtaaactcaatgcg
cggtaccgcccaaaaccccgtggtaaccaagaccgcacgcccccaacctaaacgcaaactgctggtttccgacctcgccgaa
gacccgacctatgtttccgagaatgacgtaccgctaaacacagactactatttctcccacctgttgggtaccataagcgtgacctttt
aaggctctattcggaaatgatgtgagaacaacagaaaatcttttaaagcggtttattccggaaaccccccacaagacccccacga
aaacccaggcactgcttgagcgcgccggctttgaaaagctgacgccctttacaccggaggaagaaagtcgtcgaatactgcat
acagtttttgtactctagaagcagctccccatcaaagctga

EHV-1 DNA polymerase (pol) protein from EHV-1 NY03 strain (SEQ ID NO:37)
maareqansvrrsgffnpfigkrpffrpgsgqtaeterprppqhsyctevgsfkfiaprcldeeapadqrrgvhvgtlerppk
vycdgseydvlnfasggcwprrirvwngqdfrgdgfnprferfhvydivetsesashddpsrfaelsrpsgsvvtllgmsec
gkrvavhvygvrhyfymakaevdsacgitteaelvramvdcahssalsaalgngnggkqsggsgggwwggkhvsadc
fkvetvchttlyyfgskpalyyrvsasssrlggficdnfhpeitkfegsvdvttrllldnenftsfgwyrlrpgthgervqlrpver
hvtssdveinctpdnlepipdeaawpdyklmcfdieckagtgnemafpvatnqedlviqiscllyslatqnhehtllfslgsc
diseeysfacvqrgeprptvlefdseyellvafltflkqyspefatgynivnfdwayivnkvtsvynikldgygkfnkgglfkv
wdiatnhfqkkskvkinglisldmysvateklklpsykldavvgdvlgehkidlpykeipsyyaggpdrrgvigeyciqds
rlvgklffkylphlelsavaklaritltrvifdgqqirvytcllklarernfilpdnrrrfdsqadaasetselamdsqshafdstdep
dgvdgtpdaagsgatsengggkpgvgravgyqgakvldpvsgfhvdpvvvfdfaslypsiiqahnlcfttlaldevdlagl
qpsvnystfevgdqklffvhahiresllgillrdwlamrkavrariptstpeeavlldkqqsaikvicnsvygftgvangllpclr
iaatvttigrdmllktrdyvhsrwatrellednfpgaigfrnhkpysvrviygdtdsvfikfvgltyegvselgdamsrqisadl
frapiklecektfqrlllitkkkyigvinggkmlmkgvdlvrknncsfinlyarhlvdlllydedvataaaevtdvppaewvg
rplpsgfdkfgrvlveaynritapnldvrefvmtaelsrspelytnkrlphltvyfklamrneelpsvkeripyvivaqteaaer
eagvvnsmrgtaqnpvvtktarpqpkrkllvsdlaedptyvsendvplntdyyfshllgtisvtfkalfgndvrttenllkrfip
etphktptktqalleragfekltpftpeeesrrilhtvfctleaaphqs

RECOMBINANT EQUINE HERPESVIRUS-1 VACCINE CONTAINING MUTATED GLYCOPROTEIN C AND USES THEREOF

CROSS-REFERENCE TO RELATED APPLICATIONS

This application is a continuation application of U.S. application Ser. No. 13/840,935 filed on Mar. 15, 2013, which claims benefit of U.S. provisional application Ser. No. 61/613,151 filed Mar. 20, 2012.

FIELD OF THE INVENTION

The present invention relates to compositions or vaccines for combating equine herpesvirus infections in animals. Specifically, the present invention provides compositions or vaccines that contain a recombinant EHV-1 that elicit an immune response in animals against equine herpesvirus, including compositions comprising said recombinant EHV-1, methods of vaccination against equine herpesvirus, and kits for use with such methods and compositions.

BACKGROUND OF THE INVENTION

Equine Herpesvirus type 1 (EHV-1) is one of the most important and prevalent pathogens of equine populations worldwide (Ma et al., J. of General Virology 91, 1817-1822, 2010). Together with its close relatives varicella-zoster virus, bovine Herpesvirus type 1, pseudorabies virus and EHV-4, EHV-1 forms the genus *Varicellovirus* in the subfamily Alphaherpesvirinae of the family Herpesviridae of the order Herpesvirales (Davison et al., The order Herpesvirales. Arch Virol 154, 171-177, 2009). Diseases caused by EHV-1 range from mild rhinopneumonitis and abortion in pregnant mares to neurological disease that is frequently lethal in affected horses (Allen et al., Prog Vet Microbiol Immunol 2, 78-144, 1986; Carroll et al., Aust Vet J 62, 345-346, 1985; Crabb et al., Adv Virus Res 45, 153-190, 1995). The pathogenesis of EHV infection is very complex. Natural infection occurs through inhalation or ingestion of the infectious virus. Within a few days of the virus can be found in leucocytes, where it is protected from recognition and attacks by the immune system. The virus disseminates via cell-associated viremia to secondary sites of replication (Allen et al., Proceedings $8^{th}$ Equine Infectious Disease Conference, Dubai 23-26, pp 129-146, 1998).

EHV-1 harbors a 150 kb double-stranded DNA genome that is highly conserved among strains. A neuropathogenic strain Ab4 (GenBank accession No. AY665713) and a nonneuropathogenic strain V592 (GenBank accession No. AY464052) were extensively characterized and showed a nucleotide variation rate of approximately 0.1% (Nugent et al., J. Virol 80, 4047-4060, 2006). It was found that only a minority of EHV-1 strains are capable of inducing neurological disorders, although all strains can cause respiratory disease and abortion (Mumford et al., J. Reprod Fertil Suppl 35, 509-518, 1987; Ostlund, Vet Clin North Am Equine Pract 9, 283-294, 1993; Wilson, Vet Clin North Am Equine Pract 13, 53-72, 1997). Recently, epidemiological as well as reverse-genetic studies have shown that a single-nucleotide polymorphism at position 2254 (G/A2254) of open reading frame 30 (ORF30), encoding viral DNA polymerase (Pol), will lead to a variation at the amino acid position 752 (D/N752), which is associated with the virus's neuropathogenic potential (Goodman et al., J Biol Chem 281, 18193-18200, 2007; Van de Walle et al., J. Infect Dis 200, 20-25, 2009; Smith et al., Vet. Microbiol., 141, 5-11, 2010). It has been shown that residue 752 in the essential Pol of EHV-1 is not required for virus growth and that the N752 mutation confers a drug-sensitive phenotype to the virus (Ma et al., 2010).

Glycoprotein C (gC) of EHV-1 was shown to play important role in the early steps of infection and in release of virions (Osterrieder, Virus Research 2, 165, 1999). Glycoprotein C of EHV-1 is non-essential for virus growth. It mediates primary attachment, and is required for efficient virus replication in primary equine cells (Osterrieder, 1999).

Conventional killed vaccines provide only partial clinical and virological protection against respiratory infections, but do not prevent cell-associated viremia. Considering the susceptibility of animals, including humans, to herpesvirus, a means of preventing herpesvirus infection and protecting animals is essential. Accordingly, there is a need for an effective vaccine against herpesvirus.

Citation or identification of any document in this application is not an admission that such document is available as prior art to the present invention.

SUMMARY OF THE INVENTION

The invention provides a composition or vaccine that contains a recombinant Equine Herpesvirus-1 (EHV-1). In particular, the present invention provides a recombinant EHV-1 that contains a mutated Glycoprotein C (gC) gene that is non-functional. The gC gene of the recombinant EHV-1 may be deleted. The gC gene may encode a mutated gC protein wherein the N-terminal region of the gC protein is deleted. The recombinant EHV-1 may further comprise a DNA polymerase (Pol) gene encoding a Pol having an asparagine (N) at the amino acid position 752. The recombinant EHV-1 may comprise a DNA polymerase (Pol) gene encoding a Pol having an asparagine (N) at the amino acid position 752. The EHV-1 may be EHV-1 RacL strain.

The invention provides methods for inducing an immunogenic or protective response against EHV-1, as well as methods for preventing EHV-1 or disease state(s) caused by EHV-1, comprising administering the composition or vaccine of the present invention. The invention also provides methods of vaccinating an animal comprising at least one administration of the composition or recombinant EHV-1.

These and other embodiments are disclosed or are obvious from and encompassed by, the following Detailed Description.

BRIEF DESCRIPTION OF DRAWINGS

The following detailed description, given by way of example, and which is not intended to limit the invention to specific embodiments described, may be understood in conjunction with the accompanying figures, incorporated herein by reference, in which:

FIG. 1 is the table showing the corresponding SEQ ID NO assigned to polynucleotide and protein sequences.

FIGS. 2A-2C depict the cloning scheme. FIG. 2D shows the amino acid mutation in EHV-1 polymerase.

FIGS. 3A-3B show the indirect immunofluorescence assay (IFA) of RK13-Pol and RK13.

FIGS. 4A-4B depict the growth of L11-_ΔPol EYFP in RK13-Pol v. L11-_ΔPol EYFP in RK13.

FIGS. 5A-5F depict the IFA of RacL11, L11_D752NΔgC and L11_D752NΔgC rev using anti-EHV-1 gC MAb.

FIGS. 11A-11B depict the serology against EHV-1 using the complement fixation (CF) and virus neutralization (VN) tests.

FIGS. 14A-14C show the polynucleotide and protein sequence alignments of EHV-1 DNA polymerase.

FIGS. 15A-15B show the polynucleotide and protein sequence alignments of EHV-1 glycoprotein C.

FIG. 16 shows the DNA and protein sequences.

DETAILED DESCRIPTION

Figures 2, 2C:
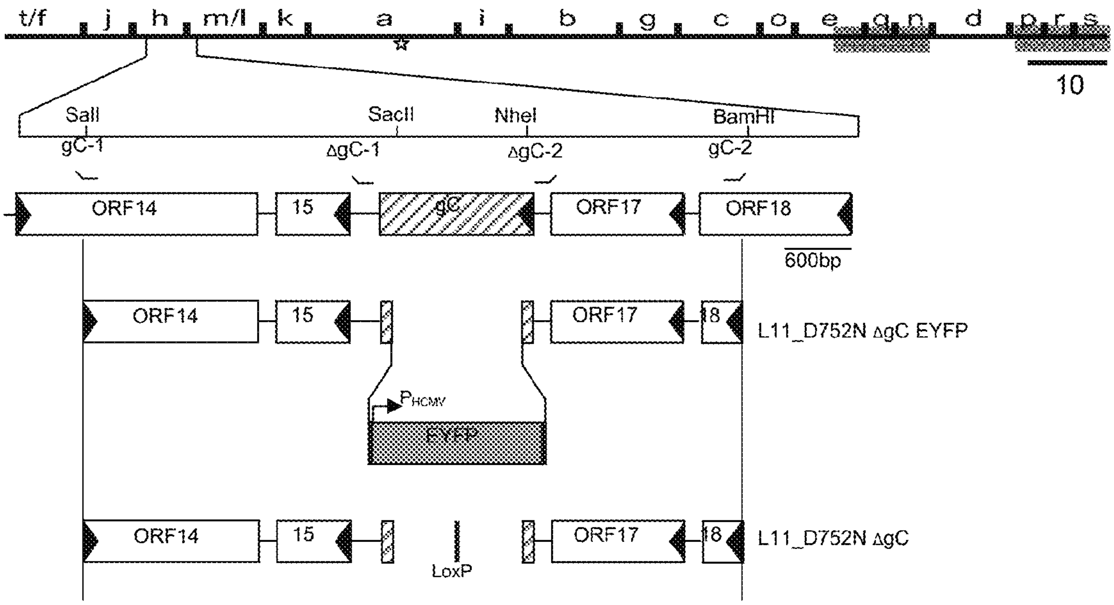

It is noted that in this disclosure and particularly in the claims, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a", "an", and "the" include plural referents unless context clearly indicates otherwise. Similarly, the word "or" is intended to include "and" unless the context clearly indicates otherwise. The word "or" means any one member of a particular list and also includes any combination of members of that list.

The term "EHV-1 N strain" as used herein refers to any EHV-1 strain which has an asparagine (N) at the amino acid position 752 of its DNA polymerase. The EHV-1 N strain may be wild-type strain that comprises a DNA polymerase comprising an asparagine (N) at the amino acid position 752. The EHV-1 N strain may be mutated or recombinant EHV-1 strain wherein the DNA polymerase is engineered to have an asparagine (N) at the amino acid position 752.

The term "EHV-1 D strain" as used herein refers to any EHV-1 strain which has an Aspartic acid (D) at the amino acid position 752 of its DNA polymerase. The EHV-1 D strain may be a wild-type strain that comprises a DNA polymerase comprising an aspartic acid (D) at the amino acid position 752. The EHV-1 D strain may be a mutated or recombinant EHV-1 strain wherein the DNA polymerase is engineered to have an aspartic acid (D) at the amino acid position 752.

By "animal" is intended mammals, human, birds, and the like. The animal may be selected from the group consisting of equine (e.g., horse, zebra, donkey), canine (e.g., dogs, wolves, foxes, coyotes, jackals), feline (e.g., lions, tigers, domestic cats, wild cats, other big cats, and other feline including cheetahs and lynx), ovine (e.g., sheep), bovine (e.g., cattle, cow, buffalo), swine (pig), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

The terms "polypeptide" and "protein" are used interchangeably herein to refer to a polymer of consecutive amino acid residues.

The term "nucleic acid", "nucleotide", and "polynucleotide" refers to RNA or DNA and derivatives thereof, such as those containing modified backbones. It should be appreciated that the invention provides polynucleotides comprising sequences complementary to those described herein. Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al.; Pandher K et al.; Chung J Y et al.), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

As used herein, the term "antigen" or "immunogen" means a substance that induces a specific immune response in a host animal. The antigen may comprise a whole organism, killed, attenuated or live; a subunit or portion of an organism; a recombinant vector containing an insert expressing an epitope, polypeptide, peptide, protein, or fragment thereof with immunogenic properties; a piece or fragment of nucleic acid capable of inducing an immune response upon presentation to a host animal; a protein, a polypeptide, a peptide, an epitope, a hapten, or any combination thereof. Alternately, the immunogen or antigen may comprise a toxin or antitoxin.

By definition, an epitope is an antigenic determinant that is immunologically active in the sense that once administered to the host, it is able to evoke an immune response of the humoral (B cells) and/or cellular type (T cells). These are particular chemical groups or peptide sequences on a molecule that are antigenic. An antibody specifically binds a particular antigenic epitope on a polypeptide. Specific, non-limiting examples of an epitope include a tetra- to penta-peptide sequence in a polypeptide, a tri- to penta-glycoside sequence in a polysaccharide. In the animal most antigens will present several or even many antigenic determinants simultaneously. Such a polypeptide may also be qualified as an immunogenic polypeptide and the epitope may be identified as described further.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a purified polypeptide preparation is one in which the polypeptide is more enriched than the polypeptide is in its natural environment. A polypeptide preparation is substantially purified such that the polypeptide represents several embodiments at least 60%, at least 70%, at least 80%, at least 90%, at least 95%, or at least 98%, of the total polypeptide content of the preparation. The same applies to polynucleotides. The polypeptides disclosed herein can be purified by any of the means known in the art.

The present invention provides a composition or vaccine comprising a recombinant viral vector Equine Herpesvirus-1 (EHV-1). In one aspect, the present invention provides a recombinant EHV-1 that comprises a mutated Glycoprotein C (gC) gene. In another aspect, the present invention provides a recombinant EHV-1 that comprises a DNA polymerase having an asparagine (N) at the amino acid position 752. In yet another aspect, the present invention provides a recombinant EHV-1 wherein the EHV-1 is an EHV-1 N strain. The recombinant EHV-1 N strain may comprise a mutated gC gene. In yet another aspect, the recombinant EHV-1 comprises a mutated gC gene and a DNA polymerase having an asparagine (N) at the amino acid position 752. The composition or vaccine of the present invention may further comprise a pharmaceutically or veterinary acceptable vehicle, diluent, adjuvant, or excipient.

The term "composition" comprises any vaccine or immunological composition, once it has been injected to a host, including canines, felines, equine and humans, that induces an immune response in the host, and/or protects the host from leukemia, and/or which may prevent implantation of the parasite, and/or which may prevent disease progression in infected subjects, and/or which may limit the diffusion of runaway parasites to internal organs. This may be accomplished upon vaccination according to the present invention through the induction of cytokine secretion, notably IFN-gamma secretion (as example of a method of measurement of IFN-gamma secretion, the Quantikine® immunoassay from R&D Systems Inc. (catalog number#CAIF00) could be used (Djoba Siawaya J F et al.)).

The present invention provides a recombinant EHV-1 comprising a DNA polymerase having an asparagine (N) at the amino acid position 752. Homologs of polypeptides of EHV-1 DNA polymerase are intended to be within the scope of the present invention. As used herein, the term "homologs" includes orthologs, analogs and paralogs. The tem "anologs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type polypeptide can differ from the wild-type polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type polypeptide or polynucleotide sequences, and will exhibit a similar function.

In one aspect of the present invention, the recombinant EHV-1 comprises an EHV-1 DNA polymerase comprising an asparagine (N) at the amino acid position 752 or equivalent position of a polypeptide having at least 70%, 75%, 80%, 85%, 90%, 95%, 96%, 97%, 98%, 99%, 99.1%, 99.2%, 99.3%, 99.4%, 99.5%, 99.6%, 99.7%, 99.8% or 99.9% sequence identity to SEQ ID NO: 2, 4, 6, 37, 13, 14, or 15. In another aspect, the present invention provides fragments and variants of the EHV-1 DNA polymerases, which may readily be prepared by one of skill in the art using well-known molecular biology techniques. Variants are homologous polypeptides having an amino acid sequence at least 75%, 80%, 85%, 90%, 95%, 96%, 97%, 98%, 99%, 99.1%, 99.2%, 99.3%, 99.4%, 99.5%, 99.6%, 99.7%, 99.8% or 99.9% identical to the amino acid sequence as set forth in SEQ ID NO: 2, 4, 6, 37, 13, 14, or 15. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the EHV-1 DNA polymerase primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein. The modifications may be any amino acid change at amino acid positions other than position 752 of SEQ ID NO: 2, 4, 6, 37, 13, 14, or 15.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

Procedures to determine fragments of polypeptide and epitope such as, generating overlapping peptide libraries (Hemmer B. et al.), Pepscan (Geysen H. M. et al., 1984; Geysen H. M. et al., 1985; Van der Zee R. et al.; Geysen H. M.) and algorithms (De Groot A. et al.; Hoop T. et al.; Parker K. et al.), can be used in the practice of the invention, without undue experimentation. Generally, antibodies specifically bind a particular antigenic epitope. Specific, non-limiting examples of epitopes include a tetra- to penta-peptide sequence in a polypeptide, a tri- to penta glycoside sequence in a polysaccharide. In animals most antigens will present several or even many antigenic determinants simultaneously. Preferably wherein the epitope is a protein fragment of a larger molecule it will have substantially the same immunological activity as the total protein.

In one aspect, the present invention provides a polynucleotide encoding an EHV-1 DNA polymerase comprising an asparagine (N) at the amino acid position 752 or an equivalent position of a polypeptide having at least 70%, 75%, 80%, 85%, 90%, 95%, 96%, 97%, 98%, 99%, 99.1%, 99.2%, 99.3%, 99.4%, 99.5%, 99.6%, 99.7%, 99.8% or 99.9% sequence identity to SEQ ID NO: 2, 4, 6, 37, 13, 14, or 15, or a conservative variant, an allelic variant, a homolog or an immunogenic fragment comprising at least eight or at east ten consecutive amino acids of one of these polypeptides, or a combination of these polypeptides.

In another aspect, the present invention provides a polynucleotide having a nucleotide sequence as set forth in SEQ ID NO: 1, 3, 5, or 36, or a variant thereof. In yet another aspect, the present invention provides a polynucleotide having at least 70%, 75%, 80%, 85%, 90%, 95%, 95%, 96%, 97%, 98%, 99%, 99.1%, 99.2%, 99.3%, 99.4%, 99.5%, 99.6%, 99.7%, 99.8% or 99.9% sequence identity to SEQ ID NO: 1, 3, 5 or 36, or a variant thereof.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for an EHV-1 DNA polymerase, the DNA sequence of the EHV-1 DNA polymerase gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of EHV-1 DNA polymerase in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the EHV-1 DNA polymerase encoded by the nucleotide sequence is functionally unchanged.

In one aspect, the present invention provides a recombinant EHV-1 that contains a mutated Glycoprotein C (gC) gene. The term "mutated gC gene" refers to the gC gene of EHV-1 that is altered or engineered which results in a non-functional gC protein upon expression. The alteration or engineering of the gC gene includes mutation or deletion of a segment of the gC gene which is essential for the expression of a functional gC protein. The deletion of the gC gene may be a deletion of the polynucleotides encoding the amino-terminal region of the gC protein. The deleted amino-terminal regions of the gC protein may be any length, for example, a region of 1-10 amino acids, or 11-20 amino acids, or 21-30 amino acids, or 31-40 amino acids, or 41-60 amino acids, or 61-90 amino acids, or 91-120 amino acids, or 121-160 amino acids. The term "mutated gC gene" also includes deletion of the entire gC gene of EHV-1 wherein gC protein is not expressed.

In one aspect, the present invention provides a recombinant EHV-1 wherein the Glycoprotein C (gC) gene in the native (wild-type) EHV-1 genome encoding the gC protein is deleted. The term "Glycoprotein C (gC) gene" includes any gene or polynucleotide that encodes the Glycoprotein C (gC) of EHV-1, and homologs, fragments or variants thereof. The gC gene may encode a gC protein having at least 75%, 80%, 85%, 90%, 95%, 95%, 96%, 97%, 98%, 99%, 99.1%, 99.2%, 99.3%, 99.4%, 99.5%, 99.6%, 99.7%, 99.8% or 99.9% sequence identity to SEQ ID NO: 8, 10, or 12, or a variant thereof. The gC gene having at least 75%, 80%, 85%, 90%, 95%, 95%, 96%, 97%, 98%, 99%, 99.1%, 99.2%, 99.3%, 99.4%, 99.5%, 99.6%, 99.7%, 99.8% or 99.9% sequence identity to SEQ ID NO:7, 9, or 11 is also encompassed in the present invention. In another aspect, the present invention provides a recombinant EHV-1 wherein the Glycoprotein C (gC) gene in the native (wild-type) EHV-1 genome encoding the gC protein is altered or engineered resulting in a mutated gC protein. In yet another aspect, the engineered gC gene encodes a mutated gC protein wherein the N-terminal region of the gC protein is deleted.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server), as well as in Altschul et al.; and thus, this document speaks of using the algorithm or the BLAST or BLASTX and BLOSUM62 matrix by the term "blasts".

Alternatively or additionally, the term "identity", for instance, with respect to a nucleotide or amino acid sequence, may indicate a quantitative measure of homology between two sequences. The percent sequence homology may be calculated as: $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}$=8; $N_{dif}$=2).

Alternatively or additionally, "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

Recombinant vectors disclosed herein may include a polynucleotide encoding a polypeptide, a variant thereof or a fragment thereof. Recombinant vectors may include plasmids and viral vectors and may be used for in vitro or in vivo expression. Recombinant vectors may include further a signal peptide. Signal peptides are short peptide chain (3-60 amino acids long) that direct the post-translational transport of a protein (which are synthesized in the cytosol) to certain organelles such as the nucleus, mitochondrial matrix, endoplasmic reticulum, chloroplast, apoplast and peroxisome. Typically, the naturally occurring EHV-1 proteins may be translated as precursors, having an N-terminal signal peptide sequence and a "mature" protein domain. The signal peptide may be cleaved EHV-1 protein or a peptide signal from a secreted protein e.g. the signal peptide from the tissue plasminogen activator protein (tPA), in particular the human tPA (S. Friezner Degen et al.; R. Rickles et al.; D. Berg. et al.), or the signal peptide from the Insulin-like growth factor 1 (IGF1), in particular the equine IGF1 (K. Otte et al.), the canine IGF1 (P. Delafontaine et al.), the feline IGF1 (WO03/022886), the bovine IGF1 (S. Lien et al.), the porcine IGF1 (M. Muller et al.), the chicken IGF1 (Y. Kajimoto et al.), the turkey IGF1 (GenBank accession number AF074980). The signal peptide from IGF1 may be natural or optimized which may be achieved by removing cryptic splice sites and/or by adapting the codon usage. Upon translation, the unprocessed polypeptide may be cleaved at a cleavage site to lead to the mature polypeptide. The cleavage site may be predicted using the method of Von Heijne (1986).

A plasmid may include a DNA transcription unit, for instance a nucleic acid sequence that permits it to replicate in a host cell, such as an origin of replication (prokaryotic or eukaryotic). A plasmid may also include one or more selectable marker genes and other genetic elements known in the art. Circular and linear forms of plasmids are encompassed in the present disclosure.

In a further aspect, the present invention relates to an in vivo expression vector comprising a polynucleotide sequence, which contains and expresses in vivo in a host the EHV-1 antigen, polypeptides and/or variants or fragments thereof.

The in vivo expression vector may include any transcription unit containing a polynucleotide or a gene of interest and those essential elements for its in vivo expression. These expression vectors may be plasmids or recombinant viral vectors. For in vivo expression, the promoter may be of viral or cellular origin. In one embodiment, the promoter may be the cytomegalovirus (CMV) early promoter (CMV-IE promoter), the SV40 virus early or late promoter or the Rous Sarcoma virus LTR promoter, a promoter of a cytoskeleton gene, such as the desmin promoter (Kwissa M. et al.), or the actin promoter (Miyazaki J. et al.). When several genes are present in the same plasmid, they may be provided in the same transcription unit or in different units.

As used herein, the term "plasmid" may include any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention. The plasmids may also comprise other transcription-regulating elements such as, for example, stabilizing sequences of the intron type. In several embodiments, the plasmids may include the first intron of CMV-IE (WO 89/01036), the intron II of the rabbit beta-globin gene (van Ooyen et al.), the signal sequence of the protein encoded by the tissue plasminogen activator (tPA; Montgomery et al.), and/or a polyadenylation signal (polyA), in particular the polyA of the bovine growth hormone (bGH) gene (U.S. Pat. No. 5,122,458) or the polyA of the rabbit beta-globin gene or of SV40 virus.

The pharmaceutically acceptable vehicles or diluents or excipients or adjuvants of use are conventional. *Remington's Pharmaceutical Sciences*, by E. W. Martin, Mack Publishing Co., Easton, Pa., 15th Edition (1975), describes compositions and formulations suitable for pharmaceutical delivery of the polypeptides, plasmids, viral vectors herein disclosed. In general, the nature of the vehicle or excipient will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, freeze-dried pastille, powder, pill, tablet, or capsule forms), conventional non-toxic solid vehicles or diluents or excipients or adjuvants can include, for example, pharmaceutical grades of mannitol, lactose, starch, or magnesium stearate. In addition to biologically neutral vehicles or diluents or excipients or adjuvants, immunogenic compositions to be administered can contain minor amounts of non-toxic auxiliary substances, such as wetting or emulsifying agents, preservatives, and pH buffering agents and the like, for example sodium acetate or sorbitan monolaurate.

The compositions or vaccines according to the instant invention may include recombinant vectors encoding any polypeptide or antigen according to the present invention as described above.

Multiple insertions may be done in the same vector using different insertion sites or using the same insertion site. When the same insertion site is used, each polynucleotide insert, which may be any polynucleotide of the present invention aforementioned, may be inserted under the control of the same and/or different promoters. The insertion can be done tail-to-tail, head-to-head, tail-to-head, or head-to-tail. IRES elements (Internal Ribosome Entry Site, see EP 0803573) can also be used to separate and to express multiple inserts operably linked to the same and/or different promoters.

More generally, the present invention encompasses in vivo expression vectors including any plasmid (EP-A2-1001025; Chaudhuri P.) containing and expressing in vivo in a host the polynucleotide or gene of EHV-1 polypeptide, variant or fragment as described above and elements necessary for its in vivo expression.

In a specific, non-limiting example, the pVR1020 or pVR1012 plasmid (VICAL Inc.; Luke C. et al.; Hartikka J. et al.), pVR2001-TOPA (or pVR2001-TOPO) (Oliveira F. et al.) or pAB110 (U.S. Pat. No. 6,852,705) can be utilized as a vector for the insertion of a polynucleotide sequence. The pVR1020 plasmid is derived from pVR1012 and contains the human tPA signal sequence. The pVR1020 is a plasmid backbone available from Vical, Inc., (San Diego, Calif.) which has been previously used, see, e.g., U.S. Pat. Nos. 6,451,769 and 7,078,507. As described in Oliveira et al., plasmid pVR2001-TOPO (or pVR2001-TOPA) is pVR1020 modified by the addition of topoisomerases flanking the cloning site and containing coding for and expressing a signal secretory peptide, for example, tissue plasminogen activator signal peptide (tPA), that increases the likelihood of producing a secreted protein (Oliveira F. et al.).

Each plasmid may comprise or contain or consist essentially of, the polynucleotide according to the present invention, operably linked to a promoter or under the control of a promoter or dependent upon a promoter, wherein the promoter may be advantageously adjacent to the polynucleotide for which expression is desired. In general, it is advantageous to employ a strong promoter that is functional in eukaryotic cells. One example of a useful promoter may be the immediate early cytomegalovirus promoter (CMV-IE) of human or murine origin, or it may optionally have another origin such as from rat or guinea pig. The CMV-IE promoter may comprise the actual promoter part, which may or may not be associated with the enhancer part. Reference can be made to EP 260 148, EP 323 597, U.S. Pat. Nos. 5,168,062, 5,385,839, and 4,968,615, as well as to WO 87/03905. The CMV-IE promoter may advantageously be a human CMV-IE (Boshart M. et al.) or murine CMV-IE. In more general terms, the promoter may have either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as the desmin promoter (Kwissa M. et al.), or the actin promoter (Miyazaki J. et al.). Functional sub fragments of these promoters, i.e., portions of these promoters that maintain adequate promoter activity, are included within the present invention, e.g. truncated CMV-IE promoters according to WO 98/00166 or U.S. Pat. No. 6,156,567 and may be used in the practice of the invention. A promoter useful in the practice of the invention consequently may include derivatives and/or sub fragments of a full-length promoter that maintain adequate promoter activity and hence function as a promoter, and which may advantageously have promoter activity that is substantially similar to that of the actual or full-length promoter from which the derivative or sub fragment is derived, e.g., akin to the activity of the truncated CMV-IE promoters of U.S. Pat. No. 6,156,567 in comparison to the activity of full-length CMV-IE promoters. Thus, a CMV-IE promoter in the practice of the invention may comprise or consist essentially of or consist of the promoter portion of the full-length promoter and/or the enhancer portion of the full-length promoter, as well as derivatives and/or sub fragments thereof.

Advantageously, the plasmids comprise or consist essentially of other expression control elements. It is especially advantageous to incorporate stabilizing sequence(s), e.g., intron sequence(s), for example, the first intron of the hCMV-IE (WO 89/01036), the intron II of the rabbit β-globin gene (van Ooyen et al.). As to the polyadenylation signal (polyA) for the plasmids and viral vectors other than poxviruses, use can be made of the poly(A) signal of the bovine growth hormone (bGH) gene (see U.S. Pat. No. 5,122,458), or the poly(A) signal of the rabbit β-globin gene or the poly(A) signal of the SV40 virus.

More generally, the present invention encompasses in vivo expression vectors including any recombinant viral vector containing a polynucleotide or gene encoding one or more EHV-1 polypeptide, variants or fragments as described above, including any elements necessary for its in vivo expression.

The recombinant viral vector may be a Herpesvirus, such as an equine Herpesvirus-1 (EHV-1) as described above. The EHV-1 vector may be derived from the RacH strain, the RacL strain, the Ab4 strain, the V592 strain, the Kentucky D strain (TACC No. VR-700), the 438/77 strain (ATCC No. VR-2229), the AB69 strain (ATCC No. VR-2581), the EHV-1 NY03 strain, or a combination of EHV-1 RacH or RacL strains. In one embodiment the polynucleotide to be expressed is inserted under the control of a promoter functional in eukaryotic cells, advantageously a CMV-IE promoter (murine or human). A poly(A) sequence and terminator sequence can be inserted downstream the polynucleotide to be expressed, e.g. bovine growth hormone or a rabbit β-globin gene polyadenylation signal.

In one embodiment, the viral vector could be Newcastle Disease Virus (US2012/052089). In another embodiment, the vial vector could be selected from, for example, the poxviruses, especially avipox viruses, such as fowlpox viruses or canarypox viruses. In one embodiment, the fowlpox virus is a TROVAC (see WO 96/40241). In another embodiment, the canarypox vector is an ALVAC. The use of these recombinant viral vectors and the insertion of polynucleotides or genes of interest are fully described in U.S. Pat. No. 5,174,993; U.S. Pat. No. 5,505,941 and U.S. Pat. No. 5,766,599 for fowlpox, and in U.S. Pat. No. 5,756,103 for canarypox. More than one insertion site inside the viral genome could be used for the insertion of multiple genes of interest.

For recombinant vectors based on a poxvirus vector, a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel; Sutter et al.; available as ATCC VR-1508; or NYVAC, see U.S. Pat. No. 5,494,807, and U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO 96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807) can be used. Attenuated canarypox viruses are described in U.S. Pat. No. 5,756,103 (ALVAC) and WO 01/05934. Reference is also made to U.S. Pat. No. 5,766,599 which pertains to the attenuated fowlpox strain TROVAC. Reference is made to the canarypox available from the ATCC under access number VR-111. Numerous fowlpox virus vaccination strains are also available, e.g. the DIFTOSEC CT strain marketed by MERIAL and the NOBILIS VARIOLE vaccine marketed by INTERVET. For information on the method used to generate recombinants thereof and how to administer recombinants thereof, the skilled artisan can refer documents cited herein and to WO 90/12882, e.g., as to vaccinia virus, mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and 5,766,599 inter alia; as to canarypox, mention is made of U.S. Pat. No. 5,756,103 inter alia. When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI). In the case of canarypox, advantageously the insertion site or sites are ORF(s) C3, C5 and/or C6. In the case of fowlpox, advantageously the insertion site or sites are ORFs F7 and/or F8. The insertion site or sites for MVA virus are advantageously as in various publications, including Carroll M. W. et al.; Stittelaar K. J. et al.; Sutter G. et al.; and, in this regard it is also noted that the complete MVA genome is described in Antoine G., Virology, which enables the skilled artisan to use other insertion sites or other promoters. Advantageously, the polynucleotide to be expressed is inserted under the control of a specific poxvirus promoter, e.g., the vaccinia promoter 7.5 kDa (Cochran et al.), the vaccinia promoter I3L (Riviere et al.), the vaccinia promoter HA (Shida), the cowpox promoter ATI (Funahashi et al.), the vaccinia promoter H6 (Taylor J. et al.; Guo P. et al. J.; Perkus M. et al.).

Any of the polynucleotides disclosed here may be expressed in vitro by DNA transfer or expression vectors into a suitable host cell. The host cell may be prokaryotic or eukaryotic. The term "host cell" also includes any progeny of the subject host cell. Methods of stable transfer, meaning that the foreign polynucleotide is continuously maintained in the host cell, are known in the art. Host cells may include bacteria (for example, *Escherichia coli*), yeast, insect cells, and vertebrate cells. Methods of expressing DNA sequences in eukaryotic cells are well known in the art. As a method for in vitro expression, recombinant Baculovirus vectors (for example, Autographa California Nuclear Polyhedrosis Virus (AcNPV)) may be used with the nucleic acids disclosed herein. For example, polyhedrin promoters may be utilized with insect cells (for example, *Spodoptera frugiperda* cells, like Sf9 cells available at the ATCC under the Accession number CRL 1711, or Sf21 cells) (see for example, Smith et al.; Pennock et al.; Vialard et al.; Verne A.; O'Reilly et al.; Kidd I. M. & Emery V. C.; EP 0370573; EP 0265785; U.S. Pat. No. 4,745,051). For expression, the BaculoGold Starter Package (Cat #21001K) from Pharmingen (Becton Dickinson) may be used. As a method for in vitro expression, recombinant *E. coli* may be used with a vector. For example, when cloning in bacterial systems, inducible promoters such as arabinose promoter, pL of bacteriophage lambda, plac, ptrp, ptac (ptrp-lac hybrid promoter), and the like may be used. Transformation of a host cell with recombinant DNA may be carried out by conventional techniques are well known to those skilled in the art. Where the host is prokaryotic, such as *E. coli*, competent cells which are capable of DNA uptake can be prepared from cells harvested after exponential growth phase and subsequently treated by the CaCl2 method using procedures well known in the art. Alternatively, MgCl2 or RbCl can be used. Transformation can also be performed by electroporation. When the host is a eukaryote, such methods of transduction of DNA as calcium phosphate coprecipitates, conventional mechanical procedures such as microinjection, electroporation, insertion of a plasmid encased in liposomes, or virus vectors may be used. Eukaryotic cells may also be cotransformed with *L. longipalpis* polynucleotide sequences, and a second foreign DNA molecule encoding a selectable phenotype, such as the herpes simplex thymidine kinase gene. Another method is to use a eukaryotic viral vector (see above), such as a herpes virus or adenovirus (for example, canine adenovirus 2), to transiently transduce eukaryotic cells and express the protein (Gluzman E A). In addition, a transfection agent can be utilized, such as dioleoyl-phosphatidyl-ethanolamme (DOPE).

Isolation and purification of recombinantly expressed polypeptide may be carried out by conventional means including preparative chromatography (for example, size exclusion, ion exchange, affinity), selective precipitation and ultra-filtration. Examples of state of the art techniques that can be used, but not limited to, may be found in "Protein Purification Applications", Second Edition, edited by Simon Roe and available at Oxford University Press. Such a recombinantly expressed polypeptide is part of the present disclosure. The methods for production of any polypeptide according to the present invention as described above are also encompassed, in particular the use of a recombinant expression vector comprising a polynucleotide according to the disclosure and of a host cell.

The vaccines containing recombinant viral vectors according to the invention may be freeze-dried, advantageously with a stabilizer. Freeze-drying can be done according to well-known standard freeze-drying procedures. The pharmaceutically or veterinary acceptable stabilizers may be carbohydrates (e.g. sorbitol, mannitol, lactose, sucrose, glucose, dextran, trehalose), sodium glutamate (Tsvetkov T et al.; Israeli E et al.), proteins such as peptone, albumin, lactalbumin or casein, protein containing agents such as skimmed milk (Mills C K et al.; Wolff E et al.), and buffers (e.g. phosphate buffer, alkaline metal phosphate buffer). An adjuvant may be used to make soluble the freeze-dried preparations.

Any vaccine composition according to the invention can also advantageously contain one or more adjuvant.

The plasmid-based vaccines may be formulated with cationic lipids, advantageously with DMRIE (N-(2-hydroxyéthyl)-N,N-diméthyl-2,3-bis(tetradécyloxy)-1-propanammonium; WO96/34109), and advantageously in association with a neutral lipid, for example DOPE (dioleoyl-phosphatidyl-ethanolamine; Behr J. P.), in order to form DMRIE-DOPE. In one embodiment, the mixture is made extemporaneously, and before its administration it is advantageous to wait about 10 min to about 60 min, for example, about 30 min, for the appropriate mixture. When DOPE is used, the molar ratio of DMRIE/DOPE can be from 95/5 to 5/95 and is advantageously 1/1. The weight ratio plasmid/DMRIE or DMRIE-DOPE adjuvant is, for example, from 50/1 to 1/10, from 10/1 to 1/5 or from 1/1 to 1/2.

Optionally a cytokine may be added to the composition, especially GM-CSF or cytokines inducing Th1 (e.g. IL12). These cytokines can be added to the composition as a plasmid encoding the cytokine protein. In one embodiment, the cytokines are from canine origin, e.g. canine GM-CSF which gene sequence has been deposited at the GenBank database (accession number S49738). This sequence can be used to create said plasmid in a manner similar to what was made in WO 00/77210.

The recombinant viral vector-based vaccine may be combined with fMLP (N-formyl-methionyl-leucyl-phenylalanine; U.S. Pat. No. 6,017,537) and/or Carbomer adjuvant (Phameuropa Vol. 8, No. 2, June 1996). Persons skilled in the art can also refer to U.S. Pat. No. 2,909,462, which describes such acrylic polymers cross-linked with a polyhydroxylated compound having at least 3 hydroxyl groups, advantageously not more than 8, the hydrogen atoms of at least three hydroxyls being replaced by unsaturated aliphatic radicals having at least 2 carbon atoms. For example, the radicals are those containing from 2 to 4 carbon atoms, e.g. vinyls, allyls and other ethylenically unsaturated groups. The unsaturated radicals may themselves contain other substituents, such as methyl. The products sold under the name CARBOPOL® (BF Goodrich, Ohio, USA) are appropriate. The products are cross-linked with an allyl sucrose or with allyl pentaerythritol. Among them, there may be advantageously mentioned CARBOPOL® 974P, 934P and 971P.

Among the copolymers of maleic anhydride and alkenyl derivative, the copolymers

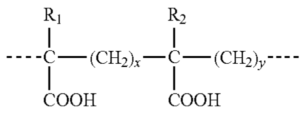

EMA® (Monsanto) which are copolymers of maleic anhydride and ethylene, linear or cross-linked, for example cross-linked with divinyl ether, are advantageous. Reference may be made to J. Fields et al.

The polymers of acrylic or methacrylic acid and the copolymers EMA® are formed, for example, of basic units of the following formula in which:

$R_1$ and $R_2$, which are identical or different, represent H or $CH_3$ x=0 or 1, preferably x=1 y=1 or 2, with x+y=2

For the copolymers EMA®, x=0 and y=2. For the carbomers, x=y=1.

The dissolution of these polymers in water leads to an acid solution, which is neutralized, advantageously to physiological pH, in order to provide the adjuvant solution into which the vaccine itself is incorporated. The carboxyl groups of the polymer are then partly in $COO^-$ form.

In one embodiment, a solution of adjuvant, especially of carbomer (*Pharmeuropa*, vol. 8, No. 2, June 1996), is prepared in distilled water, advantageously in the presence of sodium chloride, the solution obtained being at an acidic pH. This stock solution is diluted by adding it to the desired quantity (for obtaining the desired final concentration), or a substantial part thereof, of water charged with NaCl, advantageously physiological saline (NaCl 9 g/l) all at once in several portions with concomitant or subsequent neutralization (pH 7.3 to 7.4), advantageously with NaOH. This solution at physiological pH is used for mixing with the vaccine, which may be especially stored in freeze-dried, liquid or frozen form.

The polymer concentration in the final vaccine composition can be from 0.01% to 2% w/v, from 0.06 to 1% w/v, or from 0.1 to 0.6% w/v.

The subunit vaccine may be combined with adjuvants, like oil-in-water, water-in-oil-in-water emulsions based on mineral oil and/or vegetable oil and non ionic surfactants such as block copolymers, TWEEN®, SPAN®. Such emulsions are notably those described in page 147 of "Vaccine Design—The Subunit and Adjuvant Approach", Pharmaceutical Biotechnology, 1995, or TS emulsions, notably the TS6 emulsion, and LF emulsions, notably LF2 emulsion (for both TS and LF emulsions, see WO 04/024027). Other suitable adjuvants are for example vitamin E, saponins, and CARBOPOL® (Noveon; see WO 99/51269; WO 99/44633), aluminium hydroxide or aluminium phosphate ("Vaccine Design, The subunit and adjuvant approach", Pharmaceutical Biotechnology, vol. 6, 1995), biological adjuvants (i.e. C4b, notably murine C4b (Ogata R T et al.) or equine C4b, GM-CSF, notably equine GM-CSF (U.S. Pat. No. 6,645,740)), toxins (i.e. cholera toxins CTA or CTB, *Escherichia coli* heat-labile toxins LTA or LTB (Olsen C W et al.; Fingerut E et al.; Zurbriggen R et al. Peppoloni S et al.), and CpG (i.e. CpG #2395 (see Jurk M et al.), CpG #2142 (see SEQ. ID. NO: 890 in EP 1,221,955).

The composition or vaccine may also be associated with at least one EHV-1 antigen, for example inactivated EHV-1. In a particular embodiment, the EHV-1 strain may be the RacH strain, the RacL strain, the Ab4 strain, the V592 strain, the Kentucky D strain (TACC No. VR-700), the 438/77 strain (ATCC No. VR-2229), the AB69 strain (ATCC No. VR-2581), EHV-1 NY03, or a combination of EHV-1 RacH or RacL strains. These strains of EHV-1 may be inactivated by chemical or physical methods. The chemical methods are notably BPL, formaldehyde. The physical methods may notably be sonication. The inactivated EHV-1 vaccine may be combined with adjuvants, like those described previously for subunit vaccines.

Another aspect of the present invention relates to methods of vaccinating a host against EHV-1 using the vaccines or compositions disclosed herein.

The host may be any animals. In one embodiment, the host is an equine.

The routes of administration may be, for example, intramuscular (IM) or intradermal (ID) or transdermal (TD) or subcutaneous (SC). The means of administration may be, for example, a syringe with a needle, or needle free apparatus, or a syringe with a needle coupled to electrotransfer (ET) treatment, or needle free apparatus coupled to ET treatment.

For plasmid-based vaccines, advantageous routes of administration may be ID or IM. This administration may be through use of a syringe with a needle or with a needle free apparatus like Dermojet or Biojector (Bioject, Oregon, USA) or Vetjet™ (Merial) or Vitajet™ (Bioject Inc.), see US 2006/0034867. The dosage may be from 50 μg to 500 μg per plasmid. When DMRIE-DOPE is added, 100 μg per plasmid may be utilized. When GM-CSF or other cytokines are used, the plasmid encoding this protein may be present at a dosage of from about 200 μg to about 500 μg and may be 200 μg. The volume of doses can be between 0.01 ml and 0.5 ml, for example, 0.25 ml. Administration may be provided with multiple points of injection.

Alternatively, plasmid-based vaccines may be administered via the IM route coupled to electrotransfer (ET) treatment. The ET treatment may be performed using an apparatus for electrotransfer and the specifications of the manufacturer (i.e. Sphergen G250 generator (Sphergen SARL, Evry Genopole, France); MedPulser® DNA electroporation system (Innovio Biomedical Corporation, San Diego, Calif., USA)).

For recombinant viral vector-based vaccines, the routes of administration may advantageously be SC, IM, TD, or ID. This administration may be made by a syringe with a needle or with a needle free apparatus like Dermojet or Biojector (Bioject, Oregon, USA) or Vetjet™ (Merial) or Vitajet™ (Bioject Inc.). The dosage may be from about $10^4$ pfu to about $10^9$ pfu per recombinant EHV vector. The volume of doses may be from about 0.01 ml to 0.2 ml, and is advantageously 0.1 ml. Administration may comprise multiple points of injection.

For the IM route the volume of the vaccine provided may be from 0.2 to 2 ml, in particular from about 0.5 to 1 ml. The same dosages are utilized for any of the vectors of the present invention.

For subunit vaccines, the route of administration may advantageously be via SC or IM or TD or ID. This administration may be made by a syringe with a needle or with a needle free apparatus like Dermojet or Biojector (Bioject, Oregon, USA) or Vetjet™ (Merial) or Vitajet™ (Bioject Inc.). The dosage may be from about 50 to about 500 μg, in particular from about 50 to about 150 μg, and more particularly from about 50 to about 100 μg. The volume of the sub-unit vaccine provided is from 0.2 to 2 ml, in particular from about 0.5 to 1 ml.

In one aspect, the present invention relates to a vaccine strategy, which is based on a prime-boost administration regimen, where the prime-administration and the boost-administration utilize a composition comprising a pharmaceutically or veterinary acceptable excipient, diluent, adjuvant, or vehicle and the recombinant EHV-1 of the present invention. In another aspect, the present invention relates to a method of vaccinating a subject or host susceptible to EHV-1 comprising a prime-boost administration regime.

A prime-boost regimen comprises at least one prime-administration and at least one boost administration using at least one common antigen and/or variants or fragments thereof. The vaccine used in prime-administration may be different in nature from those used as a later booster vaccine. It is further noted that both the prime-administration and the boost-administration may comprise the recombinant EHV-1 of the present invention. The prime-administration may comprise one or more administrations. Similarly, the boost-administration may comprise one or more administrations.

The routes of administration, doses and volumes are as previously disclosed herein.

The prime-boost administrations may be carried out 2 to 6 weeks apart, for example, about 4 weeks apart. According to one embodiment, a semi-annual booster or an annual booster is also envisaged.

In one embodiment, the prime-boost administration regimen comprises at least one prime-administration of a recombinant EHV-1 vaccine or composition of the present invention and at least one boost-administration of an inactivated viral vaccine comprising the EHV-1 antigen, or a plasmid-based vaccine expressing the EHV-1 antigen, or a subunit vaccine comprising the EHV-1 antigen, or a combination thereof.

In another embodiment, the prime-boost administration regimen comprises at least one prime-administration of an inactivated viral vaccine comprising the EHV-1 antigen, or a plasmid-based vaccine expressing the EHV-1 antigen, or a subunit vaccine comprising the EHV-1 antigen, or a combination thereof and at least one boost-administration of a recombinant EHV-1 vaccine or composition of the present invention.

Another aspect of the present invention relates to a kit for prime-boost vaccination according to the present invention. The kit may comprise at least two vials: a first vial containing a vaccine for the prime-vaccination according to the present invention, and a second vial containing a vaccine for the boost-vaccination according to the present invention. The kit may advantageously contain additional first or second vials for additional prime-vaccinations or additional boost-vaccinations.

In one embodiment, the kit may comprise two vials, one containing a plasmid-based vaccine for the prime-vaccination according to the present invention, the other vial containing a recombinant viral vector-based vaccine for the boost-vaccination according to the present invention.

The invention will now be further described by way of the following non-limiting examples.

EXAMPLES

Without further elaboration, it is believed that one skilled in the art can, using the preceding descriptions, practice the present invention to its fullest extent. The following detailed examples are to be construed as merely illustrative, and not limitations of the preceding disclosure in any way whatsoever. Those skilled in the art will promptly recognize appropriate variations from the procedures both as to reactants and as to reaction conditions and techniques.

Construction of DNA inserts, plasmids and recombinant viral vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989). All the restriction fragments used for the present invention were isolated using the "Geneclean" kit (BIO 101 Inc., La Jolla, Calif.).

Example 1

Construction of Cell Line RK13_Pol

Cells and Viruses

Rabbit kidney (RK13) cell was maintained in Earle's minimum essential medium (EMEM) supplemented with 10% heat-inactivated fetal bovine serum (FBS), 100 U/ml penicillin and 0.1 mg/ml streptomycin (1% Pen/Strep). Equine skin fibroblast cell line (NBL6) was maintained in EMEM supplemented with 10% FBS, 29 mg/ml L-glutamate, 1% Pen/Strep and 1% nonessential amino acids (Gibco BRL). EHV-1 strains RacL11 and NY03 were grown on fresh RK13 cells. NY03, harboring a non-neurological form of DNA polymerase (N752 Pol), was isolated from an aborted foal from a farm in New York in 2003.

Construction of Cell Line RK13 Pol

To support the growth of Pol-negative RacL11 mutant, a rabbit kidney cell line designated RK13_Pol expressing the non-neurological form of the polymerase (N752) was first generated. The whole polymerase open reading frame of NY03 was amplified from viral genomic DNA, which was extracted from virus infected RK13 cells. The polymerase chain reaction (PCR) was performed using Accuprime DNA polymerase (Invitrogen, Carlsbad, Calif., USA) and primer pair PN1/PN2 (Table 1). The amplicon, flanked with a HindIII restriction site at 5'end and a BamHI site as well as a HA Tag at 3'end, was cloned into plasmid pCDNA3 to generate pCDNA3-Pol. After digestion with PvuI, 4 µg of recombinant plasmid pCDNA3-Pol was linearized and transfected into RK13 cells grown in six-well plates using Lipofectamine 2000 (Invitrogen). Transfected cells were propagated in EMEM containing 10% FBS and 1.2 mg/ml G418 (Merck). A single cell clone in which every cell was shown to express DNA polymerase by indirect immunofluorescence assay (IFA) was selected and termed RK13_Pol. By IFA using anti-HA MAb, the expression of polymerase in RK13_Pol could be demonstrated (FIG. 3) and shown to be stable in ten times of passages.

TABLE 1

Primer Sequences

| Primer Name | SEQ ID NO: | Sequence |
|---|---|---|
| PN1 | 16 | 5'-CCCAAGCTTgagATGGCGGCGCGCGAACAGGCCA-3' |
| PN2 | 17 | 5'-CGCGGATCCTTAAGCGTAGTCTGGGACGTCGTATGGGTAGCTTTGATGGGGAGCTGCTTCT-3' |
| P1 | 18 | 5'-GCCTGCGTGGAGGAGTATTGGG-3' |
| P2 | 19 | 5'-TAATTGATTACT**ATTAAT**AACTATTACACCGGAGGAAGAAAGTCG-3' |
| P3 | 20 | 5'-CAAACTCATCAATGTAT**C**TTAAGGTCTGTGTAAATTTAAAGTGCGA-3' |
| P4 | 21 | 5'-CAAAGGTGCCAGCGTCACATCG-3' |
| P5 | 22 | 5'-ACGACTTTCTTCCTCCGGTGTAATAGTT**ATTAAT**AGTAATCAATT-3' |
| P6 | 23 | 5'-CCCTTGCTCACCATGGTGGCGGATCTGACGGTTCACTAAACC-3' |
| P7 | 24 | 5'-GGTTTAGTGAACCGTCAGATCCGCCACCATGGTGAGCAAGGG-3' |
| P8 | 25 | 5'-CGCACTTTAAATTTACACAGAC**CTTAAG**ATACATTGATGAGTTTG-3' |
| P9 | 26 | 5'-TCC**CCGCGG**ATAACTTCGTATAGCATACATTATACGAAGTTATTAGTTATTAATAGTAATCAAT-3' |
| P10 | 27 | 5'-CTA**GCTAGC**ATAACTTCGTATAATGTATGCTATACGAAGTTAT**CTTAAG**ATACATTGATGAGTT-3' |
| gC-1 | 28 | 5'-GACTCTGTCGACGGCCACCGCCGAC-3' |
| gC-2 | 29 | 5'-CCTGGATCCAGACTCTATTCCCATG-3' |
| ΔgC-1 | 30 | 5'-TTGGCCTATGCGGACGACTT-3' |
| ΔgC-2 | 31 | 5'-CCCTTTGGTGCATGGTATGT-3' |

TABLE 1 -continued

Primer Sequences

| Primer Name | SEQ ID NO: | Sequence |
|---|---|---|
| Poly1 | 32 | 5'-TCTGG AACTA TCGGC GGTGG C-3' |
| Poly2 | 33 | 5'-CGGGT CTTGA GGAGC ATGTC G-3' |

Example 2

Plasmids and Viral Mutagenesis

Generation of Virus Mutants

Conventional homologous recombination strategy was employed for all genetic manipulations. Two 1.7 kbp flanking fragments on either side of DNA polymerase were amplified using thermostable Pfu polymerase (Promega) and primer pairs P1/P2 and P3/P4 from RacL11 genome. Another two primer pairs P5/P6 and P7/P8 were used to amplify the HCMV (human cytomegalovirus) promoter and EYFP (enhanced yellow fluorescent protein) gene from plasmid pEYFP-N1, separately. The 5'ends of primers P2 and P5, P3 and P8 as well as P6 and P7 carry homologous sequences of 21-23 bp. With an overlapping PCR using P5 and P8, HCMV promoter and EYFP gene were fused and cloned into plasmid pCR2.1-Topo (Invitrogen) resulting in pCES1. For the construction of shuttle plasmid pCR-Topo-P1P4, the above two homolog arms and EYFP expressing cassette in pCES1 were combined by overlapping PCR using primers P1/P4 and cloned into pCR2.1-Topo. Using pCES1 as template and primer pair P9/P10, EYFP cassette flanked with SacII and NheI restriction sites as well as LoxP sequences upstream and downstream was amplified and cloned into pCR2.1-Topo resulting in plasmid pCES2. To generate plasmid pCR-Topo-gC, a 5.87 kbp gC-containing fragment, which was amplified from RacL11 genome using primers gC-1 and gC-2, was cloned into pCR2.1-Topo. After digestion with SacII and NheI, EYFP cassette was released from pCES2 and transferred to pCR-Topo-gC to replace gC gene and the recombinant shuttle plasmid was termed Topo-ΔgC-EYFP. Plasmids pCES1, pCES2, pCR-Topo-P1P4 and Topo-ΔgC-EYFP were identified by digestion and sequencing. The cloning scheme is depicted in FIG. 2.

For the mutation of DNA polymerase, 1 µg of RacL11 viral DNA and 10 µg of plasmid pCR-Topo-P1P4 were co-transfected into RK13_Pol cells in a 6-well plate by calcium phosphate precipitation. Two days post transfection, green plaques were observed under a fluorescence microscope (Axiovert 25, Zeiss). The whole virus was harvested after 2 cycles of freeze-thaw and grown on fresh RK13_Pol cells that were overlaid with 1.5% methylcellulose in EMEM-2% FBS at 1 hour post infection. After 3 times of purification, homogenous Pol-negative RacL11 mutant, termed L11_ΔPol EYFP, was generated and identified using restriction fragment length polymorphism (RFLPs) analyses. To restore N752 Pol, a 7 kbp fragment, termed p1p4pol, was amplified from EHV-1 NY03 genome using Accuprime Tag polymerase and primers P1/P4. By co-transfection of 1 µg of L11_ΔPol EYFP viral DNA and 4 µg of p1p4pol PCR product into RK13 cells, homologous recombination was used again to introduce N752 Pol variant and RacL11 mutant L11_D752N was obtained. The D752 to N752 mutation in polymerase was confirmed (FIG. 2D) by sequencing a 780 bp Pol fragment that was amplified from L11_D752N using sequencing primers poly1 and poly2.

Next steps were to delete gC open reading frame from L11_D752N mutant. Briefly, 1 μg of L11_D752N viral DNA and 10 μg of transfer plasmid Topo-ΔgC-EYFP were co-transfected into RK13 cells. The SacII/NheI fragment (1.2 kbp in length) in gC gene was replaced with EYFP cassette leading to the generation of recombinant virus L11_D752N ΔgC EYFP. The EYFP selection marker was excised by expressing Cre recombinase upon co-transfection of L11_D752N ΔgC EYFP and plasmid pCAGGS-NLS/Cre into RK13 cells. White plaques were purified and a gC-negative, non-neurological RacL11 mutant L11_D752N ΔgC was finally engineered. By the homologous recombination between L11_D752N ΔgC EYFP viral DNA and plasmid pCR-Topo-gC, gC gene was repaired, resulting in a gC revertant L11_D752N ΔgC rev (FIG. 2). The deletion of gC gene and the absence of gC protein were confirmed by PCR identification using primer pairs gC-1/gC-2 and ΔgC-1/ΔgC-2, sequencing, as well as indirect immunofluorescence assay (IFA).

All the primers used for the construction of plasmids and sequencing were listed in Table 1.

Indirect Immunofluorescence Assay (IFA)

For the detection of DNA polymerase that was expressed in RK13_Pol cells, monoclonal antibody (MAb) directed against HA Tag (H3663, Sigma) was used. RK13_Pol cells grown in a 6-well plate were washed with phosphate-buffered saline (PBS) and fixed in 3.5% paraformaldehyde in PBS for 1 h at room temperature (RT), followed by a 5 min incubation in PBS containing 30 mM glycine and another 5 min permeation in 0.1% Triton X-100 in PBS. After washing with PBS, cells were blocked with PBS-3% bovine serum albumin (BSA) for 30 min at RT. Cells were then incubated with the primary antibody at a 1:10000 dilution in PBS-3% BSA for 1 h at RT and extensively washed with PBS. The secondary antibody (Alexa Fluor568-conjugated goat anti-mouse IgG, Invitrogen) was added with a dilution of 1:2000 in PBS-3% BSA and incubated for 1 h at RT. After thorough washing for 3 times of 10 min, fluorescence signal was inspected under the inverted fluorescence microscope (Axiovert 25, Zeiss).

To confirm the absence of gC protein, RK13 cells were seeded in a 6-well plate and infected with wild type RacL11, mutant L11_D752N ΔgC or gC revertant L11_D752N ΔgC rev at a multiplicity of infection (MOI) of 0.0001. One hour post infection, viruses were removed and infected cells were overlaid with 1.5% methylcellulose in EMEM-2% FBS. After 48 h of incubation at 37° C., cells were fixed and blocked as described above. MAb 1G4 directed against EHV-1 gC protein and B8 against EHV-1 gM protein were used as the primary antibodies with a dilution of 1:100 and 1:200, separately. After incubation with the secondary antibody (Alexa Fluor568-conjugated goat anti-mouse IgG) for 1 h, cells were washed and plaques were observed.

Characterization of Virus Mutants

Figures 5, 5C, 5D, 5E, 5F:
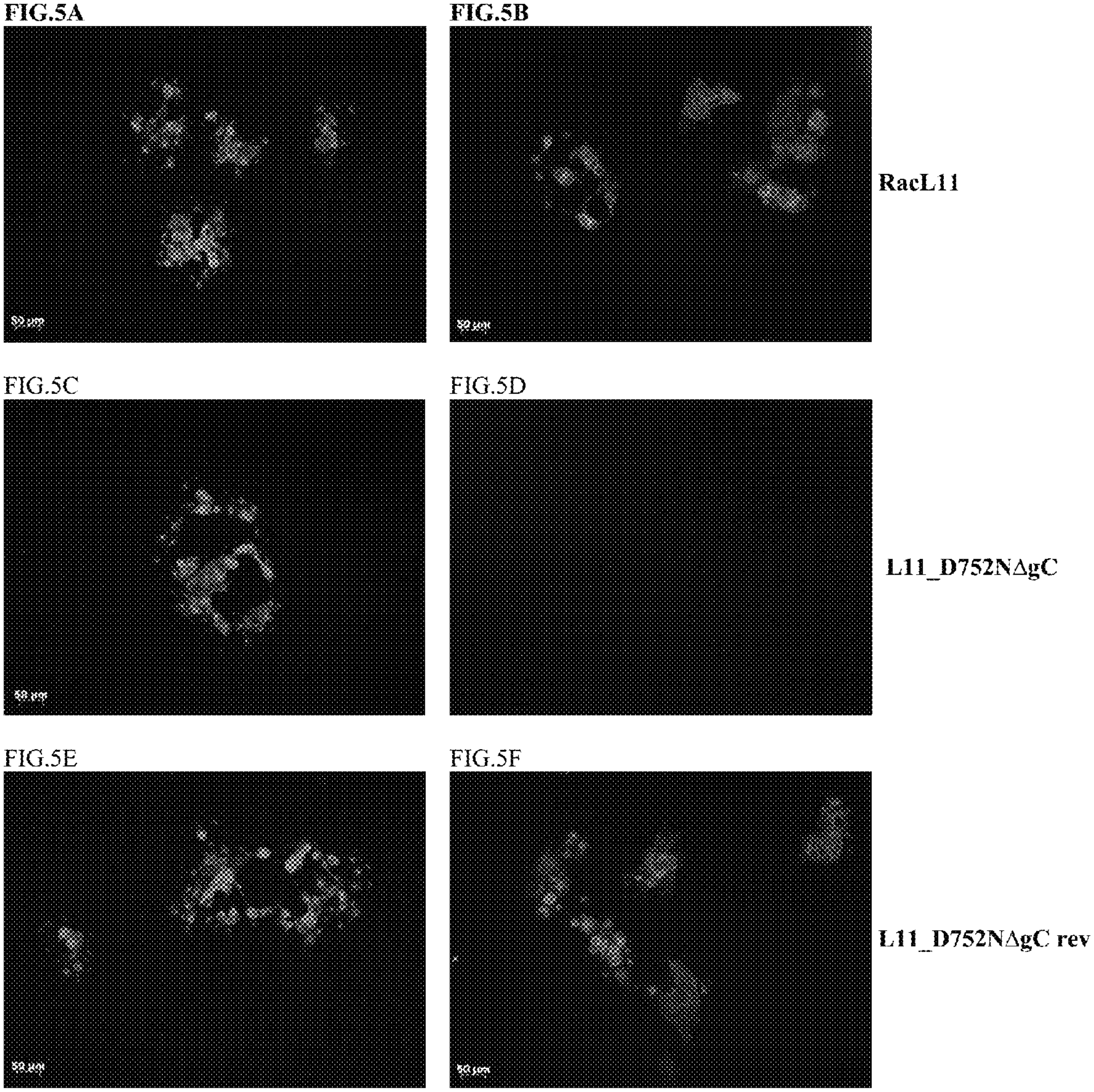

A Pol-negative virus mutant L11_ΔPol EYFP was generated by replacing the authentic polymerase gene with EYFP via co-transfection of RacL11 viral DNA and shuttle plasmid pCR-Topo-P1P4 into RK13_Pol. L11_ΔPol EYFP was found to be able to grow only in RK13_Pol but not in non-complementing RK13 cells (FIG. 4), which confirms that DNA polymerase is essential for virus growth of EHV-1 in vitro. The mutation from neurological D752 to non-neurological N752 genotype was then achieved by restoring the non-neurological polymerase gene of EHV-1 NY03 into L11_ΔPol EYFP. The single amino acid variation was confirmed by sequencing a 780 bp amplicon from the mutant L11_D752N. Based on L11_D752N, the SacII/NheI region representing a 1222 bp fragment (from nucleotide position 94 to 1315) in gC gene was replaced with EYFP, resulting in a gC-negative intermediate L11_D752N ΔgC EYFP. By the expression of Cre, EYFP cassette was finally excised, leaving one copy of LoxP sequence (34 bp) between the SacII and NheI restriction sites in the engineered mutant L11_D752N ΔgC. To confirm the deletion in gC gene, PCR was performed. While from the parental mutant L11_D752N, 5.87 kbp and 1.6 kbp fragments could be amplified using primer pair gC-1/gC-2 and ΔgC-1/ΔgC-2, from L11_D752N ΔgC, however, 4.68 kbp and 410 bp fragments were amplified (FIG. 2), suggesting that a deletion of 1.2 kbp in gC gene was present. By IFA using anti-EHV-1 gC MAb, it could be shown that gC protein was detectable in cells infected with either RacL11 or the revertant L11_D752N ΔgC rev, but in cells infected with L11_D752N ΔgC, the expression of gC protein was abolished (FIG. 5). A gC-negative and non-neurological RacL11 mutant was thus successfully generated.

Example 3

Characterization of In Vitro Virus Growth

Virus Attachment Assay

Virus attachment assay was carried out as described in Sun et al. (J Gen Virol 77, 493-500, 1996) with slight modifications. Monolayers of RK13 cells seeded in 6-well plates were cooled for 1 h at 4° C. and infected with RacL11, L11_D752N, L11_D752N ΔgC or L11_D752N ΔgC rev with an MOI of 400 plaque-forming units (PFU) per well. The viruses were left to attach for various length of time (0, 15, 30, 60, 120, 240 min) at 4° C. At various time points, infected cells were washed three times with PBS and overlaid with EMEM containing 2% FBS and 1.5% methylcellulose. After incubation for 3 days at 37° C., cells were fixed with 10% formaldehyde and stained with 0.3% crystal violet. Plaques were counted and the percentage of virus attachment at each time point was calculated, relative to time point 240 min that was set to 100% attachment.

Plaque Size and Single-Step Growth Kinetics

To compare the plaque sizes, RK13 cells grown in 6-well plates were infected with RacL11 wild type and the mutants L11_D752N, L11_D752N ΔgC or L11_D752N ΔgC rev at an MOI of 0.0001 and overlaid with 1.5% methylcellulose in EMEM containing 2% FBS at 2 hpi. Three days post-infection, plaques were visualized by IFA using anti-EHV-1 gM MAb B8. For each virus, 50 plaques were photographed and average plaque areas were measured by using ImageJ software (available on NIH's Research Services Branch website). Plaque sizes induced by RacL11 were set to 100%. Mean percentage and standard deviation were calculated from three independent experiments. For single-step growth kinetics assays, RK13 cells seeded in 24-plates were infected at an MOT of 3. The viruses were allowed to attach for 1 h at 4° C., followed by a penetration step of 1.5 h at 37° C. After washing twice with PBS, the infected cells were treated with ice-cold citrate buffered saline (CBS, pH 3.0) for 3 min to remove virus on the surface. At different time points (0, 4, 8, 12, 24, 36, 48 hpi), supernatants and cells were collected separately. Extracellular and cell-associated viral titers were determined using conventional plaque assays. Single-step growth curves were computed from three independent experiments.

In Vitro Growth Properties

Figure 6:
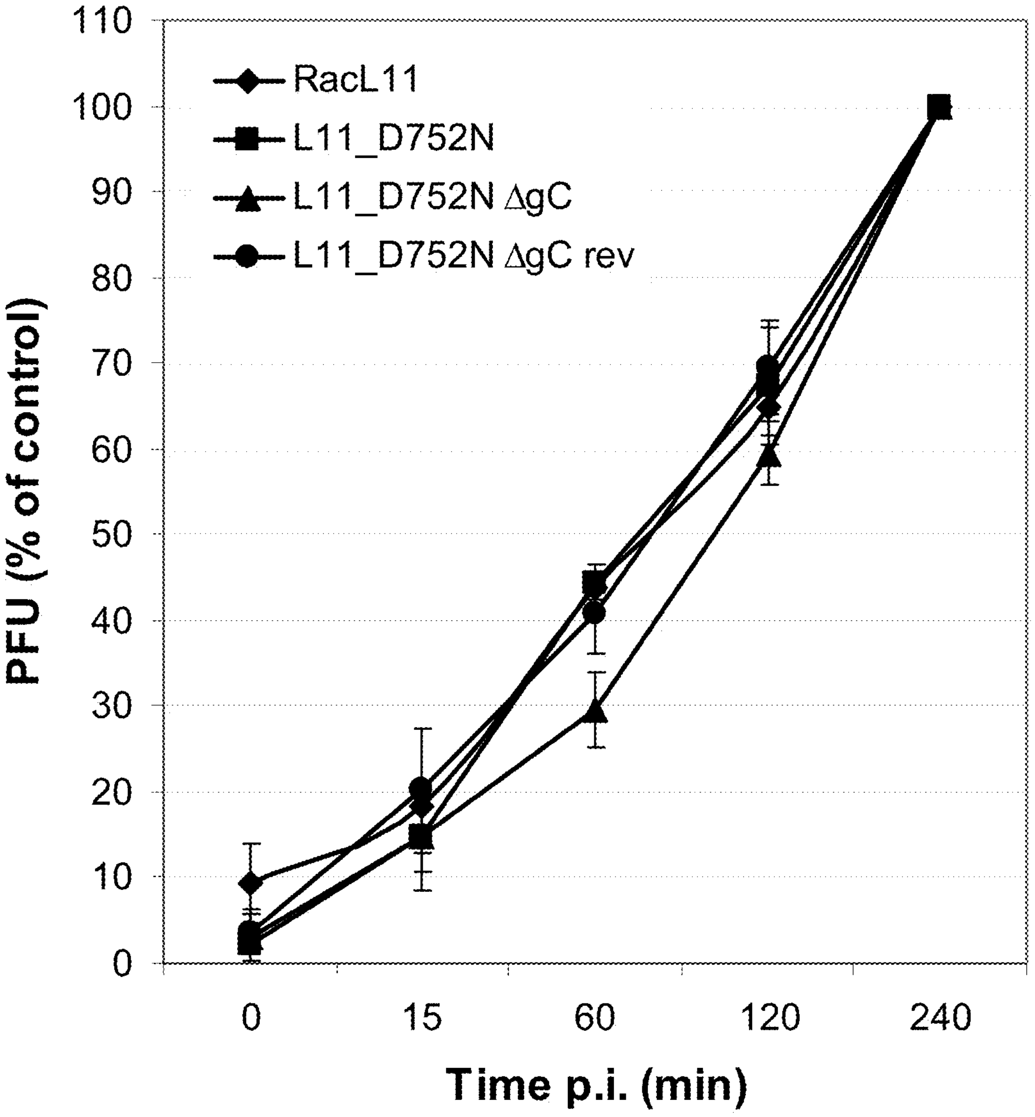
FIG. 6 depicts the in vitro growth of RacL11, L11_D752N, L11_D752NΔgC and L11_D752NΔgC rev measured by attachment assay.
Figure 7:
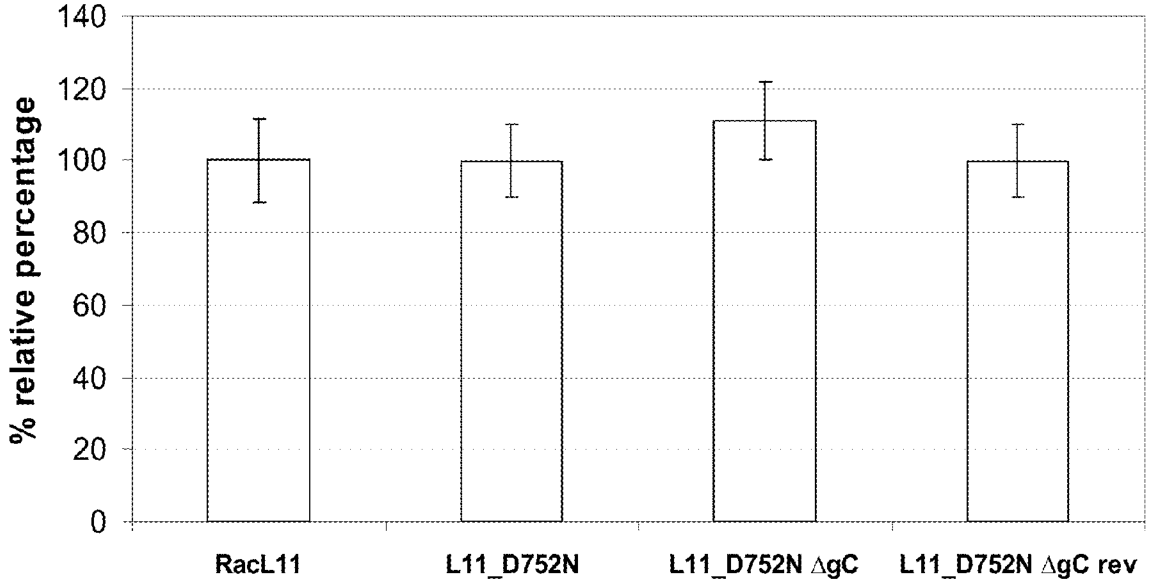
FIG. 7 depicts the in vitro growth of RacL11, L11_D752N, L11_D752NΔgC and L11_D752NΔgC rev determined by comparing plaque sizes.
Figure 8:
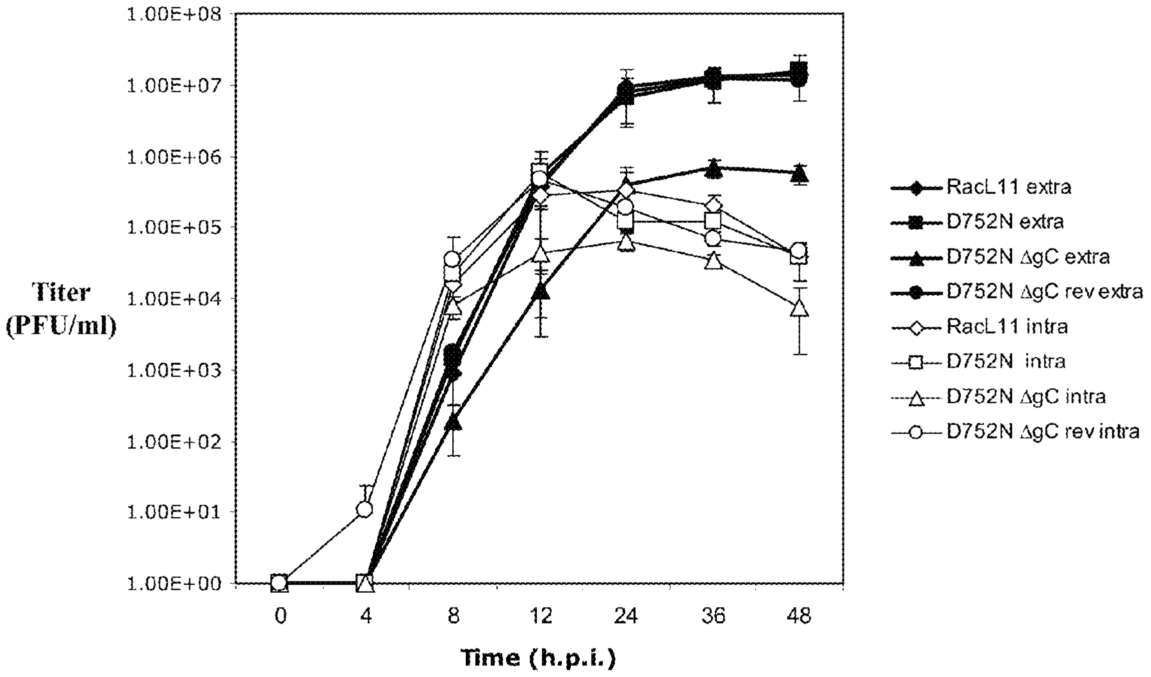
FIG. 8 depicts the growth kinetics of RacL11, L11_D752N, L11_D752NΔgC and L11_D752NΔgC rev by extracellular and intracellular titers.

The in vitro growth properties of various virus mutants in cultured cells were analyzed. To investigate the impact of gC deletion on binding ability of L11_D752N ΔgC to target cells, attachment assay was performed. As expected, L11_D752N ΔgC was shown to bind less efficiently to RK13 cells when compared with either wild type RacL11, parental virus L11_D752N or the revertant L11_D752N ΔgC rev (FIG. 6). The ability of L11_D752N ΔgC to spread from cell to cell was determined by comparing plaque sizes. Whereas no significant difference could be observed between wild type, parental virus and gC revertant, the relative plaque area formed by L11_D752N ΔgC, however, was 10% larger ($p<0.0001$) than those of others (FIG. 7), indicating that with the absence of gC, the cell-to-cell spread of EHV-1 is even more efficient. With respect to growth kinetics, the in vitro replication of L11_D752N ΔgC was less effective as demonstrated by extracellular and intracellular titers that were reduced by approximately 20-fold and 10-folds, respectively, relative to wild type, parental virus or gC revertant (FIG. 8). The virus titers in cell culture supernatants infected with wild type RacL11, parental virus L11_D752N or the repaired L11_D752N ΔgC rev reached the value of intracellular titers at approximately 12 hours post-infection. In L11_D752N ΔgC infected cells, however, a delayed release of infectious progeny was observed by that the extracellular titer crossed intracellular titer at 16-18 hours post-infection. From these results, it could be concluded that the in vitro growth of L11_D752N ΔgC was impaired in virus binding and egress though it could form slightly larger plaques.

Example 4

Vaccination of Mice

Wild type RacL11 as well as the mutants L11_D752N, L11_D752N ΔgC and L11_D752N ΔgC rev were purified by ultracentrifuge for 1 h at 27,000 rpm. The pellets were suspended in PBS, titrated on fresh RK13 cells, aliquoted and stored at −70° C. until use. Three-week-old female BALB/c mice (Harlan) were randomly allocated into five groups of 16 mice each and left to acclimate to each other for one week in the Biosafety Level-2 facility. On day 0, all mice were weighted, anesthetized with 0.1 mL/10 g Xylazine/Ketamine and four groups were inoculated intranasally (IN) with each virus at a dose of $1\times10^5$ PFU in 20 μL of PBS. The last group was used as a negative control and received 20 μL of PBS. Bodyweights of each mouse was inspected until day 14 post inoculation (p.i.). Three mice from each group were euthanized on day 2 and day 4. The lung was removed, part of which was homogenized and used for determination of virus titers by standard titration on RK13 cells, and the rest was fixed with 10% formaldehyde and processed for histopathological analysis. On day 28, mice were challenged with wild type RacL11 at a dose of $1\times10^5$ PFU by the intranasal route. Data of individual bodyweights were collected for two weeks. On day 2 and day 4 post challenge (p.c.), three mice of each group were euthanized to remove the lung. Virus titers in the lung tissues were determined on fresh RK13 cells after homogenization.

Figures 9, 9A:
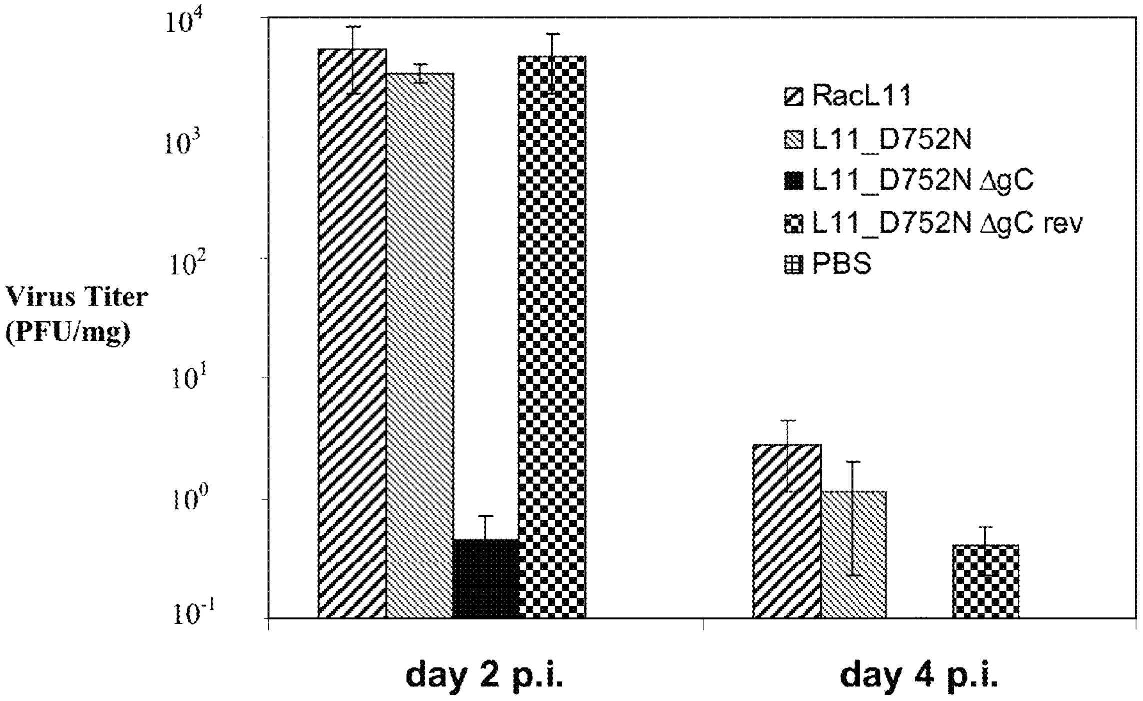
FIGS. 9A and 9B depict the mean virus titers in lungs infected with RacL11, L11_D752N, L11_D752NΔgC, L11_D752N ΔgC rev 2 and PBS (control) 2 and 4 days post infection (p.i.), 2 and 4 days post challenge (p.c.).
Figures 9, 9B:
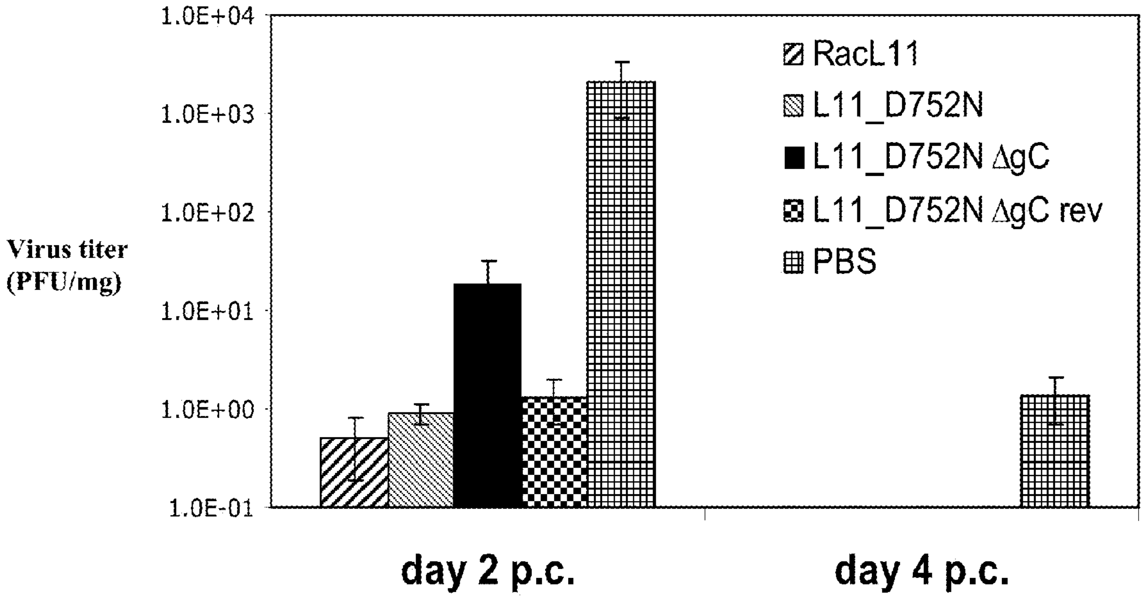
Figure 10:
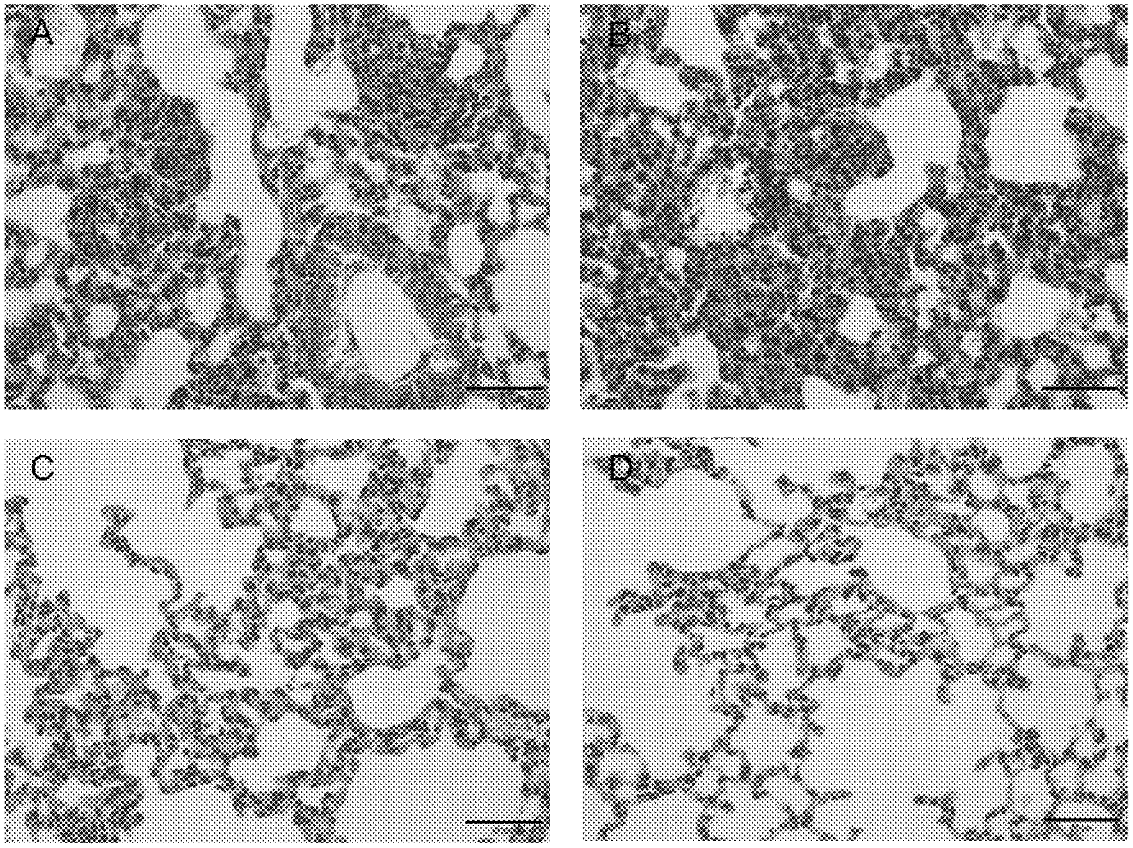
FIG. 10 depicts the histopathological changes of the lungs of mice infected with RacL11, L11_D752N, L11_D752NΔgC, L11_D752N ΔgC rev on day 2 p.i.

On day 2 p.i., mean virus titers in lungs infected with RacL11, L11_D752N or L11_D752N ΔgC rev reached 5366 PFU/mg, 3450 PFU/mg and 4800 PFU/mg, respectively (FIG. 9), between which no statistically significant difference was observed ($p\geq0.442$). This result indicated that the single amino acid variation from D752 to N752 in DNA polymerase does not impair the in vivo growth of EHV-1 in mice, which was consistent with previous findings (Goodman et al., 2007). In contrast, the in vivo replication of the gC-negative mutant L11_D752N ΔgC was significantly less effective ($p<0.001$), with a mean virus titer of only 0.45 PFU/mg in lung tissues. On day 4 p. i., no virus could be recovered from L11_D752N ΔgC infected mice. With respect to histopathological changes on day 2 p. i., the lungs of mice infected with either wild type RacL11 or the polymerase mutant L11_D752N showed mild suppurative pneumonia accompanied by neutrophilic infiltration, increased perivascular edema and increased number of inflammatory cells (predominantly lymphocytes) in lymph vessels and perivascular area, whereas no abnormality was detected in lungs infected with L11_D752N ΔgC and PBS (FIG. 10). As a result of the inflammatory response, continuous body weight loss of mice infected with RacL11, L11_D752N or the rescuant virus L11_D752N ΔgC rev was observed till day 3 p. i. The body weight of mice infected with L11_D752N ΔgC, however, did not exhibit apparent reduction. On day 28 p. i., all the mice were challenged intranasally with RacL11. Two days post challenge (p. c.), RacL11 replicated to a titer of 2100 PFU/mg in lungs of mock-inoculated mice, but only 18.8 PFU/mg in L11_D752N ΔgC group (FIG. 9). The virus titers in lungs of mice inoculated with RacL11, L11_D752N or L11_D752N ΔgC rev were even lower (0.5, 0.9 and 1.3 PFU/mg, FIG. 9) on day 2 p. c., which was, however, at the expense of high growth efficiency and pathogenicity in vivo. On day 4 p. c., resolution of virus from L11_D752N ΔgC group was not successful. On the basis of these results we concluded that the gC-negative, nonneurological mutant L11_D752N ΔgC is severely attenuated and apathogenic for mice, but can confer protective immunity.

Example 5

Vaccination of Horses

Horses (6 to 8 month old foals) were grouped into three groups A, B and C. Group A was treated with live attenuated EHV-1 virus having gC gene deleted (L11_D752N ΔgC). Group B was treated with live attenuated EHV-1 virus (RacL11). Group C was control group. Vaccination and samplings were done according to the schedule shown in Table 2.

TABLE 2

| Group | Vaccination 6.3 $\log_{10}$DICC$_{50}$ | Samples for vaccine shedding | Challenge | Post-challenge examination | Blood sampling | Nasal swabbing |
|---|---|---|---|---|---|---|
| A<br>n = 8 | Intramuscular route<br>D 0: 2.4 ml<br>D 28: 2.0 ml | D −1, D 3, D 4, D 5, D 6, D 7, D 10 and D 13. D 27, D 31, | D 42 EHV1 strain $10^{5.0}$ | Daily from D 42 to D 56 | D −1, D 7, D 13, D 27, D 41, D 43, D 44, D 45, | D −1, D 41, daily from |

TABLE 2-continued

| Group | Vaccination 6.3 $log_{10}DICC_{50}$ | Samples for vaccine shedding | Challenge | Post-challenge examination | Blood sampling | Nasal swabbing |
|---|---|---|---|---|---|---|
| B n = 8 | D 0 and D 28 Intramuscular route Dose = 1.5 ml | D 32, D 33, D 34, D 35, D 38 and D 41 | TCID50/ nostril | | D 46, D 47, D 48, D 49, D 52 and D 56 | D 43 to D 49, D 52 and D 56 |
| C n = 8 | Not vaccinated | D −1 and D 27 | | | | |

Both vaccines were well tolerated by the foals. The vaccine virus strains could not be detected in any sample by virus isolation. Control horses did not seroconvert up to the time of challenge as evidenced by the absence of SN and CF antibody titers to EHV-1. Horses from group A and B mounted a SN response to first vaccination which was boosted after second vaccination. CF antibody titers in both groups of horses remained low/undetectable after first vaccination and increased after second vaccination, but never reached high levels (FIG. 11).

Figure 12:
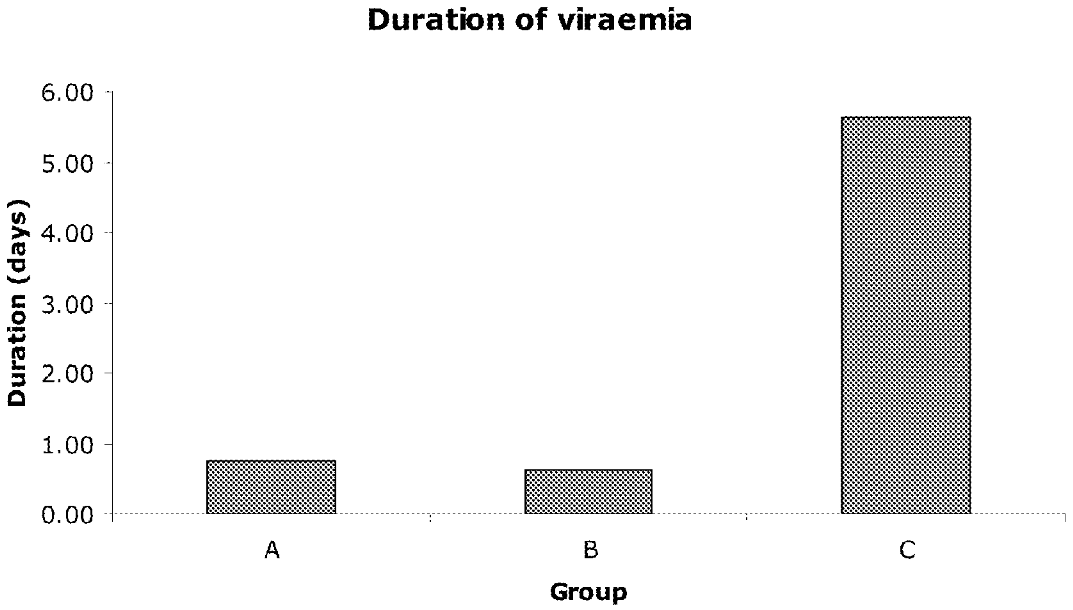
FIG. 12 depicts the duration of viraemia in vaccinated horses.
Figure 13:
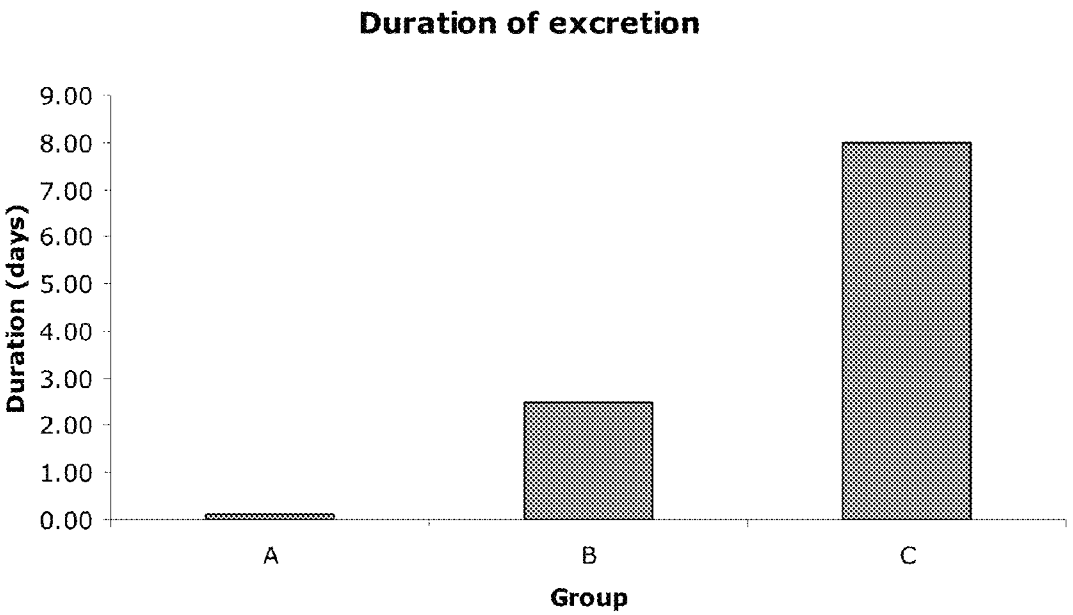
FIG. 13 depicts the virus shedding in nasal swabs from the vaccinated horses.

Clinical signs after challenge in the control horses included a tri-phasic fever response and respiratory disease characterized by moderate to severe nasal discharge. In contrast, hyperthermia was only sporadically found in both vaccinated groups of horses and nasal discharge was reduced in severity and duration. A notable effect of vaccination was the complete absence of viremia after challenge in 5/8 horses from both group 1 and 2 (FIG. 12). Also the duration of viremia was reduced in the vaccinated compared to the control horses. FIG. 13 shows that group A had significantly reduced virus shedding in the nasal swabs, whereas nasal shedding in group B horses was more variable, but reduced compared to the control horses.

Example 6

Sequencing of RacL11 gC Gene

The gC gene of RacL11 was sequence and is represented by SEQ ID NO:34 and SEQ ID NO:35 for DNA and protein sequence, respectively.

It will be apparent that the precise details of the methods described may be varied or modified without departing from the spirit of the described disclosure. We claim all such modifications and variations that fall within the scope and spirit of the claims below.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What we claim is:

1. A composition comprising a recombinant Equine Herpesvirus-1 (EHV-1), wherein the EHV-1 comprises a mutated gene which encodes a non-functional Glycoprotein C (gC) wherein the gC gene is deleted, and wherein the EHV-1 further comprises a DNA polymerase (Pol) comprising an asparagine (N) at the amino acid position 752 from the starting methionine.

2. The composition of claim 1, further comprising a pharmaceutically or veterinarily acceptable vehicle, diluent, adjuvant, or excipient.

3. A recombinant EHV-1 comprising a mutated gC gene encoding a protein wherein the gC gene is deleted, and a DNA polymerase (Pol) gene encoding a Pol comprising an asparagine (N) at the amino acid position 752 from the starting methionine.

4. A method of vaccinating an animal comprising at least one administration of the composition or recombinant EHV-1 of claim 1 or 3.

5. The method of claim 1, wherein the method comprises a prime-boost administration regime.

6. A method of eliciting a protective response in an animal against Herpesvirus comprising administering to the animal the composition or recombinant EHV-1 of claim 1 or 3 and a pharmaceutically or veterinarily acceptable carrier, adjuvant, excipient or vehicle.

7. The method of claim 4 or 6, wherein the animal is equine.

8. The composition of claim 1, wherein the EHV-1 is derived from an EHV-1 strain selected from the group consisting of the RacH strain, the RacL strain, the Ab4 strain, the V592 strain, the Kentucky D strain, the 438/77 strain, the AB69 strain, the EHV-1 NY03 strain, and a combination thereof.

9. The recombinant EHV-1 of claim 3, wherein the EHV-1 is derived from an EHV-1 strain selected from the group consisting of the RacH strain, the RacL strain, the Ab4 strain, the V592 strain, the Kentucky D strain, the 438/77 strain, the AB69 strain, the EHV-1 NY03 strain, and a combination thereof.

* * * * *

SEQUENCE LISTING

```
<160> NUMBER OF SEQ ID NOS: 37

<210> SEQ ID NO 1
<211> LENGTH: 3663
<212> TYPE: DNA
<213> ORGANISM: artificial
<220> FEATURE:
<223> OTHER INFORMATION: EHV-1 DNA polymerase (Pol) gene (AY464052) from
      EHV-1 V592 strain

<400> SEQUENCE: 1

tcagctttga tggggagctg cttctagagt acaaaaaact gtatgcagta ttcgacgact     60

ttcttcctcc ggtgtaaagg gcgtcagctt ttcaaagccg gcgcgctcaa gcagtgcctg    120

ggttttcgtg ggggtcttgt ggggggtttc cggaataaac cgctttaaaa gattttctgt    180

tgttctcaca tcatttccga atagagcctt aaaggtcacg cttatggtac ccaacaggtg    240

ggagaaatag tagtctgtgt ttagcggtac gtcattctcg gaaacatagg tcgggtcttc    300

ggcgaggtcg gaaaccagca gtttgcgttt aggttggggg cgtgcggtct tggttaccac    360

ggggttttgg gcggtaccgc gcattgagtt tactacaccc gcttcgcgtt ccgcggcctc    420

ggtctgcgca actatcacat acggaattct ctcttttacg ctgggcagtt cttcattcct    480

catggcgagc ttaaagtaga cggtgaggtg cggcaggcgc ttgttggtat acgattcggg    540

tgagcggctc agctcagcag tcataacgaa ctcgcgcacg tccaagttgg gggcagtgat    600

acggttgtac gcctctacca gcactcgccc aaacttgtca aagccgctcg gtagcgggcg    660
```

-continued

```
ccccacccat tctgcgggag gcacgtctgt cacctttgct gccgccgtgg ccacatcctc    720
gtcgtacaac aaaagatcta ccagatgtcg cgcgtacaag tttatgaaag agcagttatt    780
tttgcggacc aggtcgaccc ccttcatgag catcttcccc ccgtttatga cacctatgta    840
cttcttcttg gtgatcagca gcagtcgctg aaaggtcttc tcacactcca gtttgatggg    900
cgctctaaag aggtccgctg aaatctgacg cgacatagca tcccccagct ccgatacccc    960
ctcgtacgtc aggcccacaa acttgataaa cacggagtcg gtgtctccgt agataaccct   1020
gacggagtaa ggcttgtggt ttcggaaacc tatagcccct ggaaaattgt cctccagcag   1080
ctcgcgcgtc gcccaacgag agtgaacgta atctcgggtc ttgaggagca tgtcgcgtcc   1140
tatcgtggta acggtagccg ctatcctcag acacggcaac aggccgtttg ccaccccccgt   1200
gaatccgtaa accgagttgc atatcacctt aatcgcagac tgctgcttat ctagtaaaac   1260
tgcctcctcg gggtgctgg tggggattcg cgccctcacc gcctttcgca tggccagcca   1320
gtcgcgcagc aagatgccaa gcaggctttc gcgaatatgg gcgtggacaa aaaataactt   1380
ttggtcaccc acctcgaacg tcgagtagtt gacggatggt tgaagcccgg ccagatccac   1440
ttcatcgagc gccagggtgg tgaaacagag gttatgggcc tggataatgc ttgggtataa   1500
gctagcgaag tcaaacacaa ccacggggtc cacatgaaag ccggatacgg ggtctagaac   1560
ctttgctccc tggtagccca cggccctccc gacgccgggc ttcccgcctc cgttttcaga   1620
agtagcgcca gatcctgcgg cgtccggggt accgtccaca ccgtcgggtt cgtctgtact   1680
gtcgaaggcg tggctttggc tatccatagc caactccgaa gtctctgacg cggcgtctgc   1740
ctgactgtca aaccggcgtc tgttgtctgg caaaatgaaa tttctctcgc gggcgagttt   1800
cagcaagcac gtgtacacgc gaatttgctg accgtcaaaa attacccgcg ttagggtgat   1860
acgggcgagt ttggccaccg ccgatagttc cagatggggg aggtacttaa aaaacagctt   1920
gcccaccagc ctagagtcct ggatacaata ctctcctatt acgcccctcc ggtcaggccc   1980
tcccgcgtaa taggagggta tttctttata gggaaggtct atcttatgct cgccgaggac   2040
gtctcccacg accgcgtcga gtttgtagct gggtagcttt agcttttccg tcgccacaga   2100
atacatgtct agagatatca ggccattgat tttcaccttg ctcttcttct gaaaatggtt   2160
cgtggcgatg tcccacacct taaacagccc ccctttgttg aacttgccgt acccgtccag   2220
cttgatgtta tacaccgacg ttaccttgtt aactatgtac gcccagtcaa aattaacgat   2280
gttgtagccg gtggcgaact cgggagagta ctgcttgaga aaggtcagga aggcaaccag   2340
cagctcgtac tcgctgtcaa actccaaaac cgtcggtctg ggctcgccgc gctggacgca   2400
tgcaaacgag tattcctcag agatatcgca tgacccgagg gaaaacagca gggtgtgttc   2460
gtggttctga gtagcaagcg agtacagcag acaggagatc tggatgacca ggtcctcttg   2520
gttagttgcc actgggaacg ccatttcgtt acccgttcca gctttacact ctatatcaaa   2580
gcacatgagc ttatagtcgg gccaggcagc ctcgtctggt atcggctcca ggttatcggg   2640
agtacagtta atctccacgt cgcttgaggt gacgtgtcgc tcaacggggc gaagttgaac   2700
acgctctccg tgggtgccgg gtcgcaggcg gtaccaccca aaactggtaa aattttcatt   2760
gtccaacaac agccgcgtgg tcacgtccac gctcccctcg aattttgtaa tctccgggtg   2820
aaagttgtcg cagatgaacc ctcccaggcg gctgctggag gcagatactc tatagtagag   2880
agctggctta gatccaaagt agtacagcgt cgtgtggcac acggtctcca ctttgaagca   2940
gtccgcagac acgtgctttc cgccccacca tcccccgccg ctgccgccgc tctgtttgcc   3000
gccgttgcca tttcccaggg ccgcgctcaa agccgagctg tgcgcgcagt ccaccattgc   3060
```

```
gcgcacgagt tctgcctcgg tggttattcc acaagcgcta tccacctccg cctttgccat   3120

gtaaaaataa tggcgcacac catagacgtg aaccgcgact cgctttccac actcgctcat   3180

tcccagcagt gttaccacag acccgcttgg gcgggatagc tcagcaaacc tggatgggtc   3240

atcgtgtgag gcgctctccg aagtctctac tatgtcgtac acgtgaaatc tctcaaatct   3300

ggggttgaat ccatcgcccc gaaaatcctg gccgttccaa acccgaatcc tgcgaggcca   3360

gcaacctccg gaggcaaagt tcagcacgtc gtactctgag ccatcgcagt acactttggg   3420

tgggcgctcc aaggtgccca cgtgtacacc gcgtcgctgg tcggcggggg cttcttcatc   3480

gaggcatctt ggagctataa acttaaagct acccacctct gtgcagtacg agtgttgggg   3540

gggccttggg cgctctgtct ccgcggtctg cccgcttccc ggcctgaaaa atggcctctt   3600

gccaataaac ggattaaaaa acccgctcct gcgaacggag ttggcctgtt cgcgcgccgc   3660

cat                                                                 3663
```

```
<210> SEQ ID NO 2
<211> LENGTH: 1220
<212> TYPE: PRT
<213> ORGANISM: artificial
<220> FEATURE:
<223> OTHER INFORMATION: EHV-1 DNA polymerase (pol) protein (AAS45914.1)
      encoded by AY464052 from EHV-1 V592 strain

<400> SEQUENCE: 2

Met Ala Ala Arg Glu Gln Ala Asn Ser Val Arg Arg Ser Gly Phe Phe
1               5                   10                  15

Asn Pro Phe Ile Gly Lys Arg Pro Phe Phe Arg Pro Gly Ser Gly Gln
            20                  25                  30

Thr Ala Glu Thr Glu Arg Pro Arg Pro Pro Gln His Ser Tyr Cys Thr
        35                  40                  45

Glu Val Gly Ser Phe Lys Phe Ile Ala Pro Arg Cys Leu Asp Glu Glu
    50                  55                  60

Ala Pro Ala Asp Gln Arg Arg Gly Val His Val Gly Thr Leu Glu Arg
65                  70                  75                  80

Pro Pro Lys Val Tyr Cys Asp Gly Ser Glu Tyr Asp Val Leu Asn Phe
                85                  90                  95

Ala Ser Gly Gly Cys Trp Pro Arg Arg Ile Arg Val Trp Asn Gly Gln
            100                 105                 110

Asp Phe Arg Gly Asp Gly Phe Asn Pro Arg Phe Glu Arg Phe His Val
        115                 120                 125

Tyr Asp Ile Val Glu Thr Ser Glu Ser Ala Ser His Asp Asp Pro Ser
    130                 135                 140

Arg Phe Ala Glu Leu Ser Arg Pro Ser Gly Ser Val Val Thr Leu Leu
145                 150                 155                 160

Gly Met Ser Glu Cys Gly Lys Arg Val Ala Val His Val Tyr Gly Val
                165                 170                 175

Arg His Tyr Phe Tyr Met Ala Lys Ala Glu Val Asp Ser Ala Cys Gly
            180                 185                 190

Ile Thr Thr Glu Ala Glu Leu Val Arg Ala Met Val Asp Cys Ala His
        195                 200                 205

Ser Ser Ala Leu Ser Ala Ala Leu Gly Asn Gly Asn Gly Gly Lys Gln
    210                 215                 220

Ser Gly Gly Ser Gly Gly Gly Trp Trp Gly Gly Lys His Val Ser Ala
225                 230                 235                 240
```

-continued

```
Asp Cys Phe Lys Val Glu Thr Val Cys His Thr Thr Leu Tyr Tyr Phe
                245                 250                 255

Gly Ser Lys Pro Ala Leu Tyr Tyr Arg Val Ser Ala Ser Ser Ser Arg
            260                 265                 270

Leu Gly Gly Phe Ile Cys Asp Asn Phe His Pro Glu Ile Thr Lys Phe
        275                 280                 285

Glu Gly Ser Val Asp Val Thr Thr Arg Leu Leu Leu Asp Asn Glu Asn
    290                 295                 300

Phe Thr Ser Phe Gly Trp Tyr Arg Leu Arg Pro Gly Thr His Gly Glu
305                 310                 315                 320

Arg Val Gln Leu Arg Pro Val Glu Arg His Val Thr Ser Ser Asp Val
                325                 330                 335

Glu Ile Asn Cys Thr Pro Asp Asn Leu Glu Pro Ile Pro Asp Glu Ala
            340                 345                 350

Ala Trp Pro Asp Tyr Lys Leu Met Cys Phe Asp Ile Glu Cys Lys Ala
        355                 360                 365

Gly Thr Gly Asn Glu Met Ala Phe Pro Val Ala Thr Asn Gln Glu Asp
    370                 375                 380

Leu Val Ile Gln Ile Ser Cys Leu Leu Tyr Ser Leu Ala Thr Gln Asn
385                 390                 395                 400

His Glu His Thr Leu Leu Phe Ser Leu Gly Ser Cys Asp Ile Ser Glu
                405                 410                 415

Glu Tyr Ser Phe Ala Cys Val Gln Arg Gly Glu Pro Arg Pro Thr Val
            420                 425                 430

Leu Glu Phe Asp Ser Glu Tyr Glu Leu Leu Val Ala Phe Leu Thr Phe
        435                 440                 445

Leu Lys Gln Tyr Ser Pro Glu Phe Ala Thr Gly Tyr Asn Ile Val Asn
    450                 455                 460

Phe Asp Trp Ala Tyr Ile Val Asn Lys Val Thr Ser Val Tyr Asn Ile
465                 470                 475                 480

Lys Leu Asp Gly Tyr Gly Lys Phe Asn Lys Gly Gly Leu Phe Lys Val
                485                 490                 495

Trp Asp Ile Ala Thr Asn His Phe Gln Lys Lys Ser Lys Val Lys Ile
            500                 505                 510

Asn Gly Leu Ile Ser Leu Asp Met Tyr Ser Val Ala Thr Glu Lys Leu
        515                 520                 525

Lys Leu Pro Ser Tyr Lys Leu Asp Ala Val Val Gly Asp Val Leu Gly
    530                 535                 540

Glu His Lys Ile Asp Leu Pro Tyr Lys Glu Ile Pro Ser Tyr Tyr Ala
545                 550                 555                 560

Gly Gly Pro Asp Arg Arg Gly Val Ile Gly Glu Tyr Cys Ile Gln Asp
                565                 570                 575

Ser Arg Leu Val Gly Lys Leu Phe Phe Lys Tyr Leu Pro His Leu Glu
            580                 585                 590

Leu Ser Ala Val Ala Lys Leu Ala Arg Ile Thr Leu Thr Arg Val Ile
        595                 600                 605

Phe Asp Gly Gln Gln Ile Arg Val Tyr Thr Cys Leu Leu Lys Leu Ala
    610                 615                 620

Arg Glu Arg Asn Phe Ile Leu Pro Asp Asn Arg Arg Arg Phe Asp Ser
625                 630                 635                 640

Gln Ala Asp Ala Ala Ser Glu Thr Ser Glu Leu Ala Met Asp Ser Gln
                645                 650                 655

Ser His Ala Phe Asp Ser Thr Asp Glu Pro Asp Gly Val Asp Gly Thr
```

```
            660                 665                 670

Pro Asp Ala Ala Gly Ser Gly Ala Thr Ser Glu Asn Gly Gly Gly Lys
        675                 680                 685

Pro Gly Val Gly Arg Ala Val Gly Tyr Gln Gly Ala Lys Val Leu Asp
    690                 695                 700

Pro Val Ser Gly Phe His Val Asp Pro Val Val Val Phe Asp Phe Ala
705                 710                 715                 720

Ser Leu Tyr Pro Ser Ile Ile Gln Ala His Asn Leu Cys Phe Thr Thr
                725                 730                 735

Leu Ala Leu Asp Glu Val Asp Leu Ala Gly Leu Gln Pro Ser Val Asn
            740                 745                 750

Tyr Ser Thr Phe Glu Val Gly Asp Gln Lys Leu Phe Phe Val His Ala
        755                 760                 765

His Ile Arg Glu Ser Leu Leu Gly Ile Leu Leu Arg Asp Trp Leu Ala
    770                 775                 780

Met Arg Lys Ala Val Arg Ala Arg Ile Pro Thr Ser Thr Pro Glu Glu
785                 790                 795                 800

Ala Val Leu Leu Asp Lys Gln Gln Ser Ala Ile Lys Val Ile Cys Asn
                805                 810                 815

Ser Val Tyr Gly Phe Thr Gly Val Ala Asn Gly Leu Leu Pro Cys Leu
            820                 825                 830

Arg Ile Ala Ala Thr Val Thr Thr Ile Gly Arg Asp Met Leu Leu Lys
        835                 840                 845

Thr Arg Asp Tyr Val His Ser Arg Trp Ala Thr Arg Glu Leu Leu Glu
    850                 855                 860

Asp Asn Phe Pro Gly Ala Ile Gly Phe Arg Asn His Lys Pro Tyr Ser
865                 870                 875                 880

Val Arg Val Ile Tyr Gly Asp Thr Asp Ser Val Phe Ile Lys Phe Val
                885                 890                 895

Gly Leu Thr Tyr Glu Gly Val Ser Glu Leu Gly Asp Ala Met Ser Arg
            900                 905                 910

Gln Ile Ser Ala Asp Leu Phe Arg Ala Pro Ile Lys Leu Glu Cys Glu
        915                 920                 925

Lys Thr Phe Gln Arg Leu Leu Leu Ile Thr Lys Lys Lys Tyr Ile Gly
    930                 935                 940

Val Ile Asn Gly Gly Lys Met Leu Met Lys Gly Val Asp Leu Val Arg
945                 950                 955                 960

Lys Asn Asn Cys Ser Phe Ile Asn Leu Tyr Ala Arg His Leu Val Asp
                965                 970                 975

Leu Leu Leu Tyr Asp Glu Asp Val Ala Thr Ala Ala Ala Lys Val Thr
            980                 985                 990

Asp Val Pro Pro Ala Glu Trp Val  Gly Arg Pro Leu Pro  Ser Gly Phe
        995                 1000                1005

Asp Lys  Phe Gly Arg Val Leu  Val Glu Ala Tyr Asn  Arg Ile Thr
    1010                1015                1020

Ala Pro  Asn Leu Asp Val Arg  Glu Phe Val Met Thr  Ala Glu Leu
    1025                1030                1035

Ser Arg  Ser Pro Glu Ser Tyr  Thr Asn Lys Arg Leu  Pro His Leu
    1040                1045                1050

Thr Val  Tyr Phe Lys Leu Ala  Met Arg Asn Glu Glu  Leu Pro Ser
    1055                1060                1065

Val Lys  Glu Arg Ile Pro Tyr  Val Ile Val Ala Gln  Thr Glu Ala
    1070                1075                1080
```

-continued

```
Ala Glu  Arg Glu Ala Gly Val  Val Asn Ser Met Arg  Gly Thr Ala
    1085                 1090                 1095

Gln Asn  Pro Val Val Thr Lys  Thr Ala Arg Pro Gln  Pro Lys Arg
    1100                 1105                 1110

Lys Leu  Leu Val Ser Asp Leu  Ala Glu Asp Pro Thr  Tyr Val Ser
    1115                 1120                 1125

Glu Asn  Asp Val Pro Leu Asn  Thr Asp Tyr Tyr Phe  Ser His Leu
    1130                 1135                 1140

Leu Gly  Thr Ile Ser Val Thr  Phe Lys Ala Leu Phe  Gly Asn Asp
    1145                 1150                 1155

Val Arg  Thr Thr Glu Asn Leu  Leu Lys Arg Phe Ile  Pro Glu Thr
    1160                 1165                 1170

Pro His  Lys Thr Pro Thr Lys  Thr Gln Ala Leu Leu  Glu Arg Ala
    1175                 1180                 1185

Gly Phe  Glu Lys Leu Thr Pro  Phe Thr Pro Glu Glu  Glu Ser Arg
    1190                 1195                 1200

Arg Ile  Leu His Thr Val Phe  Cys Thr Leu Glu Ala  Ala Pro His
    1205                 1210                 1215

Gln Ser
    1220
```

<210> SEQ ID NO 3
<211> LENGTH: 3663
<212> TYPE: DNA
<213> ORGANISM: artificial
<220> FEATURE:
<223> OTHER INFORMATION: EHV-1 DNA polymerase (Pol) (AY665713) from
      EHV-1 Ab4 strain

<400> SEQUENCE: 3

```
tcagctttga tggggagctg cttctagagt acaaaaaact gtatgcagta ttcgacgact     60

ttcttcctcc ggtgtaaagg gcgtcagctt ttcaaagccg gcgcgctcaa gcagtgcctg    120

ggttttcgtg ggggtcttgt ggggggtttc cggaataaac cgctttaaaa gattttctgt    180

tgttctcaca tcatttccga atagagcctt aaaggtcacg cttatggtac ccaacaggtg    240

ggagaaatag tagtctgtgt ttagcggtac gtcattctcg gaaacatagg tcgggtcttc    300

ggcgaggtcg gaaaccagca gtttgcgttt aggttggggg cgtgcggtct tggttaccac    360

ggggttttgg gcggtaccgc gcattgagtt tactacaccc gcttcgcgtt ccgcggcctc    420

ggtctgcgca actatcacat acggaattct ctcttttacg ctgggcagtt cttcattcct    480

catggcgagc ttaaagtaga cggtgaggtg cggcaggcgc ttgttggtat acgattcggg    540

tgagcggctc agctcagcag tcataacgaa ctcgcgcacg tccaagttgg gggcagtgat    600

acggttgtac gcctctacca gcactcgccc aaacttgtca aagccgctcg gtagcgggcg    660

ccccacccat tctgcgggag gcacgtctgt cacctctgct gccgccgtgg ccacatcctc    720

gtcgtacaac aaaagatcta ccagatgtcg cgcgtacaag tttatgaaag agcagttatt    780

tttgcggacc aggtcgaccc ccttcatgag catcttcccc ccgtttatga cacctatgta    840

cttcttcttg gtgatcagca gcagtcgctg aaaggtcttc tcacactcca gtttgatggg    900

cgctctaaag aggtccgctg aaatctgacg cgacatagca tcccccagct ccgataccc c   960

ctcgtacgtc aggcccacaa acttgataaa cacggagtcg gtgtctccgt agataaccct   1020

gacggagtaa ggcttgtggt ttcggaaacc tatagcccct ggaaaattgt cctccagcag   1080

ctcgcgcgtc gcccaacgag agtgaacgta atctcgggtc ttgaggagca tgtcgcgtcc   1140
```

-continued

```
tatcgtggta acggtagccg ctatcctcag acacggcaac aggccgtttg ccaccccegt   1200

gaatccgtaa accgagttgc atatcacctt aatcgcagac tgctgcttat ctagtaaaac   1260

tgcctcctcg gggtgctgg tggggattcg cgccctcacc gcctttcgca tggccagcca   1320

gtcgcgcagc aagatgccaa gcaggctttc gcgaatatgg gcgtggacaa aaaataactt   1380

ttggtcaccc acctcgaacg tcgagtagtc gacggatggt tgaagcccgg ccagatccac   1440

ttcatcgagc gccagggtgg tgaaacagag gttatgggcc tggataatgc ttgggtataa   1500

gctagcgaag tcaaacacaa ccacggggtc cacatgaaag ccggatacgg ggtctagaac   1560

ctttgctccc tggtagccca cggccctccc gacgccgggc ttcccgcctc cgttttcaga   1620

agtagcgcca gatcctgcgg cgtccggggt accgtccaca ccgtcgggtt cgtctgtact   1680

gtcgaaggcg tggctttggc tatccatagc caactccgaa gtctctgacg cggcgtctgc   1740

ctgactgtca aaccggcgtc tgttgtctgg caaaatgaaa tttctctcgc gggcgagttt   1800

cagcaagcac gtgtacacgc gaatttgctg accgtcaaaa attacccgcg ttagggtgat   1860

acgggcgagt ttggccaccg ccgatagttc cagatggggg aggtacttaa aaaacagctt   1920

gcccaccagc ctagagtcct ggatacaata ctctcctatt acgcccctcc ggtcaggccc   1980

tcccgcgtaa taggagggta tttctttata gggaaggtct atcttatgct cgccgaggac   2040

gtctcccacg accgcgtcga gtttgtagct gggtagcttt agcttttccg tcgccacaga   2100

atacatgtct agagatatca ggccattgat tttcaccttg ctcttcttct gaaaatggtt   2160

cgtggcgatg tcccacacct taaacagccc ccctttgttg aacttgccgt acccgtccag   2220

cttgatgtta tacaccgacg ttaccttgtt aactatgtac gcccagtcaa aattaacgat   2280

gttgtagccg gtggcgaact cgggagagta ctgcttgaga aaggtcagga aggcaaccag   2340

cagctcgtac tcgctgtcaa actccaaaac cgtcggtctg ggctcgccgc gctggacgca   2400

tgcaaacgag tattcctcag agatatcgca tgacccgagg gaaaacagca gggtgtgttc   2460

gtggttctga gtagcaagcg agtacagcag acaggagatc tggatgacca ggtcctcttg   2520

gttagttgcc actgggaacg ccatttcgtt acccgttcca gctttacact ctatatcaaa   2580

gcacatgagc ttatagtcgg gccaggcagc ctcgtctggt atcggctcca ggttatcggg   2640

agtacagtta atctccacgt cgcttgaggt gacgtgtcgc tcaacggggc gaagttgaac   2700

acgctctccg tgggtgccgg gtcgcaggcg gtaccacccg aaactggtaa aattttcatt   2760

gtccaacaac agccgcgtgg tcacgtccac gctcccctcg aattttgtaa tctccgggtg   2820

aaagttgtcg cagatgaacc ctcccaggcg gctgctggag gcagatactc tatagtagag   2880

agctggctta gatccaaagt agtacagcgt cgtgtggcac acggtctcca ctttgaagca   2940

gtccgcagac acgtgctttc cgccccacca tcccccgccg ctgccgccgc tctgtttgcc   3000

gccgttgcca tttcccaggg ccgcgctcaa agccgagctg tgcgcgcagt ccaccattgc   3060

gcgcacgagt tctgcctcgg tggttattcc acaagcgcta tccacctccg cctttgccat   3120

gtaaaaataa tggcgcacac catagacgtg aaccgcgact cgctttccac actcgctcat   3180

tcccagcagt gttaccacag acccgcttgg gcgggatagc tcagcaaacc tggatgggtc   3240

atcgtgtgag gcgctctccg aagtctctac tatgtcgtac acgtgaaatc tctcaaatct   3300

ggggttgaat ccatcgcccc gaaaatcctg gccgttccaa acccgaatcc tgcgaggcca   3360

gcaacctccg gaggcaaagt tcagcacgtc gtactctgag ccatcgcagt acactttggg   3420

tgggcgctcc aaggtgccca cgtgtacacc gcgtcgctgg tcggcggggg cttcttcatc   3480
```

-continued

```
gaggcatctt ggagctataa acttaaagct acccacctct gtgcagtacg agtgttgggg   3540

gggccttggg cgctctgtct ccgcggtctg cccgcttccc ggcctgaaaa atggcctctt   3600

gccaataaac ggattaaaaa acccgctcct gcgaacggag ttggcctgtt cgcgcgccgc   3660

cat                                                                 3663


<210> SEQ ID NO 4
<211> LENGTH: 1220
<212> TYPE: PRT
<213> ORGANISM: artificial
<220> FEATURE:
<223> OTHER INFORMATION: EHV-1 DNA polymerase (pol) protein (AAT67287.1)
      encoded by AY665713 from EHV-1 Ab4 strain

<400> SEQUENCE: 4

Met Ala Ala Arg Glu Gln Ala Asn Ser Val Arg Arg Ser Gly Phe Phe
1               5                   10                  15

Asn Pro Phe Ile Gly Lys Arg Pro Phe Phe Arg Pro Gly Ser Gly Gln
            20                  25                  30

Thr Ala Glu Thr Glu Arg Pro Arg Pro Pro Gln His Ser Tyr Cys Thr
        35                  40                  45

Glu Val Gly Ser Phe Lys Phe Ile Ala Pro Arg Cys Leu Asp Glu Glu
    50                  55                  60

Ala Pro Ala Asp Gln Arg Arg Gly Val His Val Gly Thr Leu Glu Arg
65                  70                  75                  80

Pro Pro Lys Val Tyr Cys Asp Gly Ser Glu Tyr Asp Val Leu Asn Phe
                85                  90                  95

Ala Ser Gly Gly Cys Trp Pro Arg Arg Ile Arg Val Trp Asn Gly Gln
            100                 105                 110

Asp Phe Arg Gly Asp Gly Phe Asn Pro Arg Phe Glu Arg Phe His Val
        115                 120                 125

Tyr Asp Ile Val Glu Thr Ser Glu Ser Ala Ser His Asp Asp Pro Ser
    130                 135                 140

Arg Phe Ala Glu Leu Ser Arg Pro Ser Gly Ser Val Val Thr Leu Leu
145                 150                 155                 160

Gly Met Ser Glu Cys Gly Lys Arg Val Ala Val His Val Tyr Gly Val
                165                 170                 175

Arg His Tyr Phe Tyr Met Ala Lys Ala Glu Val Asp Ser Ala Cys Gly
            180                 185                 190

Ile Thr Thr Glu Ala Glu Leu Val Arg Ala Met Val Asp Cys Ala His
        195                 200                 205

Ser Ser Ala Leu Ser Ala Ala Leu Gly Asn Gly Asn Gly Gly Lys Gln
    210                 215                 220

Ser Gly Gly Ser Gly Gly Gly Trp Trp Gly Gly Lys His Val Ser Ala
225                 230                 235                 240

Asp Cys Phe Lys Val Glu Thr Val Cys His Thr Thr Leu Tyr Tyr Phe
                245                 250                 255

Gly Ser Lys Pro Ala Leu Tyr Tyr Arg Val Ser Ala Ser Ser Ser Arg
            260                 265                 270

Leu Gly Gly Phe Ile Cys Asp Asn Phe His Pro Glu Ile Thr Lys Phe
        275                 280                 285

Glu Gly Ser Val Asp Val Thr Thr Arg Leu Leu Leu Asp Asn Glu Asn
    290                 295                 300

Phe Thr Ser Phe Gly Trp Tyr Arg Leu Arg Pro Gly Thr His Gly Glu
305                 310                 315                 320
```

-continued

```
Arg Val Gln Leu Arg Pro Val Glu Arg His Val Thr Ser Ser Asp Val
                325                 330                 335

Glu Ile Asn Cys Thr Pro Asp Asn Leu Glu Pro Ile Pro Asp Glu Ala
            340                 345                 350

Ala Trp Pro Asp Tyr Lys Leu Met Cys Phe Asp Ile Glu Cys Lys Ala
        355                 360                 365

Gly Thr Gly Asn Glu Met Ala Phe Pro Val Ala Thr Asn Gln Glu Asp
    370                 375                 380

Leu Val Ile Gln Ile Ser Cys Leu Leu Tyr Ser Leu Ala Thr Gln Asn
385                 390                 395                 400

His Glu His Thr Leu Leu Phe Ser Leu Gly Ser Cys Asp Ile Ser Glu
                405                 410                 415

Glu Tyr Ser Phe Ala Cys Val Gln Arg Gly Glu Pro Arg Pro Thr Val
            420                 425                 430

Leu Glu Phe Asp Ser Glu Tyr Glu Leu Leu Val Ala Phe Leu Thr Phe
        435                 440                 445

Leu Lys Gln Tyr Ser Pro Glu Phe Ala Thr Gly Tyr Asn Ile Val Asn
    450                 455                 460

Phe Asp Trp Ala Tyr Ile Val Asn Lys Val Thr Ser Val Tyr Asn Ile
465                 470                 475                 480

Lys Leu Asp Gly Tyr Gly Lys Phe Asn Lys Gly Gly Leu Phe Lys Val
                485                 490                 495

Trp Asp Ile Ala Thr Asn His Phe Gln Lys Lys Ser Lys Val Lys Ile
            500                 505                 510

Asn Gly Leu Ile Ser Leu Asp Met Tyr Ser Val Ala Thr Glu Lys Leu
        515                 520                 525

Lys Leu Pro Ser Tyr Lys Leu Asp Ala Val Val Gly Asp Val Leu Gly
    530                 535                 540

Glu His Lys Ile Asp Leu Pro Tyr Lys Glu Ile Pro Ser Tyr Tyr Ala
545                 550                 555                 560

Gly Gly Pro Asp Arg Arg Gly Val Ile Gly Glu Tyr Cys Ile Gln Asp
                565                 570                 575

Ser Arg Leu Val Gly Lys Leu Phe Phe Lys Tyr Leu Pro His Leu Glu
            580                 585                 590

Leu Ser Ala Val Ala Lys Leu Ala Arg Ile Thr Leu Thr Arg Val Ile
        595                 600                 605

Phe Asp Gly Gln Gln Ile Arg Val Tyr Thr Cys Leu Leu Lys Leu Ala
    610                 615                 620

Arg Glu Arg Asn Phe Ile Leu Pro Asp Asn Arg Arg Arg Phe Asp Ser
625                 630                 635                 640

Gln Ala Asp Ala Ala Ser Glu Thr Ser Glu Leu Ala Met Asp Ser Gln
                645                 650                 655

Ser His Ala Phe Asp Ser Thr Asp Glu Pro Asp Gly Val Asp Gly Thr
            660                 665                 670

Pro Asp Ala Ala Gly Ser Gly Ala Thr Ser Glu Asn Gly Gly Gly Lys
        675                 680                 685

Pro Gly Val Gly Arg Ala Val Gly Tyr Gln Gly Ala Lys Val Leu Asp
    690                 695                 700

Pro Val Ser Gly Phe His Val Asp Pro Val Val Val Phe Asp Phe Ala
705                 710                 715                 720

Ser Leu Tyr Pro Ser Ile Ile Gln Ala His Asn Leu Cys Phe Thr Thr
                725                 730                 735

Leu Ala Leu Asp Glu Val Asp Leu Ala Gly Leu Gln Pro Ser Val Asp
```

-continued

```
            740                 745                 750

Tyr Ser Thr Phe Glu Val Gly Asp Gln Lys Leu Phe Phe Val His Ala
        755                 760                 765

His Ile Arg Glu Ser Leu Leu Gly Ile Leu Leu Arg Asp Trp Leu Ala
    770                 775                 780

Met Arg Lys Ala Val Arg Ala Arg Ile Pro Thr Ser Thr Pro Glu Glu
785                 790                 795                 800

Ala Val Leu Leu Asp Lys Gln Gln Ser Ala Ile Lys Val Ile Cys Asn
                805                 810                 815

Ser Val Tyr Gly Phe Thr Gly Val Ala Asn Gly Leu Leu Pro Cys Leu
            820                 825                 830

Arg Ile Ala Ala Thr Val Thr Thr Ile Gly Arg Asp Met Leu Leu Lys
        835                 840                 845

Thr Arg Asp Tyr Val His Ser Arg Trp Ala Thr Arg Glu Leu Leu Glu
    850                 855                 860

Asp Asn Phe Pro Gly Ala Ile Gly Phe Arg Asn His Lys Pro Tyr Ser
865                 870                 875                 880

Val Arg Val Ile Tyr Gly Asp Thr Asp Ser Val Phe Ile Lys Phe Val
                885                 890                 895

Gly Leu Thr Tyr Glu Gly Val Ser Glu Leu Gly Asp Ala Met Ser Arg
            900                 905                 910

Gln Ile Ser Ala Asp Leu Phe Arg Ala Pro Ile Lys Leu Glu Cys Glu
        915                 920                 925

Lys Thr Phe Gln Arg Leu Leu Leu Ile Thr Lys Lys Lys Tyr Ile Gly
    930                 935                 940

Val Ile Asn Gly Gly Lys Met Leu Met Lys Gly Val Asp Leu Val Arg
945                 950                 955                 960

Lys Asn Asn Cys Ser Phe Ile Asn Leu Tyr Ala Arg His Leu Val Asp
                965                 970                 975

Leu Leu Leu Tyr Asp Glu Asp Val Ala Thr Ala Ala Ala Glu Val Thr
            980                 985                 990

Asp Val Pro Pro Ala Glu Trp Val  Gly Arg Pro Leu Pro  Ser Gly Phe
        995                 1000                1005

Asp Lys  Phe Gly Arg Val Leu  Val Glu Ala Tyr Asn  Arg Ile Thr
    1010                1015                1020

Ala Pro  Asn Leu Asp Val Arg  Glu Phe Val Met Thr  Ala Glu Leu
    1025                1030                1035

Ser Arg  Ser Pro Glu Ser Tyr  Thr Asn Lys Arg Leu  Pro His Leu
    1040                1045                1050

Thr Val  Tyr Phe Lys Leu Ala  Met Arg Asn Glu Glu  Leu Pro Ser
    1055                1060                1065

Val Lys  Glu Arg Ile Pro Tyr  Val Ile Val Ala Gln  Thr Glu Ala
    1070                1075                1080

Ala Glu  Arg Glu Ala Gly Val  Val Asn Ser Met Arg  Gly Thr Ala
    1085                1090                1095

Gln Asn  Pro Val Val Thr Lys  Thr Ala Arg Pro Gln  Pro Lys Arg
    1100                1105                1110

Lys Leu  Leu Val Ser Asp Leu  Ala Glu Asp Pro Thr  Tyr Val Ser
    1115                1120                1125

Glu Asn  Asp Val Pro Leu Asn  Thr Asp Tyr Tyr Phe  Ser His Leu
    1130                1135                1140

Leu Gly  Thr Ile Ser Val Thr  Phe Lys Ala Leu Phe  Gly Asn Asp
    1145                1150                1155
```

```
Val Arg  Thr Thr Glu Asn Leu  Leu Lys Arg Phe Ile  Pro Glu Thr
    1160                 1165                 1170

Pro His  Lys Thr Pro Thr Lys  Thr Gln Ala Leu Leu  Glu Arg Ala
    1175                 1180                 1185

Gly Phe  Glu Lys Leu Thr Pro  Phe Thr Pro Glu Glu  Glu Ser Arg
    1190                 1195                 1200

Arg Ile  Leu His Thr Val Phe  Cys Thr Leu Glu Ala  Ala Pro His
    1205                 1210                 1215

Gln Ser
    1220


<210> SEQ ID NO 5
<211> LENGTH: 3663
<212> TYPE: DNA
<213> ORGANISM: artificial sequence
<220> FEATURE:
<223> OTHER INFORMATION: EHV-1 DNA polymerase (Pol) (NC_001491) from
      EHV-1

<400> SEQUENCE: 5

tcagctttga tggggagctg cttctagagt acaaaaaact gtatgcagta ttcgacgact     60

ttcttcctcc ggtgtaaagg gcgtcagctt ttcaaagccg gcgcgctcaa gcagtgcctg    120

ggttttcgtg gggtcttgt gggggtttc cggaataaac cgctttaaaa gattttctgt    180

tgttctcaca tcatttccga atagagcctt aaaggtcacg cttatggtac ccaacaggtg    240

ggagaaatag tagtctgtgt ttagcggtac gtcattctcg gaaacatagg tcgggtcttc    300

ggcgaggtcg gaaaccagca gtttgcgttt aggttggggg cgtgcggtct tggttaccac    360

ggggttttgg gcggtaccgc gcattgagtt tactacaccc gcttcgcgtt ccgcggcctc    420

ggtctgcgca actatcacat acggaattct ctcttttacg ctgggcagtt cttcattcct    480

catggcgagc ttaaagtaga cggtgaggtg cggcaggcgc ttgttggtat acgattcggg    540

tgagcggctc agctcagcag tcataacgaa ctcgcgcacg tccaagttgg gggcagtgat    600

acggttgtac gcctctacca gcactcgccc aaacttgtca aagccgctcg gtagcgggcg    660

ccccacccat tctgcgggag gcacgtctgt cacctctgct gccgccgtgg ccacatcctc    720

gtcgtacaac aaaagatcta ccagatgtcg cgcgtacaag tttatgaaag agcagttatt    780

tttgcggacc aggtcgaccc ccttcatgag catcttcccc ccgtttatga cacctatgta    840

cttcttcttg gtgatcagca gcagtcgctg aaaggtcttc tcacactcca gtttgatggg    900

cgctctaaag aggtccgctg aaatctgacg cgacatagca tcccccagct ccgataccc    960

ctcgtacgtc aggcccacaa acttgataaa cacggagtcg gtgtctccgt agataaccct   1020

gacggagtaa ggcttgtggt ttcggaaacc tatagcccct ggaaaattgt cctccagcag   1080

ctcgcgcgtc gcccaacgag agtgaacgta atctcgggtc ttgaggagca tgtcgcgtcc   1140

tatcgtggta acggtagccg ctatcctcag acacggcaac aggccgtttg ccacccccgt   1200

gaatccgtaa accgagttgc atatcacctt aatcgcagac tgctgcttat ctagtaaaac   1260

tgcctcctcg ggggtgctgg tggggattcg cgccctcacc gcctttcgca tggccagcca   1320

gtcgcgcagc aagatgccaa gcaggctttc gcgaatatgg gcgtggacaa aaaataactt   1380

ttggtcaccc acctcgaacg tcgagtagtc gacggatggt tgaagcccgg ccagatccac   1440

ttcatcgagc gccagggtgg tgaaacagag gttatgggcc tggataatgc ttgggtataa   1500

gctagcgaag tcaaacacaa ccacggggtc cacatgaaag ccggatacgg ggtctagaac   1560
```

-continued

```
ctttgctccc tggtagccca cggccctccc gacgccgggc ttcccgcctc cgttttcaga   1620
agtagcgcca gatcctgcgg cgtccggggt accgtccaca ccgtcgggtt cgtctgtact   1680
gtcgaaggcg tggctttggc tatccatagc caactccgaa gtctctgacg cggcgtctgc   1740
ctgactgtca aaccggcgtc tgttgtctgg caaaatgaaa tttctctcgc gggcgagttt   1800
cagcaagcac gtgtacacgc gaatttgctg accgtcaaaa attacccgcg ttagggtgat   1860
acgggcgagt ttggccaccg ccgatagttc cagatggggg aggtacttaa aaaacagctt   1920
gcccaccagc ctagagtcct ggatacaata ctctcctatt acgcccctcc ggtcaggccc   1980
tcccgcgtaa taggagggta tttctttata gggaaggtct atcttatgct cgccgaggac   2040
gtctcccacg accgcgtcga gtttgtagct gggtagcttt agcttttccg tcgccacaga   2100
atacatgtct agagatatca ggccattgat tttcaccttg ctcttcttct gaaaatggtt   2160
cgtggcgatg tcccacacct taaacagccc ccctttgttg aacttgccgt acccgtccag   2220
cttgatgtta tacaccgacg ttaccttgtt aactatgtac gcccagtcaa aattaacgat   2280
gttgtagccg gtggcgaact cgggagagta ctgcttgaga aaggtcagga aggcaaccag   2340
cagctcgtac tcgctgtcaa actccaaaac cgtcggtctg ggctcgccgc gctggacgca   2400
tgcaaacgag tattcctcag agatatcgca tgacccgagg gaaaacagca gggtgtgttc   2460
gtggttctga gtagcaagcg agtacagcag acaggagatc tggatgacca ggtcctcttg   2520
gttagttgcc actgggaacg ccatttcgtt acccgttcca gctttacact ctatatcaaa   2580
gcacatgagc ttatagtcgg gccaggcagc ctcgtctggt atcggctcca ggttatcggg   2640
agtacagtta atctccacgt cgcttgaggt gacgtgtcgc tcaacggggc gaagttgaac   2700
acgctctccg tgggtgccgg gtcgcaggcg gtaccacccg aaactggtaa aattttcatt   2760
gtccaacaac agccgcgtgg tcacgtccac gctcccctcg aattttgtaa tctccgggtg   2820
aaagttgtcg cagatgaacc ctcccaggcg gctgctggag gcagatactc tatagtagag   2880
agctggctta gatccaaagt agtacagcgt cgtgtggcac acggtctcca ctttgaagca   2940
gtccgcagac acgtgctttc cgccccacca tcccccgccg ctgccgccgc tctgtttgcc   3000
gccgttgcca tttcccaggg ccgcgctcaa agccgagctg tgcgcgcagt ccaccattgc   3060
gcgcacgagt tctgcctcgg tggttattcc acaagcgcta tccacctccg cctttgccat   3120
gtaaaaataa tggcgcacac catagacgtg aaccgcgact cgctttccac actcgctcat   3180
tcccagcagt gttaccacag acccgcttgg gcgggatagc tcagcaaacc tggatgggtc   3240
atcgtgtgag gcgctctccg aagtctctac tatgtcgtac acgtgaaatc tctcaaatct   3300
ggggttgaat ccatcgcccc gaaaatcctg gccgttccaa acccgaatcc tgcgaggcca   3360
gcaacctccg gaggcaaagt tcagcacgtc gtactctgag ccatcgcagt acactttggg   3420
tgggcgctcc aaggtgccca cgtgtacacc gcgtcgctgg tcggcggggg cttcttcatc   3480
gaggcatctt ggagctataa acttaaagct acccacctct gtgcagtacg agtgttgggg   3540
gggccttggg cgctctgtct ccgcggtctg cccgcttccc ggcctgaaaa atggcctctt   3600
gccaataaac ggattaaaaa acccgctcct gcgaacggag ttggcctgtt cgcgcgccgc   3660
cat                                                                 3663
```

<210> SEQ ID NO 6
<211> LENGTH: 1220
<212> TYPE: PRT
<213> ORGANISM: artificial sequence
<220> FEATURE:
<223> OTHER INFORMATION: EHV-1 DNA polymerase (YP_053075.1) encoded by -continued

NC_001491

<400> SEQUENCE: 6

```
Met Ala Ala Arg Glu Gln Ala Asn Ser Val Arg Arg Ser Gly Phe Phe
1               5                   10                  15

Asn Pro Phe Ile Gly Lys Arg Pro Phe Phe Arg Pro Gly Ser Gly Gln
            20                  25                  30

Thr Ala Glu Thr Glu Arg Pro Arg Pro Pro Gln His Ser Tyr Cys Thr
        35                  40                  45

Glu Val Gly Ser Phe Lys Phe Ile Ala Pro Arg Cys Leu Asp Glu Glu
    50                  55                  60

Ala Pro Ala Asp Gln Arg Arg Gly Val His Val Gly Thr Leu Glu Arg
65                  70                  75                  80

Pro Pro Lys Val Tyr Cys Asp Gly Ser Glu Tyr Asp Val Leu Asn Phe
                85                  90                  95

Ala Ser Gly Gly Cys Trp Pro Arg Arg Ile Arg Val Trp Asn Gly Gln
            100                 105                 110

Asp Phe Arg Gly Asp Gly Phe Asn Pro Arg Phe Glu Arg Phe His Val
        115                 120                 125

Tyr Asp Ile Val Glu Thr Ser Glu Ser Ala Ser His Asp Asp Pro Ser
    130                 135                 140

Arg Phe Ala Glu Leu Ser Arg Pro Ser Gly Ser Val Val Thr Leu Leu
145                 150                 155                 160

Gly Met Ser Glu Cys Gly Lys Arg Val Ala Val His Val Tyr Gly Val
                165                 170                 175

Arg His Tyr Phe Tyr Met Ala Lys Ala Glu Val Asp Ser Ala Cys Gly
            180                 185                 190

Ile Thr Thr Glu Ala Glu Leu Val Arg Ala Met Val Asp Cys Ala His
        195                 200                 205

Ser Ser Ala Leu Ser Ala Ala Leu Gly Asn Gly Asn Gly Gly Lys Gln
    210                 215                 220

Ser Gly Gly Ser Gly Gly Gly Trp Trp Gly Gly Lys His Val Ser Ala
225                 230                 235                 240

Asp Cys Phe Lys Val Glu Thr Val Cys His Thr Thr Leu Tyr Tyr Phe
                245                 250                 255

Gly Ser Lys Pro Ala Leu Tyr Tyr Arg Val Ser Ala Ser Ser Ser Arg
            260                 265                 270

Leu Gly Gly Phe Ile Cys Asp Asn Phe His Pro Glu Ile Thr Lys Phe
        275                 280                 285

Glu Gly Ser Val Asp Val Thr Thr Arg Leu Leu Leu Asp Asn Glu Asn
    290                 295                 300

Phe Thr Ser Phe Gly Trp Tyr Arg Leu Arg Pro Gly Thr His Gly Glu
305                 310                 315                 320

Arg Val Gln Leu Arg Pro Val Glu Arg His Val Thr Ser Ser Asp Val
                325                 330                 335

Glu Ile Asn Cys Thr Pro Asp Asn Leu Glu Pro Ile Pro Asp Glu Ala
            340                 345                 350

Ala Trp Pro Asp Tyr Lys Leu Met Cys Phe Asp Ile Glu Cys Lys Ala
        355                 360                 365

Gly Thr Gly Asn Glu Met Ala Phe Pro Val Ala Thr Asn Gln Glu Asp
    370                 375                 380

Leu Val Ile Gln Ile Ser Cys Leu Leu Tyr Ser Leu Ala Thr Gln Asn
385                 390                 395                 400
```

-continued

```
His Glu His Thr Leu Leu Phe Ser Leu Gly Ser Cys Asp Ile Ser Glu
                405                 410                 415

Glu Tyr Ser Phe Ala Cys Val Gln Arg Gly Glu Pro Arg Pro Thr Val
            420                 425                 430

Leu Glu Phe Asp Ser Glu Tyr Glu Leu Leu Val Ala Phe Leu Thr Phe
        435                 440                 445

Leu Lys Gln Tyr Ser Pro Glu Phe Ala Thr Gly Tyr Asn Ile Val Asn
    450                 455                 460

Phe Asp Trp Ala Tyr Ile Val Asn Lys Val Thr Ser Val Tyr Asn Ile
465                 470                 475                 480

Lys Leu Asp Gly Tyr Gly Lys Phe Asn Lys Gly Gly Leu Phe Lys Val
                485                 490                 495

Trp Asp Ile Ala Thr Asn His Phe Gln Lys Lys Ser Lys Val Lys Ile
            500                 505                 510

Asn Gly Leu Ile Ser Leu Asp Met Tyr Ser Val Ala Thr Glu Lys Leu
        515                 520                 525

Lys Leu Pro Ser Tyr Lys Leu Asp Ala Val Val Gly Asp Val Leu Gly
    530                 535                 540

Glu His Lys Ile Asp Leu Pro Tyr Lys Glu Ile Pro Ser Tyr Tyr Ala
545                 550                 555                 560

Gly Gly Pro Asp Arg Arg Gly Val Ile Gly Glu Tyr Cys Ile Gln Asp
                565                 570                 575

Ser Arg Leu Val Gly Lys Leu Phe Phe Lys Tyr Leu Pro His Leu Glu
            580                 585                 590

Leu Ser Ala Val Ala Lys Leu Ala Arg Ile Thr Leu Thr Arg Val Ile
        595                 600                 605

Phe Asp Gly Gln Gln Ile Arg Val Tyr Thr Cys Leu Leu Lys Leu Ala
    610                 615                 620

Arg Glu Arg Asn Phe Ile Leu Pro Asp Asn Arg Arg Arg Phe Asp Ser
625                 630                 635                 640

Gln Ala Asp Ala Ala Ser Glu Thr Ser Glu Leu Ala Met Asp Ser Gln
                645                 650                 655

Ser His Ala Phe Asp Ser Thr Asp Glu Pro Asp Gly Val Asp Gly Thr
            660                 665                 670

Pro Asp Ala Ala Gly Ser Gly Ala Thr Ser Glu Asn Gly Gly Gly Lys
        675                 680                 685

Pro Gly Val Gly Arg Ala Val Gly Tyr Gln Gly Ala Lys Val Leu Asp
    690                 695                 700

Pro Val Ser Gly Phe His Val Asp Pro Val Val Val Phe Asp Phe Ala
705                 710                 715                 720

Ser Leu Tyr Pro Ser Ile Ile Gln Ala His Asn Leu Cys Phe Thr Thr
                725                 730                 735

Leu Ala Leu Asp Glu Val Asp Leu Ala Gly Leu Gln Pro Ser Val Asp
            740                 745                 750

Tyr Ser Thr Phe Glu Val Gly Asp Gln Lys Leu Phe Phe Val His Ala
        755                 760                 765

His Ile Arg Glu Ser Leu Leu Gly Ile Leu Leu Arg Asp Trp Leu Ala
    770                 775                 780

Met Arg Lys Ala Val Arg Ala Arg Ile Pro Thr Ser Thr Pro Glu Glu
785                 790                 795                 800

Ala Val Leu Leu Asp Lys Gln Gln Ser Ala Ile Lys Val Ile Cys Asn
                805                 810                 815

Ser Val Tyr Gly Phe Thr Gly Val Ala Asn Gly Leu Leu Pro Cys Leu
```

-continued

```
        820                 825                 830

Arg Ile Ala Ala Thr Val Thr Thr Ile Gly Arg Asp Met Leu Leu Lys
    835                 840                 845

Thr Arg Asp Tyr Val His Ser Arg Trp Ala Thr Arg Glu Leu Leu Glu
    850                 855                 860

Asp Asn Phe Pro Gly Ala Ile Gly Phe Arg Asn His Lys Pro Tyr Ser
865                 870                 875                 880

Val Arg Val Ile Tyr Gly Asp Thr Asp Ser Val Phe Ile Lys Phe Val
                885                 890                 895

Gly Leu Thr Tyr Glu Gly Val Ser Glu Leu Gly Asp Ala Met Ser Arg
            900                 905                 910

Gln Ile Ser Ala Asp Leu Phe Arg Ala Pro Ile Lys Leu Glu Cys Glu
        915                 920                 925

Lys Thr Phe Gln Arg Leu Leu Leu Ile Thr Lys Lys Lys Tyr Ile Gly
    930                 935                 940

Val Ile Asn Gly Gly Lys Met Leu Met Lys Gly Val Asp Leu Val Arg
945                 950                 955                 960

Lys Asn Asn Cys Ser Phe Ile Asn Leu Tyr Ala Arg His Leu Val Asp
                965                 970                 975

Leu Leu Leu Tyr Asp Glu Asp Val Ala Thr Ala Ala Ala Glu Val Thr
            980                 985                 990

Asp Val Pro Pro Ala Glu Trp Val  Gly Arg Pro Leu Pro  Ser Gly Phe
        995                 1000                1005

Asp Lys  Phe Gly Arg Val Leu  Val Glu Ala Tyr Asn  Arg Ile Thr
    1010                 1015                 1020

Ala Pro  Asn Leu Asp Val Arg  Glu Phe Val Met Thr  Ala Glu Leu
    1025                 1030                 1035

Ser Arg  Ser Pro Glu Ser Tyr  Thr Asn Lys Arg Leu  Pro His Leu
    1040                 1045                 1050

Thr Val  Tyr Phe Lys Leu Ala  Met Arg Asn Glu Glu  Leu Pro Ser
    1055                 1060                 1065

Val Lys  Glu Arg Ile Pro Tyr  Val Ile Val Ala Gln  Thr Glu Ala
    1070                 1075                 1080

Ala Glu  Arg Glu Ala Gly Val  Val Asn Ser Met Arg  Gly Thr Ala
    1085                 1090                 1095

Gln Asn  Pro Val Val Thr Lys  Thr Ala Arg Pro Gln  Pro Lys Arg
    1100                 1105                 1110

Lys Leu  Leu Val Ser Asp Leu  Ala Glu Asp Pro Thr  Tyr Val Ser
    1115                 1120                 1125

Glu Asn  Asp Val Pro Leu Asn  Thr Asp Tyr Tyr Phe  Ser His Leu
    1130                 1135                 1140

Leu Gly  Thr Ile Ser Val Thr  Phe Lys Ala Leu Phe  Gly Asn Asp
    1145                 1150                 1155

Val Arg  Thr Thr Glu Asn Leu  Leu Lys Arg Phe Ile  Pro Glu Thr
    1160                 1165                 1170

Pro His  Lys Thr Pro Thr Lys  Thr Gln Ala Leu Leu  Glu Arg Ala
    1175                 1180                 1185

Gly Phe  Glu Lys Leu Thr Pro  Phe Thr Pro Glu Glu  Glu Ser Arg
    1190                 1195                 1200

Arg Ile  Leu His Thr Val Phe  Cys Thr Leu Glu Ala  Ala Pro His
    1205                 1210                 1215

Gln Ser
    1220
```

<210> SEQ ID NO 7
<211> LENGTH: 1407
<212> TYPE: DNA
<213> ORGANISM: artificial sequence
<220> FEATURE:
<223> OTHER INFORMATION: EHV-1 glycoprotein (gC) gene (AY464052) from
EHV-1 V592 strain

<400> SEQUENCE: 7
atgtggttgc ctaatctcgt gagatttgtg gcggtcgcgt atctaatctg tgccggggcg 60
atattaactt atgcctctgg agctagtgct agctccagcc agagtacgcc cgctacacca 120
actcacacaa ctccgaatct aactaccgca cacggcgcgg gctctgacaa cacaactaac 180
gcaaacggta cagaatctac acactcccat gaaaccacaa tcacctgcac caagagtctc 240
atatctgtgc cctactacaa atctgtcgat atgaactgta caacgtcggt aggcgtaaat 300
tatagcgagt accgcctcga gatttacttg aaccagcgca ccccattttc gggtacgccc 360
cccggcgacg aagaaaacta catcaaccat aacgccacca aggatcagac tctgctgtta 420
ttctcaacgg cagagaggaa aaaatctcga aggggtggcc agctgggagt tatcccagac 480
aggctaccaa agcgccagct gtttaacctt cccctccaca cggaaggtgg tacaaagttt 540
ccactgacca tcaaatctgt agattggcgg acggccggca tttacgtgtg gtccttgtat 600
gccaaaaatg gcacgctcgt taacagtacc agcgttaccg tctcaaccta caacgcaccg 660
ttgctggacc tttccgttca cccgagcctg aagggggaaa actacagggc cacgtgcgtc 720
gtcgcaagct actttccaca cagctccgtc aagctgcggt ggtacaaaaa tgcccgcgag 780
gtggacttta caaagtacgt tacgaacgcc tcaagcgtgt gggtagacgg gctaatcacg 840
cgaatctcta cggtgtctat cccggttgat ccggaggagg aatacacacc cagtcttcgc 900
tgtagcatag actggtacag ggacgaagta tcatttgctc gcatagccaa agctggaaca 960
ccctctgtgt ttgttgcccc aaccgtgtcc gtttcggtag aagacggaga cgccgtctgt 1020
acggctaaat gcgtaccgag caccggggtg ttcgtatcgt ggtcagtgaa cgaccaccta 1080
ccaggggttc cgtcgcaaga catgacaacc ggagtctgcc ctagccactc gggattggtt 1140
aacatgcaaa gccgccggcc cctctcagaa gagaatgggg agagggagta tagctgcata 1200
atagaggggt accccgacgg cctgcctatg ttttcggaca cagtggtata tgacgcctcc 1260
ccgattgttg aggacaggcc ggttttgacg agcatcatcg cagttacttg cggggccgcg 1320
gcactggcgc tggtcgttct catcacagcc gtttgttttt actgctccaa gccctcacag 1380
gcgccgtaca agaagtctga cttttag 1407

<210> SEQ ID NO 8
<211> LENGTH: 468
<212> TYPE: PRT
<213> ORGANISM: artificial sequence
<220> FEATURE:
<223> OTHER INFORMATION: EHV-1 glycoprotein (gC) protein (AAS45900.1)
encoded by AY464052 from EHV-1 V592 strain

<400> SEQUENCE: 8

Met Trp Leu Pro Asn Leu Val Arg Phe Val Ala Val Ala Tyr Leu Ile
1 5 10 15

Cys Ala Gly Ala Ile Leu Thr Tyr Ala Ser Gly Ala Ser Ala Ser Ser
20 25 30

Ser Gln Ser Thr Pro Ala Thr Pro Thr His Thr Thr Pro Asn Leu Thr
35 40 45

```
Thr Ala His Gly Ala Gly Ser Asp Asn Thr Thr Asn Ala Asn Gly Thr
    50                  55                  60

Glu Ser Thr His Ser His Glu Thr Thr Ile Thr Cys Thr Lys Ser Leu
65                  70                  75                  80

Ile Ser Val Pro Tyr Tyr Lys Ser Val Asp Met Asn Cys Thr Thr Ser
                85                  90                  95

Val Gly Val Asn Tyr Ser Glu Tyr Arg Leu Glu Ile Tyr Leu Asn Gln
            100                 105                 110

Arg Thr Pro Phe Ser Gly Thr Pro Pro Gly Asp Glu Glu Asn Tyr Ile
        115                 120                 125

Asn His Asn Ala Thr Lys Asp Gln Thr Leu Leu Leu Phe Ser Thr Ala
    130                 135                 140

Glu Arg Lys Lys Ser Arg Arg Gly Gly Gln Leu Gly Val Ile Pro Asp
145                 150                 155                 160

Arg Leu Pro Lys Arg Gln Leu Phe Asn Leu Pro Leu His Thr Glu Gly
                165                 170                 175

Gly Thr Lys Phe Pro Leu Thr Ile Lys Ser Val Asp Trp Arg Thr Ala
            180                 185                 190

Gly Ile Tyr Val Trp Ser Leu Tyr Ala Lys Asn Gly Thr Leu Val Asn
        195                 200                 205

Ser Thr Ser Val Thr Val Ser Thr Tyr Asn Ala Pro Leu Leu Asp Leu
    210                 215                 220

Ser Val His Pro Ser Leu Lys Gly Glu Asn Tyr Arg Ala Thr Cys Val
225                 230                 235                 240

Val Ala Ser Tyr Phe Pro His Ser Ser Val Lys Leu Arg Trp Tyr Lys
                245                 250                 255

Asn Ala Arg Glu Val Asp Phe Thr Lys Tyr Val Thr Asn Ala Ser Ser
            260                 265                 270

Val Trp Val Asp Gly Leu Ile Thr Arg Ile Ser Thr Val Ser Ile Pro
        275                 280                 285

Val Asp Pro Glu Glu Glu Tyr Thr Pro Ser Leu Arg Cys Ser Ile Asp
    290                 295                 300

Trp Tyr Arg Asp Glu Val Ser Phe Ala Arg Ile Ala Lys Ala Gly Thr
305                 310                 315                 320

Pro Ser Val Phe Val Ala Pro Thr Val Ser Val Ser Val Glu Asp Gly
                325                 330                 335

Asp Ala Val Cys Thr Ala Lys Cys Val Pro Ser Thr Gly Val Phe Val
            340                 345                 350

Ser Trp Ser Val Asn Asp His Leu Pro Gly Val Pro Ser Gln Asp Met
        355                 360                 365

Thr Thr Gly Val Cys Pro Ser His Ser Gly Leu Val Asn Met Gln Ser
    370                 375                 380

Arg Arg Pro Leu Ser Glu Glu Asn Gly Glu Arg Glu Tyr Ser Cys Ile
385                 390                 395                 400

Ile Glu Gly Tyr Pro Asp Gly Leu Pro Met Phe Ser Asp Thr Val Val
                405                 410                 415

Tyr Asp Ala Ser Pro Ile Val Glu Asp Arg Pro Val Leu Thr Ser Ile
            420                 425                 430

Ile Ala Val Thr Cys Gly Ala Ala Ala Leu Ala Leu Val Val Leu Ile
        435                 440                 445

Thr Ala Val Cys Phe Tyr Cys Ser Lys Pro Ser Gln Ala Pro Tyr Lys
    450                 455                 460
```

Lys Ser Asp Phe
465

<210> SEQ ID NO 9
<211> LENGTH: 1407
<212> TYPE: DNA
<213> ORGANISM: artificial sequence
<220> FEATURE:
<223> OTHER INFORMATION: EHV-1 glycoprotein (gC) gene (AY665713) from
EHV-1 Ab4 strain

<400> SEQUENCE: 9
atgtggttgc ctaatctcgt gagatttgtg gcggtcgcgt atctaatctg tgccggggcg 60
atattaactt atgcctctgg agctagtgct agctccagcc agagtacgcc cgctacacca 120
actcacacaa ctccgaatct aactaccgca cacggcgcgg gctctgacaa cacaactaac 180
gcaaacggta cagaatctac acactcccat gaaaccacaa tcacctgcac caagagtctc 240
atatctgtgc cctactacaa atctgtcgat atgaactgta caacgtcggt aggcgtaaat 300
tatagcgagt accgcctcga gatttacttg aaccagcgca ccccattttc gggtacgccc 360
cccggcgacg aagaaaacta catcaaccat aacgccacca aggatcagac tctgctgtta 420
ttctcaacgg cagagaggaa aaaatctcga aggggtggcc agctgggagt tatcccagac 480
aggctaccaa agcgccagct gtttaacctt cccctccaca cggaaggtgg tacaaagttt 540
ccactgacca tcaaatctgt agattggcgg acggccggca tttacgtgtg gtccttgtat 600
gccaaaaatg gcacgctcgt taacagtacc agcgttaccg tctcaaccta caacgcaccg 660
ttgctggacc tttccgttca cccgagcctg aagggggaaa actacagggc cacgtgcgtc 720
gtcgcaagct actttccaca cagctccgtc aagctgcggt ggtacaaaaa tgcccgcgag 780
gtggacttta caaagtacgt tacgaacgcc tcaagcgtgt gggtagacgg gctaatcacg 840
cgaatctcta cggtgtctat cccggttgat ccggaggagg aatacacacc cagtcttcgc 900
tgtagcatag actggtacag ggacgaagta tcatttgctc gcatagccaa agctggaaca 960
ccctctgtgt ttgttgcccc aaccgtgtcc gtttcggtag aagacggaga cgccgtctgt 1020
acggctaaat gcgtaccgag caccggggtg ttcgtatcgt ggtcagtgaa cgaccaccta 1080
ccaggggttc cgtcgcaaga catgacaacc ggagtctgcc ctagccactc gggattggtt 1140
aacatgcaaa gccgccggcc ccctctcagaa gagaatgggg agagggagta tagctgcata 1200
atagaggggt accccgacgg cctgcctatg ttttcggaca cagtggtata tgacgcctcc 1260
ccgattgttg aggacaggcc ggttttgacg agcatcatcg cagttacttg cggggccgcg 1320
gcactggcgc tggtcgttct catcacagcc gtctgttttt actgctccaa gccctcacag 1380
gcgccgtaca agaagtctga cttttag 1407

<210> SEQ ID NO 10
<211> LENGTH: 468
<212> TYPE: PRT
<213> ORGANISM: artificial sequence
<220> FEATURE:
<223> OTHER INFORMATION: EHV-1 glycoprotein (gC) protein (AAT67273.1)
encoded by AY665713) from EHV-1 Ab4 strain

<400> SEQUENCE: 10

Met Trp Leu Pro Asn Leu Val Arg Phe Val Ala Val Ala Tyr Leu Ile
1               5                   10                  15

Cys Ala Gly Ala Ile Leu Thr Tyr Ala Ser Gly Ala Ser Ala Ser Ser
            20                  25                  30

-continued

```
Ser Gln Ser Thr Pro Ala Thr Pro Thr His Thr Thr Pro Asn Leu Thr
        35                  40                  45

Thr Ala His Gly Ala Gly Ser Asp Asn Thr Thr Asn Ala Asn Gly Thr
    50                  55                  60

Glu Ser Thr His Ser His Glu Thr Thr Ile Thr Cys Thr Lys Ser Leu
65                  70                  75                  80

Ile Ser Val Pro Tyr Tyr Lys Ser Val Asp Met Asn Cys Thr Thr Ser
                85                  90                  95

Val Gly Val Asn Tyr Ser Glu Tyr Arg Leu Glu Ile Tyr Leu Asn Gln
            100                 105                 110

Arg Thr Pro Phe Ser Gly Thr Pro Pro Gly Asp Glu Glu Asn Tyr Ile
        115                 120                 125

Asn His Asn Ala Thr Lys Asp Gln Thr Leu Leu Leu Phe Ser Thr Ala
    130                 135                 140

Glu Arg Lys Lys Ser Arg Arg Gly Gly Gln Leu Gly Val Ile Pro Asp
145                 150                 155                 160

Arg Leu Pro Lys Arg Gln Leu Phe Asn Leu Pro Leu His Thr Glu Gly
                165                 170                 175

Gly Thr Lys Phe Pro Leu Thr Ile Lys Ser Val Asp Trp Arg Thr Ala
            180                 185                 190

Gly Ile Tyr Val Trp Ser Leu Tyr Ala Lys Asn Gly Thr Leu Val Asn
        195                 200                 205

Ser Thr Ser Val Thr Val Ser Thr Tyr Asn Ala Pro Leu Leu Asp Leu
    210                 215                 220

Ser Val His Pro Ser Leu Lys Gly Glu Asn Tyr Arg Ala Thr Cys Val
225                 230                 235                 240

Val Ala Ser Tyr Phe Pro His Ser Ser Val Lys Leu Arg Trp Tyr Lys
                245                 250                 255

Asn Ala Arg Glu Val Asp Phe Thr Lys Tyr Val Thr Asn Ala Ser Ser
            260                 265                 270

Val Trp Val Asp Gly Leu Ile Thr Arg Ile Ser Thr Val Ser Ile Pro
        275                 280                 285

Val Asp Pro Glu Glu Glu Tyr Thr Pro Ser Leu Arg Cys Ser Ile Asp
    290                 295                 300

Trp Tyr Arg Asp Glu Val Ser Phe Ala Arg Ile Ala Lys Ala Gly Thr
305                 310                 315                 320

Pro Ser Val Phe Val Ala Pro Thr Val Ser Val Ser Val Glu Asp Gly
                325                 330                 335

Asp Ala Val Cys Thr Ala Lys Cys Val Pro Ser Thr Gly Val Phe Val
            340                 345                 350

Ser Trp Ser Val Asn Asp His Leu Pro Gly Val Pro Ser Gln Asp Met
        355                 360                 365

Thr Thr Gly Val Cys Pro Ser His Ser Gly Leu Val Asn Met Gln Ser
    370                 375                 380

Arg Arg Pro Leu Ser Glu Glu Asn Gly Glu Arg Glu Tyr Ser Cys Ile
385                 390                 395                 400

Ile Glu Gly Tyr Pro Asp Gly Leu Pro Met Phe Ser Asp Thr Val Val
                405                 410                 415

Tyr Asp Ala Ser Pro Ile Val Glu Asp Arg Pro Val Leu Thr Ser Ile
            420                 425                 430

Ile Ala Val Thr Cys Gly Ala Ala Ala Leu Ala Leu Val Val Leu Ile
        435                 440                 445

Thr Ala Val Cys Phe Tyr Cys Ser Lys Pro Ser Gln Ala Pro Tyr Lys
```

450 455 460

Lys Ser Asp Phe
465

<210> SEQ ID NO 11
<211> LENGTH: 1407
<212> TYPE: DNA
<213> ORGANISM: artificial sequence
<220> FEATURE:
<223> OTHER INFORMATION: EHV-1 glycoprotein (gC) gene (NC_001491) from EHV-1

<400> SEQUENCE: 11
atgtggttgc ctaatctcgt gagatttgtg gcggtcgcgt atctaatctg tgccggggcg 60
atattaactt atgcctctgg agctagtgct agctccagcc agagtacgcc cgctacacca 120
actcacacaa ctccgaatct aactaccgca cacggcgcgg gctctgacaa cacaactaac 180
gcaaacggta cagaatctac acactcccat gaaaccacaa tcacctgcac caagagtctc 240
atatctgtgc cctactacaa atctgtcgat atgaactgta caacgtcggt aggcgtaaat 300
tatagcgagt accgcctcga gatttacttg aaccagcgca ccccattttc gggtacgccc 360
cccggcgacg aagaaaacta catcaaccat aacgccacca aggatcagac tctgctgtta 420
ttctcaacgg cagagaggaa aaaatctcga aggggtggcc agctgggagt tatcccagac 480
aggctaccaa agcgccagct gtttaacctt cccctccaca cggaaggtgg tacaaagttt 540
ccactgacca tcaaatctgt agattggcgg acggccggca tttacgtgtg gtccttgtat 600
gccaaaaatg gcacgctcgt taacagtacc agcgttaccg tctcaaccta caacgcaccg 660
ttgctggacc tttccgttca cccgagcctg aagggggaaa actacagggc cacgtgcgtc 720
gtcgcaagct actttccaca cagctccgtc aagctgcggt ggtacaaaaa tgcccgcgag 780
gtggacttta caaagtacgt tacgaacgcc tcaagcgtgt gggtagacgg gctaatcacg 840
cgaatctcta cggtgtctat cccggttgat ccggaggagg aatacacacc cagtcttcgc 900
tgtagcatag actggtacag ggacgaagta tcatttgctc gcatagccaa agctggaaca 960
ccctctgtgt ttgttgcccc aaccgtgtcc gtttcggtag aagacggaga cgccgtctgt 1020
acggctaaat gcgtaccgag caccggggtg ttcgtatcgt ggtcagtgaa cgaccaccta 1080
ccaggggttc cgtcgcaaga catgacaacc ggagtctgcc ctagccactc gggattggtt 1140
aacatgcaaa gccgccggcc cctctcagaa gagaatgggg agagggagta tagctgcata 1200
atagaggggt accccgacgg cctgcctatg ttttcggaca cagtggtata tgacgcctcc 1260
ccgattgttg aggacaggcc ggttttgacg agcatcatcg cagttacttg cggggccgcg 1320
gcactggcgc tggtcgttct catcacagcc gtctgttttt actgctccaa gccctcacag 1380
gcgccgtaca agaagtctga cttttag 1407

<210> SEQ ID NO 12
<211> LENGTH: 468
<212> TYPE: PRT
<213> ORGANISM: artificial sequence
<220> FEATURE:
<223> OTHER INFORMATION: EHV-1 glycoprotein (gC) protein (YP_053061.1) encoded by NC_001491

<400> SEQUENCE: 12

Met Trp Leu Pro Asn Leu Val Arg Phe Val Ala Val Ala Tyr Leu Ile
1 5 10 15

Cys Ala Gly Ala Ile Leu Thr Tyr Ala Ser Gly Ala Ser Ala Ser Ser

-continued

```
            20                  25                  30

Ser Gln Ser Thr Pro Ala Thr Pro Thr His Thr Thr Pro Asn Leu Thr
        35                  40                  45

Thr Ala His Gly Ala Gly Ser Asp Asn Thr Thr Asn Ala Asn Gly Thr
    50                  55                  60

Glu Ser Thr His Ser His Glu Thr Thr Ile Thr Cys Thr Lys Ser Leu
65                  70                  75                  80

Ile Ser Val Pro Tyr Tyr Lys Ser Val Asp Met Asn Cys Thr Thr Ser
                85                  90                  95

Val Gly Val Asn Tyr Ser Glu Tyr Arg Leu Glu Ile Tyr Leu Asn Gln
            100                 105                 110

Arg Thr Pro Phe Ser Gly Thr Pro Pro Gly Asp Glu Glu Asn Tyr Ile
        115                 120                 125

Asn His Asn Ala Thr Lys Asp Gln Thr Leu Leu Leu Phe Ser Thr Ala
    130                 135                 140

Glu Arg Lys Lys Ser Arg Arg Gly Gly Gln Leu Gly Val Ile Pro Asp
145                 150                 155                 160

Arg Leu Pro Lys Arg Gln Leu Phe Asn Leu Pro Leu His Thr Glu Gly
                165                 170                 175

Gly Thr Lys Phe Pro Leu Thr Ile Lys Ser Val Asp Trp Arg Thr Ala
            180                 185                 190

Gly Ile Tyr Val Trp Ser Leu Tyr Ala Lys Asn Gly Thr Leu Val Asn
        195                 200                 205

Ser Thr Ser Val Thr Val Ser Thr Tyr Asn Ala Pro Leu Leu Asp Leu
    210                 215                 220

Ser Val His Pro Ser Leu Lys Gly Glu Asn Tyr Arg Ala Thr Cys Val
225                 230                 235                 240

Val Ala Ser Tyr Phe Pro His Ser Ser Val Lys Leu Arg Trp Tyr Lys
                245                 250                 255

Asn Ala Arg Glu Val Asp Phe Thr Lys Tyr Val Thr Asn Ala Ser Ser
            260                 265                 270

Val Trp Val Asp Gly Leu Ile Thr Arg Ile Ser Thr Val Ser Ile Pro
        275                 280                 285

Val Asp Pro Glu Glu Glu Tyr Thr Pro Ser Leu Arg Cys Ser Ile Asp
    290                 295                 300

Trp Tyr Arg Asp Glu Val Ser Phe Ala Arg Ile Ala Lys Ala Gly Thr
305                 310                 315                 320

Pro Ser Val Phe Val Ala Pro Thr Val Ser Val Ser Val Glu Asp Gly
                325                 330                 335

Asp Ala Val Cys Thr Ala Lys Cys Val Pro Ser Thr Gly Val Phe Val
            340                 345                 350

Ser Trp Ser Val Asn Asp His Leu Pro Gly Val Pro Ser Gln Asp Met
        355                 360                 365

Thr Thr Gly Val Cys Pro Ser His Ser Gly Leu Val Asn Met Gln Ser
    370                 375                 380

Arg Arg Pro Leu Ser Glu Glu Asn Gly Glu Arg Glu Tyr Ser Cys Ile
385                 390                 395                 400

Ile Glu Gly Tyr Pro Asp Gly Leu Pro Met Phe Ser Asp Thr Val Val
                405                 410                 415

Tyr Asp Ala Ser Pro Ile Val Glu Asp Arg Pro Val Leu Thr Ser Ile
            420                 425                 430

Ile Ala Val Thr Cys Gly Ala Ala Ala Leu Ala Leu Val Val Leu Ile
        435                 440                 445
```

Thr Ala Val Cys Phe Tyr Cys Ser Lys Pro Ser Gln Ala Pro Tyr Lys
450 455 460

Lys Ser Asp Phe
465

<210> SEQ ID NO 13
<211> LENGTH: 195
<212> TYPE: PRT
<213> ORGANISM: artificial sequence
<220> FEATURE:
<223> OTHER INFORMATION: EHV-1 RacL DNA polymerase partial sequence

<400> SEQUENCE: 13

Phe Asp Ser Gln Ala Asp Ala Ala Ser Glu Thr Ser Glu Leu Ala Met
1 5 10 15

Asp Ser Gln Ser His Ala Phe Asp Ser Thr Asp Glu Pro Asp Gly Val
20 25 30

Asp Gly Thr Pro Asp Ala Ala Gly Ser Gly Ala Thr Ser Glu Asn Gly
35 40 45

Gly Gly Lys Pro Gly Val Gly Arg Ala Val Gly Tyr Gln Gly Ala Lys
50 55 60

Val Leu Asp Pro Val Ser Gly Phe His Val Asp Pro Val Val Val Phe
65 70 75 80

Asp Phe Ala Ser Leu Tyr Pro Ser Ile Ile Gln Ala His Asn Leu Cys
85 90 95

Phe Thr Thr Leu Ala Leu Asp Glu Val Asp Leu Ala Gly Leu Gln Pro
100 105 110

Ser Val Asp Tyr Ser Thr Phe Glu Val Gly Asp Gln Lys Leu Phe Phe
115 120 125

Val His Ala His Ile Arg Glu Ser Leu Leu Gly Ile Leu Leu Arg Asp
130 135 140

Trp Leu Ala Met Arg Lys Ala Val Arg Ala Arg Ile Pro Thr Ser Thr
145 150 155 160

Pro Glu Glu Ala Val Leu Leu Asp Lys Gln Gln Ser Ala Ile Lys Val
165 170 175

Ile Cys Asn Ser Val Tyr Gly Phe Thr Gly Val Ala Asn Gly Leu Leu
180 185 190

Pro Cys Leu
195

<210> SEQ ID NO 14
<211> LENGTH: 195
<212> TYPE: PRT
<213> ORGANISM: artificial sequence
<220> FEATURE:
<223> OTHER INFORMATION: EHV-1 RacL DNA polymerase partial sequence
comprising N at 752 of full length EHV-1 DNA polymerase

<400> SEQUENCE: 14

Phe Asp Ser Gln Ala Asp Ala Ala Ser Glu Thr Ser Glu Leu Ala Met
1 5 10 15

Asp Ser Gln Ser His Ala Phe Asp Ser Thr Asp Glu Pro Asp Gly Val
20 25 30

Asp Gly Thr Pro Asp Ala Ala Gly Ser Gly Ala Thr Ser Glu Asn Gly
35 40 45

Gly Gly Lys Pro Gly Val Gly Arg Ala Val Gly Tyr Gln Gly Ala Lys
50 55 60

```
Val Leu Asp Pro Val Ser Gly Phe His Val Asp Pro Val Val Val Phe
65                  70                  75                  80

Asp Phe Ala Ser Leu Tyr Pro Ser Ile Ile Gln Ala His Asn Leu Cys
                85                  90                  95

Phe Thr Thr Leu Ala Leu Asp Glu Val Asp Leu Ala Gly Leu Gln Pro
            100                 105                 110

Ser Val Asn Tyr Ser Thr Phe Glu Val Gly Asp Gln Lys Leu Phe Phe
        115                 120                 125

Val His Ala His Ile Arg Glu Ser Leu Leu Gly Ile Leu Leu Arg Asp
    130                 135                 140

Trp Leu Ala Met Arg Lys Ala Val Arg Ala Arg Ile Pro Thr Ser Thr
145                 150                 155                 160

Pro Glu Glu Ala Val Leu Leu Asp Lys Gln Gln Ser Ala Ile Lys Val
                165                 170                 175

Ile Cys Asn Ser Val Tyr Gly Phe Thr Gly Val Ala Asn Gly Leu Leu
            180                 185                 190

Pro Cys Leu
        195


<210> SEQ ID NO 15
<211> LENGTH: 194
<212> TYPE: PRT
<213> ORGANISM: artificial sequence
<220> FEATURE:
<223> OTHER INFORMATION: EHV-1 RacL DNA polymerase partial sequence with
      amino acid deletion at 752 of full length EHV-1 DNA polymerase

<400> SEQUENCE: 15

Phe Asp Ser Gln Ala Asp Ala Ala Ser Glu Thr Ser Glu Leu Ala Met
1               5                   10                  15

Asp Ser Gln Ser His Ala Phe Asp Ser Thr Asp Glu Pro Asp Gly Val
            20                  25                  30

Asp Gly Thr Pro Asp Ala Ala Gly Ser Gly Ala Thr Ser Glu Asn Gly
        35                  40                  45

Gly Gly Lys Pro Gly Val Gly Arg Ala Val Gly Tyr Gln Gly Ala Lys
    50                  55                  60

Val Leu Asp Pro Val Ser Gly Phe His Val Asp Pro Val Val Val Phe
65                  70                  75                  80

Asp Phe Ala Ser Leu Tyr Pro Ser Ile Ile Gln Ala His Asn Leu Cys
                85                  90                  95

Phe Thr Thr Leu Ala Leu Asp Glu Val Asp Leu Ala Gly Leu Gln Pro
            100                 105                 110

Ser Val Tyr Ser Thr Phe Glu Val Gly Asp Gln Lys Leu Phe Phe Val
        115                 120                 125

His Ala His Ile Arg Glu Ser Leu Leu Gly Ile Leu Leu Arg Asp Trp
    130                 135                 140

Leu Ala Met Arg Lys Ala Val Arg Ala Arg Ile Pro Thr Ser Thr Pro
145                 150                 155                 160

Glu Glu Ala Val Leu Leu Asp Lys Gln Gln Ser Ala Ile Lys Val Ile
                165                 170                 175

Cys Asn Ser Val Tyr Gly Phe Thr Gly Val Ala Asn Gly Leu Leu Pro
            180                 185                 190

Cys Leu


<210> SEQ ID NO 16
<211> LENGTH: 34
```

-continued

<212> TYPE: DNA
<213> ORGANISM: artificial sequence
<220> FEATURE:
<223> OTHER INFORMATION: PN1 primer

<400> SEQUENCE: 16
cccaagcttg agatggcggc gcgcgaacag gcca 34

<210> SEQ ID NO 17
<211> LENGTH: 61
<212> TYPE: DNA
<213> ORGANISM: artificial sequence
<220> FEATURE:
<223> OTHER INFORMATION: PN2 primer

<400> SEQUENCE: 17
cgcggatcct taagcgtagt ctgggacgtc gtatgggtag ctttgatggg gagctgcttc 60
t 61

<210> SEQ ID NO 18
<211> LENGTH: 22
<212> TYPE: DNA
<213> ORGANISM: artificial sequence
<220> FEATURE:
<223> OTHER INFORMATION: P1 primer

<400> SEQUENCE: 18
gcctgcgtgg aggagtattg gg 22

<210> SEQ ID NO 19
<211> LENGTH: 45
<212> TYPE: DNA
<213> ORGANISM: artificial sequence
<220> FEATURE:
<223> OTHER INFORMATION: P2 primer

<400> SEQUENCE: 19
taattgatta ctattaataa ctattacacc ggaggaagaa agtcg 45

<210> SEQ ID NO 20
<211> LENGTH: 46
<212> TYPE: DNA
<213> ORGANISM: artificial sequence
<220> FEATURE:
<223> OTHER INFORMATION: P3 primer

<400> SEQUENCE: 20
caaactcatc aatgtatctt aaggtctgtg taaatttaaa gtgcga 46

<210> SEQ ID NO 21
<211> LENGTH: 22
<212> TYPE: DNA
<213> ORGANISM: artificial sequence
<220> FEATURE:
<223> OTHER INFORMATION: P4 primer

<400> SEQUENCE: 21
caaaggtgcc agcgtcacat cg 22

<210> SEQ ID NO 22
<211> LENGTH: 45
<212> TYPE: DNA
<213> ORGANISM: artificial sequence
<220> FEATURE:
<223> OTHER INFORMATION: P5 primer

<400> SEQUENCE: 22
acgactttct tcctccggtg taatagttat taatagtaat caatt 45

<210> SEQ ID NO 23
<211> LENGTH: 42
<212> TYPE: DNA
<213> ORGANISM: artificial sequence
<220> FEATURE:
<223> OTHER INFORMATION: P6 primer

<400> SEQUENCE: 23
cccttgctca ccatggtggc ggatctgacg gttcactaaa cc 42

<210> SEQ ID NO 24
<211> LENGTH: 42
<212> TYPE: DNA
<213> ORGANISM: artificial sequence
<220> FEATURE:
<223> OTHER INFORMATION: P7 primer

<400> SEQUENCE: 24
ggtttagtga accgtcagat ccgccaccat ggtgagcaag gg 42

<210> SEQ ID NO 25
<211> LENGTH: 45
<212> TYPE: DNA
<213> ORGANISM: artificial sequence
<220> FEATURE:
<223> OTHER INFORMATION: P8 primer

<400> SEQUENCE: 25
cgcactttaa atttacacag accttaagat acattgatga gtttg 45

<210> SEQ ID NO 26
<211> LENGTH: 64
<212> TYPE: DNA
<213> ORGANISM: artificial sequence
<220> FEATURE:
<223> OTHER INFORMATION: P9 primer

<400> SEQUENCE: 26
tccccgcgga taacttcgta tagcatacat tatacgaagt tattagttat taatagtaat 60
caat 64

<210> SEQ ID NO 27
<211> LENGTH: 64
<212> TYPE: DNA
<213> ORGANISM: artificial sequence
<220> FEATURE:
<223> OTHER INFORMATION: P10 primer

<400> SEQUENCE: 27
ctagctagca taacttcgta taatgtatgc tatacgaagt tatcttaaga tacattgatg 60
agtt 64

<210> SEQ ID NO 28
<211> LENGTH: 25
<212> TYPE: DNA
<213> ORGANISM: artificial sequence
<220> FEATURE:
<223> OTHER INFORMATION: gC-1 primer

<400> SEQUENCE: 28
gactctgtcg acggccaccg ccgac 25

<210> SEQ ID NO 29
<211> LENGTH: 25
<212> TYPE: DNA
<213> ORGANISM: artificial sequence
<220> FEATURE:
<223> OTHER INFORMATION: gC-2 primer

<400> SEQUENCE: 29
cctggatcca gactctattc ccatg 25

<210> SEQ ID NO 30
<211> LENGTH: 20
<212> TYPE: DNA
<213> ORGANISM: artificial sequence
<220> FEATURE:
<223> OTHER INFORMATION: delta gC-1 primer

<400> SEQUENCE: 30
ttggcctatg cggacgactt 20

<210> SEQ ID NO 31
<211> LENGTH: 20
<212> TYPE: DNA
<213> ORGANISM: artificial sequence
<220> FEATURE:
<223> OTHER INFORMATION: delta gC-2 primer

<400> SEQUENCE: 31
ccctttggtg catggtatgt 20

<210> SEQ ID NO 32
<211> LENGTH: 21
<212> TYPE: DNA
<213> ORGANISM: artificial sequence
<220> FEATURE:
<223> OTHER INFORMATION: Poly1 primer

<400> SEQUENCE: 32
tctggaacta tcggcggtgg c 21

<210> SEQ ID NO 33
<211> LENGTH: 21
<212> TYPE: DNA
<213> ORGANISM: artificial sequence
<220> FEATURE:
<223> OTHER INFORMATION: Poly2 primer

<400> SEQUENCE: 33
cgggtcttga ggagcatgtc g 21

<210> SEQ ID NO 34
<211> LENGTH: 1407
<212> TYPE: DNA
<213> ORGANISM: artificial sequence
<220> FEATURE:
<223> OTHER INFORMATION: EHV-1 glycoprotein (gC) gene from EHV-1 RacL11
      strain

<400> SEQUENCE: 34
atgtggttgc ctaatctcgt gagatttgtg gcggtcgcgt atctaatctg tgccggggcg 60
atattaactt atgcctctgg agctagtgct agctccagcc agagtacgcc cgctacacca 120
actcacacaa ctccgaatct aactaccgca cacggcgcgg gctctgacaa cacaactaac 180
gcaaacggta cagaatctac acactcccat gaaaccacaa tcacctgcac caagagtctc 240

-continued

```
atatctgtgc cctactacaa atctgtcgat atgaactgta caacgtcggt aggcgtaaat    300

tatagcgagt accgcctcga gatttacttg aaccagcgca ccccattttc gggtacgccc    360

cccggcgacg aagaaaacta catcaaccat aacgccacca aggatcagac tctgctgtta    420

ttctcaacgg caaagaggaa aaaatctcga aggggtggcc agctgggagt tatcccagac    480

aggctaccaa agcgcaagct gtttaacctt cccctccaca cggaaggtgg tacaaagttt    540

ccactgacca tcaaatctgt agattggcgg acggccggca tttacgtgtg gtccttgtat    600

gccaaaaatg gcacgctcgt taacagtacc agcgttaccg tctcaaccta caacgcaccg    660

ttgctggacc tttccgttca cccgagcctg aagggggaaa actacagggc cacgtgcgtc    720

gtcgcaagct actttccaca cagctccgtc aagctgcggt ggtacaaaaa tgcccgcgag    780

gtggacttta caaagtacgt tacgaacgcc tcaagcgtgt gggcagacgg gctaatcacg    840

cgaatctcta cggtgtctat cccggttggt ccggaggagg aatacacacc cagtcttcgc    900

tgtagcatag actggtacag ggacgaagta tcatttgctc gcatagccaa agctggaaca    960

ccctctgtgt ttgttgcccc aaccgtgtcc gtttcggtag aagacggaga cgccgtctgt   1020

acggctaaat gcgtaccgag caccggggtg ttcgtatcgt ggtcagtgaa cgaccaccta   1080

ccaggggttc cgtcgcaaga catgacaacc ggagtctgcc ctagccactc gggattggtt   1140

aacatgcaaa gccgccggcc cctctcagaa gagaatgggg agagggagta tagctgcata   1200

atagaggggt accccgacgg cctgcctatg ttttcggaca cagtggtata tgacgcctcc   1260

ccgattgttg aggacaggcc ggttttgacg agcatcatcg cagttacttg cggggccgcg   1320

gcactggcgc tggtcgttct catcacagcc gtctgttttt actgctccaa gccctcacag   1380

gcgccgtaca agaagtctga cttttag                                        1407
```

```
<210> SEQ ID NO 35
<211> LENGTH: 468
<212> TYPE: PRT
<213> ORGANISM: artificial sequence
<220> FEATURE:
<223> OTHER INFORMATION: EHV-1 glycoprotein (gC) protein from EHV-1
      RacL11 strain

<400> SEQUENCE: 35

Met Trp Leu Pro Asn Leu Val Arg Phe Val Ala Val Ala Tyr Leu Ile
1               5                   10                  15

Cys Ala Gly Ala Ile Leu Thr Tyr Ala Ser Gly Ala Ser Ala Ser Ser
            20                  25                  30

Ser Gln Ser Thr Pro Ala Thr Pro Thr His Thr Thr Pro Asn Leu Thr
        35                  40                  45

Thr Ala His Gly Ala Gly Ser Asp Asn Thr Thr Asn Ala Asn Gly Thr
    50                  55                  60

Glu Ser Thr His Ser His Glu Thr Thr Ile Thr Cys Thr Lys Ser Leu
65                  70                  75                  80

Ile Ser Val Pro Tyr Tyr Lys Ser Val Asp Met Asn Cys Thr Thr Ser
                85                  90                  95

Val Gly Val Asn Tyr Ser Glu Tyr Arg Leu Glu Ile Tyr Leu Asn Gln
            100                 105                 110

Arg Thr Pro Phe Ser Gly Thr Pro Pro Gly Asp Glu Glu Asn Tyr Ile
        115                 120                 125

Asn His Asn Ala Thr Lys Asp Gln Thr Leu Leu Leu Phe Ser Thr Ala
    130                 135                 140
```

Lys Arg Lys Lys Ser Arg Arg Gly Gly Gln Leu Gly Val Ile Pro Asp
145 150 155 160

Arg Leu Pro Lys Arg Lys Leu Phe Asn Leu Pro Leu His Thr Glu Gly
165 170 175

Gly Thr Lys Phe Pro Leu Thr Ile Lys Ser Val Asp Trp Arg Thr Ala
180 185 190

Gly Ile Tyr Val Trp Ser Leu Tyr Ala Lys Asn Gly Thr Leu Val Asn
195 200 205

Ser Thr Ser Val Thr Val Ser Thr Tyr Asn Ala Pro Leu Leu Asp Leu
210 215 220

Ser Val His Pro Ser Leu Lys Gly Glu Asn Tyr Arg Ala Thr Cys Val
225 230 235 240

Val Ala Ser Tyr Phe Pro His Ser Ser Val Lys Leu Arg Trp Tyr Lys
245 250 255

Asn Ala Arg Glu Val Asp Phe Thr Lys Tyr Val Thr Asn Ala Ser Ser
260 265 270

Val Trp Ala Asp Gly Leu Ile Thr Arg Ile Ser Thr Val Ser Ile Pro
275 280 285

Val Gly Pro Glu Glu Glu Tyr Thr Pro Ser Leu Arg Cys Ser Ile Asp
290 295 300

Trp Tyr Arg Asp Glu Val Ser Phe Ala Arg Ile Ala Lys Ala Gly Thr
305 310 315 320

Pro Ser Val Phe Val Ala Pro Thr Val Ser Val Ser Val Glu Asp Gly
325 330 335

Asp Ala Val Cys Thr Ala Lys Cys Val Pro Ser Thr Gly Val Phe Val
340 345 350

Ser Trp Ser Val Asn Asp His Leu Pro Gly Val Pro Ser Gln Asp Met
355 360 365

Thr Thr Gly Val Cys Pro Ser His Ser Gly Leu Val Asn Met Gln Ser
370 375 380

Arg Arg Pro Leu Ser Glu Glu Asn Gly Glu Arg Glu Tyr Ser Cys Ile
385 390 395 400

Ile Glu Gly Tyr Pro Asp Gly Leu Pro Met Phe Ser Asp Thr Val Val
405 410 415

Tyr Asp Ala Ser Pro Ile Val Glu Asp Arg Pro Val Leu Thr Ser Ile
420 425 430

Ile Ala Val Thr Cys Gly Ala Ala Ala Leu Ala Leu Val Val Leu Ile
435 440 445

Thr Ala Val Cys Phe Tyr Cys Ser Lys Pro Ser Gln Ala Pro Tyr Lys
450 455 460

Lys Ser Asp Phe
465

<210> SEQ ID NO 36
<211> LENGTH: 3663
<212> TYPE: DNA
<213> ORGANISM: artificial sequence
<220> FEATURE:
<223> OTHER INFORMATION: EHV-1 DNA polymerase (Pol) from EHV-1 NY03 strain

<400> SEQUENCE: 36
atggcggcgc gcgaacaggc caactccgtt cgcaggagcg ggttttttaa tccgtttatt 60
ggcaagaggc catttttcag gccgggaagc gggcagaccg cggagacaga gcgcccaagg 120 ccccccccaac actcgtactg cacagaggtg ggtagcttta agtttatagc tccaagatgc 180

```
ctcgatgaag aagcccccgc cgaccagcga cgcggtgtac acgtgggcac cttggagcgc    240
ccacccaaag tgtactgcga tggctcagag tacgacgtgc tgaactttgc ctccggaggt    300
tgctggcctc gcaggattcg ggtttggaac ggccaggatt ttcggggcga tggattcaac    360
cccagatttg agagatttca cgtgtacgac atagtagaga cttcggagag cgcctcacac    420
gatgacccat ccaggtttgc tgagctatcc cgcccaagcg ggtctgtggt aacactgctg    480
ggaatgagcg agtgtggaaa gcgagtcgcg gttcacgtct atggtgtgcg ccattatttt    540
tacatggcaa aggcggaggt ggatagcgct tgtggaataa ccaccgaggc agaactcgtg    600
cgcgcaatgg tggactgcgc gcacagctcg gctttgagcg cggccctggg aaatggcaac    660
ggcggcaaac agagcggcgg cagcggcggg ggatggtggg gcggaaagca cgtgtctgcg    720
gactgcttca aagtggagac cgtgtgccac acgacgctgt actactttgg atctaagcca    780
gctctctact atagagtatc tgcctccagc agccgcctgg gagggttcat ctgcgacaac    840
tttcacccgg agattacaaa attcgagggg agcgtggacg tgaccacgcg gctgttgttg    900
gacaatgaaa attttaccag tttcgggtgg taccgcctgc gacccggcac ccacggagag    960
cgtgttcaac ttcgccccgt tgagcgacac gtcacctcaa gcgacgtgga gattaactgt   1020
actcccgata acctggagcc gataccagac gaggctgcct ggcccgacta taagctcatg   1080
tgctttgata tagagtgtaa agctggaacg ggtaacgaaa tggcgttccc agtggcaact   1140
aaccaagagg acctggtcat ccagatctcc tgtctgctgt actcgcttgc tactcagaac   1200
cacgaacaca ccctgctgtt ttccctcggg tcatgcgata tctctgagga atactcgttt   1260
gcatgcgtcc agcgcggcga gcccagaccg acggttttgg agtttgacag cgagtacgag   1320
ctgctggttg ccttcctgac ctttctcaag cagtactctc ccgagttcgc caccggctac   1380
aacatcgtta attttgactg ggcgtacata gttaacaagg taacgtcggt gtataacatc   1440
aagctggacg ggtacggcaa gttcaacaaa ggggggctgt ttaaggtgtg ggacatcgcc   1500
acgaaccatt ttcagaagaa gagcaaggtg aaaatcaatg gcctgatatc tctagacatg   1560
tattctgtgg cgacggaaaa gctaaagcta cccagctaca aactcgacgc ggtcgtggga   1620
gacgtcctcg gcgagcataa gatagacctt ccctataaag aaataccctc ctattacgcg   1680
ggagggcctg accggagggg cgtaatagga gagtattgta tccaggactc taggctggtg   1740
ggcaagctgt tttttaagta cctcccccat ctggaactat cggcggtggc caaactcgcc   1800
cgtatcaccc taacgcgggt aatttttgac ggtcagcaaa ttcgcgtgta cacgtgcttg   1860
ctgaaactcg cccgcgagag aaatttcatt ttgccagaca acagacgccg gtttgacagt   1920
caggcagacg ccgcgtcaga gacttcggag ttggctatgg atagccaaag ccacgccttc   1980
gacagtacag acgaacccga cggtgtggac ggtaccccgg acgccgcagg atctggcgct   2040
acttctgaaa acggaggcgg gaagcccggc gtcgggaggg ccgtgggcta ccagggagca   2100
aaggttctag accccgtatc cggctttcat gtggaccccg tggttgtgtt tgacttcgct   2160
agcttatacc caagcattat ccaggcccat aacctctgtt tcaccaccct ggcgctcgat   2220
gaagtggatc tggccgggct tcaaccatcc gtcaactact cgacgttcga ggtgggtgac   2280
caaaagttat tttttgtcca cgcccatatt cgcgaaagcc tgcttggcat cttgctgcgc   2340
gactggctgg ccatgcgaaa ggcggtgagg gcgcgaatcc ccaccagcac ccccgaggag   2400
gcagttttac tagataagca gcagtctgcg attaaggtga tatgcaactc ggtttacgga   2460
ttcacggggg tggcaaacgg cctgttgccg tgtctgagga tagcggctac cgttaccacg   2520
```

```
ataggacgcg acatgctcct caagacccga gattacgttc actctcgttg ggcgacgcgc   2580
gagctgctgg aggacaattt tccaggggct ataggtttcc gaaaccacaa gccttactcc   2640
gtcagggtta tctacggaga caccgactcc gtgtttatca agtttgtggg cctgacgtac   2700
gagggggtat cggagctggg ggatgctatg tcgcgtcaga tttcagcgga cctctttaga   2760
gcgcccatca aactggagtg tgagaagacc tttcagcgac tgctgctgat caccaagaag   2820
aagtacatag gtgtcataaa cggggggaag atgctcatga agggggtcga cctggtccgc   2880
aaaaataact gctctttcat aaacttgtac gcgcgacatc tggtagatct tttgttgtac   2940
gacgaggatg tggccacggc ggcagcagag gtgacagacg tgcctcccgc agaatgggtg   3000
gggcgcccgc taccgagcgg ctttgacaag tttgggcgag tgctggtaga ggcgtacaac   3060
cgtatcactg cccccaactt ggacgtgcgc gagttcgtta tgactgctga gctgagccgc   3120
tcacccgaat tgtataccaa caagcgcctg ccgcacctca ccgtctactt taagctcgcc   3180
atgaggaatg aagaactgcc cagcgtaaaa gagagaattc cgtatgtgat agttgcgcag   3240
accgaggccg cggaacgcga agcgggtgta gtaaactcaa tgcgcggtac cgcccaaaac   3300
cccgtggtaa ccaagaccgc acgcccccaa cctaaacgca aactgctggt ttccgacctc   3360
gccgaagacc cgacctatgt ttccgagaat gacgtaccgc taaacacaga ctactatttc   3420
tcccacctgt tgggtaccat aagcgtgacc tttaaggctc tattcggaaa tgatgtgaga   3480
acaacagaaa atcttttaaa gcggtttatt ccggaaaccc cccacaagac ccccacgaaa   3540
acccaggcac tgcttgagcg cgccggcttt gaaaagctga cgccctttac accggaggaa   3600
gaaagtcgtc gaatactgca tacagttttt tgtactctag aagcagctcc ccatcaaagc   3660
tga                                                                 3663
```

<210> SEQ ID NO 37
<211> LENGTH: 1220
<212> TYPE: PRT
<213> ORGANISM: artificial sequence
<220> FEATURE:
<223> OTHER INFORMATION: EHV-1 DNA polymerase (pol) protein from
      EHV-1 NY03 strain

<400> SEQUENCE: 37

```
Met Ala Ala Arg Glu Gln Ala Asn Ser Val Arg Arg Ser Gly Phe Phe
1               5                   10                  15

Asn Pro Phe Ile Gly Lys Arg Pro Phe Phe Arg Pro Gly Ser Gly Gln
            20                  25                  30

Thr Ala Glu Thr Glu Arg Pro Arg Pro Pro Gln His Ser Tyr Cys Thr
        35                  40                  45

Glu Val Gly Ser Phe Lys Phe Ile Ala Pro Arg Cys Leu Asp Glu Glu
    50                  55                  60

Ala Pro Ala Asp Gln Arg Arg Gly Val His Val Gly Thr Leu Glu Arg
65                  70                  75                  80

Pro Pro Lys Val Tyr Cys Asp Gly Ser Glu Tyr Asp Val Leu Asn Phe
                85                  90                  95

Ala Ser Gly Gly Cys Trp Pro Arg Arg Ile Arg Val Trp Asn Gly Gln
            100                 105                 110

Asp Phe Arg Gly Asp Gly Phe Asn Pro Arg Phe Glu Arg Phe His Val
        115                 120                 125

Tyr Asp Ile Val Glu Thr Ser Glu Ser Ala Ser His Asp Asp Pro Ser
    130                 135                 140

Arg Phe Ala Glu Leu Ser Arg Pro Ser Gly Ser Val Val Thr Leu Leu
```

-continued

```
145                 150                 155                 160

Gly Met Ser Glu Cys Gly Lys Arg Val Ala Val His Val Tyr Gly Val
                165                 170                 175

Arg His Tyr Phe Tyr Met Ala Lys Ala Glu Val Asp Ser Ala Cys Gly
            180                 185                 190

Ile Thr Thr Glu Ala Glu Leu Val Arg Ala Met Val Asp Cys Ala His
        195                 200                 205

Ser Ser Ala Leu Ser Ala Ala Leu Gly Asn Gly Asn Gly Gly Lys Gln
    210                 215                 220

Ser Gly Gly Ser Gly Gly Gly Trp Trp Gly Gly Lys His Val Ser Ala
225                 230                 235                 240

Asp Cys Phe Lys Val Glu Thr Val Cys His Thr Thr Leu Tyr Tyr Phe
                245                 250                 255

Gly Ser Lys Pro Ala Leu Tyr Tyr Arg Val Ser Ala Ser Ser Ser Arg
            260                 265                 270

Leu Gly Gly Phe Ile Cys Asp Asn Phe His Pro Glu Ile Thr Lys Phe
        275                 280                 285

Glu Gly Ser Val Asp Val Thr Thr Arg Leu Leu Leu Asp Asn Glu Asn
    290                 295                 300

Phe Thr Ser Phe Gly Trp Tyr Arg Leu Arg Pro Gly Thr His Gly Glu
305                 310                 315                 320

Arg Val Gln Leu Arg Pro Val Glu Arg His Val Thr Ser Ser Asp Val
                325                 330                 335

Glu Ile Asn Cys Thr Pro Asp Asn Leu Glu Pro Ile Pro Asp Glu Ala
            340                 345                 350

Ala Trp Pro Asp Tyr Lys Leu Met Cys Phe Asp Ile Glu Cys Lys Ala
        355                 360                 365

Gly Thr Gly Asn Glu Met Ala Phe Pro Val Ala Thr Asn Gln Glu Asp
    370                 375                 380

Leu Val Ile Gln Ile Ser Cys Leu Leu Tyr Ser Leu Ala Thr Gln Asn
385                 390                 395                 400

His Glu His Thr Leu Leu Phe Ser Leu Gly Ser Cys Asp Ile Ser Glu
                405                 410                 415

Glu Tyr Ser Phe Ala Cys Val Gln Arg Gly Glu Pro Arg Pro Thr Val
            420                 425                 430

Leu Glu Phe Asp Ser Glu Tyr Glu Leu Leu Val Ala Phe Leu Thr Phe
        435                 440                 445

Leu Lys Gln Tyr Ser Pro Glu Phe Ala Thr Gly Tyr Asn Ile Val Asn
    450                 455                 460

Phe Asp Trp Ala Tyr Ile Val Asn Lys Val Thr Ser Val Tyr Asn Ile
465                 470                 475                 480

Lys Leu Asp Gly Tyr Gly Lys Phe Asn Lys Gly Gly Leu Phe Lys Val
                485                 490                 495

Trp Asp Ile Ala Thr Asn His Phe Gln Lys Lys Ser Lys Val Lys Ile
            500                 505                 510

Asn Gly Leu Ile Ser Leu Asp Met Tyr Ser Val Ala Thr Glu Lys Leu
        515                 520                 525

Lys Leu Pro Ser Tyr Lys Leu Asp Ala Val Val Gly Asp Val Leu Gly
    530                 535                 540

Glu His Lys Ile Asp Leu Pro Tyr Lys Glu Ile Pro Ser Tyr Tyr Ala
545                 550                 555                 560

Gly Gly Pro Asp Arg Arg Gly Val Ile Gly Glu Tyr Cys Ile Gln Asp
                565                 570                 575
```

-continued

```
Ser Arg Leu Val Gly Lys Leu Phe Phe Lys Tyr Leu Pro His Leu Glu
            580                 585                 590

Leu Ser Ala Val Ala Lys Leu Ala Arg Ile Thr Leu Thr Arg Val Ile
        595                 600                 605

Phe Asp Gly Gln Gln Ile Arg Val Tyr Thr Cys Leu Leu Lys Leu Ala
    610                 615                 620

Arg Glu Arg Asn Phe Ile Leu Pro Asp Asn Arg Arg Arg Phe Asp Ser
625                 630                 635                 640

Gln Ala Asp Ala Ala Ser Glu Thr Ser Glu Leu Ala Met Asp Ser Gln
                645                 650                 655

Ser His Ala Phe Asp Ser Thr Asp Glu Pro Asp Gly Val Asp Gly Thr
            660                 665                 670

Pro Asp Ala Ala Gly Ser Gly Ala Thr Ser Glu Asn Gly Gly Gly Lys
        675                 680                 685

Pro Gly Val Gly Arg Ala Val Gly Tyr Gln Gly Ala Lys Val Leu Asp
    690                 695                 700

Pro Val Ser Gly Phe His Val Asp Pro Val Val Val Phe Asp Phe Ala
705                 710                 715                 720

Ser Leu Tyr Pro Ser Ile Ile Gln Ala His Asn Leu Cys Phe Thr Thr
                725                 730                 735

Leu Ala Leu Asp Glu Val Asp Leu Ala Gly Leu Gln Pro Ser Val Asn
            740                 745                 750

Tyr Ser Thr Phe Glu Val Gly Asp Gln Lys Leu Phe Phe Val His Ala
        755                 760                 765

His Ile Arg Glu Ser Leu Leu Gly Ile Leu Leu Arg Asp Trp Leu Ala
    770                 775                 780

Met Arg Lys Ala Val Arg Ala Arg Ile Pro Thr Ser Thr Pro Glu Glu
785                 790                 795                 800

Ala Val Leu Leu Asp Lys Gln Gln Ser Ala Ile Lys Val Ile Cys Asn
                805                 810                 815

Ser Val Tyr Gly Phe Thr Gly Val Ala Asn Gly Leu Leu Pro Cys Leu
            820                 825                 830

Arg Ile Ala Ala Thr Val Thr Thr Ile Gly Arg Asp Met Leu Leu Lys
        835                 840                 845

Thr Arg Asp Tyr Val His Ser Arg Trp Ala Thr Arg Glu Leu Leu Glu
    850                 855                 860

Asp Asn Phe Pro Gly Ala Ile Gly Phe Arg Asn His Lys Pro Tyr Ser
865                 870                 875                 880

Val Arg Val Ile Tyr Gly Asp Thr Asp Ser Val Phe Ile Lys Phe Val
                885                 890                 895

Gly Leu Thr Tyr Glu Gly Val Ser Glu Leu Gly Asp Ala Met Ser Arg
            900                 905                 910

Gln Ile Ser Ala Asp Leu Phe Arg Ala Pro Ile Lys Leu Glu Cys Glu
        915                 920                 925

Lys Thr Phe Gln Arg Leu Leu Leu Ile Thr Lys Lys Lys Tyr Ile Gly
    930                 935                 940

Val Ile Asn Gly Gly Lys Met Leu Met Lys Gly Val Asp Leu Val Arg
945                 950                 955                 960

Lys Asn Asn Cys Ser Phe Ile Asn Leu Tyr Ala Arg His Leu Val Asp
                965                 970                 975

Leu Leu Leu Tyr Asp Glu Asp Val Ala Thr Ala Ala Ala Glu Val Thr
            980                 985                 990
```

-continued

```
Asp Val Pro Pro Ala Glu Trp Val  Gly Arg Pro Leu Pro  Ser Gly Phe
        995                 1000                 1005

Asp Lys  Phe Gly Arg Val Leu  Val Glu Ala Tyr Asn  Arg Ile Thr
    1010                 1015                 1020

Ala Pro  Asn Leu Asp Val Arg  Glu Phe Val Met Thr  Ala Glu Leu
    1025                 1030                 1035

Ser Arg  Ser Pro Glu Leu Tyr  Thr Asn Lys Arg Leu  Pro His Leu
    1040                 1045                 1050

Thr Val  Tyr Phe Lys Leu Ala  Met Arg Asn Glu Glu  Leu Pro Ser
    1055                 1060                 1065

Val Lys  Glu Arg Ile Pro Tyr  Val Ile Val Ala Gln  Thr Glu Ala
    1070                 1075                 1080

Ala Glu  Arg Glu Ala Gly Val  Val Asn Ser Met Arg  Gly Thr Ala
    1085                 1090                 1095

Gln Asn  Pro Val Val Thr Lys  Thr Ala Arg Pro Gln  Pro Lys Arg
    1100                 1105                 1110

Lys Leu  Leu Val Ser Asp Leu  Ala Glu Asp Pro Thr  Tyr Val Ser
    1115                 1120                 1125

Glu Asn  Asp Val Pro Leu Asn  Thr Asp Tyr Tyr Phe  Ser His Leu
    1130                 1135                 1140

Leu Gly  Thr Ile Ser Val Thr  Phe Lys Ala Leu Phe  Gly Asn Asp
    1145                 1150                 1155

Val Arg  Thr Thr Glu Asn Leu  Leu Lys Arg Phe Ile  Pro Glu Thr
    1160                 1165                 1170

Pro His  Lys Thr Pro Thr Lys  Thr Gln Ala Leu Leu  Glu Arg Ala
    1175                 1180                 1185

Gly Phe  Glu Lys Leu Thr Pro  Phe Thr Pro Glu Glu  Glu Ser Arg
    1190                 1195                 1200

Arg Ile  Leu His Thr Val Phe  Cys Thr Leu Glu Ala  Ala Pro His
    1205                 1210                 1215

Gln Ser
    1220
```